(12) United States Patent
Hefti

(10) Patent No.: US 6,287,874 B1
(45) Date of Patent: Sep. 11, 2001

(54) METHODS FOR ANALYZING PROTEIN BINDING EVENTS

(75) Inventor: John Hefti, San Francisco, CA (US)

(73) Assignee: Signature BioScience, Inc., Hayward, CA (US)

( * ) Notice: Subject to any disclaimer, the term of this patent is extended or adjusted under 35 U.S.C. 154(b) by 0 days.

(21) Appl. No.: 09/365,580

(22) Filed: Aug. 2, 1999

Related U.S. Application Data

(63) Continuation-in-part of application No. 09/243,194, filed on Feb. 1, 1999.
(60) Provisional application No. 60/073,445, filed on Feb. 2, 1998, and provisional application No. 60/134,740, filed on May 18, 1999.

(51) Int. Cl.[7] .................. G01N 33/566; G01N 33/00; G01N 25/18
(52) U.S. Cl. .................. 436/501; 436/86; 436/149
(58) Field of Search .................. 435/6; 422/50, 422/82.01

(56) References Cited

U.S. PATENT DOCUMENTS

| | | | |
|---|---|---|---|
| 4,822,566 | 4/1989 | Newman | 422/82.01 |
| 5,025,222 | 6/1991 | Scott . | |
| 5,156,810 | 10/1992 | Ribi | 422/82.01 |
| 5,164,319 | 11/1992 | Hafeman et al. | 435/287.1 |
| 5,424,186 | 6/1995 | Fodor et al. | 435/6 |
| 5,532,128 | 7/1996 | Eggers et al. | 435/6 |

(List continued on next page.)

FOREIGN PATENT DOCUMENTS

| | | |
|---|---|---|
| 0 519 250 | 5/1992 | (EP) . |
| WO 93 08464 | 4/1993 | (WO) . |
| WO 97/41425 | 4/1996 | (WO) . |
| WO 96/36871 | 11/1996 | (WO) . |
| WO 98 09168 | 3/1998 | (WO) . |
| WO 98 31839 | 7/1998 | (WO) . |

(List continued on next page.)

OTHER PUBLICATIONS

Abou–Aid et al., "Dielectric Relaxation of Aqueous Solutions of Ribonuclease A in the Absence and Presence of Urea", Ber. Bunsenges. Phys. Chem. 101(12):1921–1927 (1997).

Karunanayakc, "Capacitive Sensors for In–Vivo Measurements of the Dielectric Properties of Biological Materials", IEEE Transactions on Instrumentation and Measurement, 37(1):101–105 (1988).

Stuchly, "Coaxial Line Reflection Methods for Measuring Dielectric Properties of Biological Substances at Radio and Microwave Frequencies—A Review", IEEE Transactions on Instrumentation and Measurement, IM–29(3):176–183 (1980).

(List continued on next page.)

Primary Examiner—Kenneth R. Horlick
Assistant Examiner—Teresa Strzelecka
(74) Attorney, Agent, or Firm—Scott L. Ausenhus; Clifford B. Perry; Richard L. Neeley

(57) ABSTRACT

The present invention provides a variety of methods of analyzing protein binding events using a system capable of directly detecting protein/ligand complexes based upon the dielectric properties of the complex. The system can be used in a variety of analyses involving protein binding events, such as screening ligand libraries, characterizing protein binding interactions, and identifying ligands. The system can also be utilized in diverse analytical and diagnostic applications.

45 Claims, 33 Drawing Sheets

U.S. PATENT DOCUMENTS

| | | |
|---|---|---|
| 5,565,325 | 10/1996 | Blake ................................. 435/7.1 |
| 5,653,939 | 8/1997 | Hollis et al. ........................ 422/50 |
| 5,656,428 | 8/1997 | McAllister et al. . |
| 5,827,482 | 10/1998 | Shieh et al. ..................... 422/82.02 |
| 5,834,318 | 11/1998 | Buettner ............................ 436/518 |
| 5,841,914 | 11/1998 | Shieh et al. ........................ 385/12 |
| 5,846,708 | 12/1998 | Hollis et al. ......................... 435/6 |
| 5,846,842 | 12/1998 | Herron et al. ..................... 436/518 |
| 5,846,843 | 12/1998 | Simon ............................... 436/527 |
| 5,858,666 | 1/1999 | Weiss . |
| 5,866,341 | 2/1999 | Spinella et al. ..................... 435/71 |
| 5,874,219 | 2/1999 | Rava et al. ........................... 435/6 |
| 5,966,017 | 10/1999 | Scott ................................. 324/639 |
| 6,048,692 | 4/2000 | Maracas et al. . |

FOREIGN PATENT DOCUMENTS

| | | |
|---|---|---|
| WO 98/35232 | 8/1998 | (WO) . |
| WO 99/18242 | 4/1999 | (WO) . |
| WO 99 39190 | 8/1999 | (WO) . |

OTHER PUBLICATIONS

Amo et al., "Dielectric Measurements of Lysozyme and Tri–N–Acetyl–D–Glucosamine Association at Radio and Microwave Frequencies", Biosensors & Bioelectronics, 12(9–10):953–958 (1997).

Hianik, "Biosensors Based on Solid Supported Lipid Bilayers and their Physical Properties", Nato Asi Ser., Ser. 2 (1997), 38 (Biosensors for Direct Monitoring of Enviromental Pollutata in Field), 317–333.

Smith et al., "Dielectric Relaxation Spectroscopy and Some Applications in the Pharmaceutical Sciences", Journal of Pharmaceutical Sciences, 84(9):1029–1044 (1995).

Phizicky, Eric M. and Fields, Stanley: Protein–Protein Interactions: Methods for Detection and Analysis, *Microbiological Reviews*, Mar., 1995, vol. 59, No. 1, pp. 94–123.

Hollis et al., A Swept Frequency Magnitude Method for the Dielectric Characterization of Chemical and Biological Systems, IEEE Transactions on Microwave Theory and Techniques, vol. MTT–28, No. 7, Jul. 1980, pp. 791–801.

METHODS FOR ANALYZING PROTEIN BINDING EVENTS

CROSS-REFERENCES TO RELATED APPLICATIONS

This application is a continuation-in-part of U.S. application Ser. No. 09/243,194 filed Feb. 1, 1999, which claims the benefit of U.S. Provisional Application No. 60/073,445, filed Feb. 2, 1998. This application also claims the benefit of U.S. Provisional Application 60/134,740 filed May 18, 1999. This application is also related to U.S. application Ser. No. 09/365,978, filed Aug. 2, 1999 and U.S. application Ser. No. 09/365,581, filed Aug. 2, 1999, both of which were filed concurrently herewith. Each of these applications is incorporated herein by reference in their entirety for all purposes.

FIELD OF INVENTION

The present invention broadly relates to methods for detecting binding interactions between proteins and various types of ligands. More specifically, the present invention relates to methods for screening large collections of ligands for those having specific affinity for a protein target of interest. As such, the present invention is useful within the fields of fundamental biomedical and biochemical research, especially drug discovery and medical diagnostics.

BACKGROUND OF THE INVENTION

Proteins play a variety of key roles in biological processes and functions, including for example, functioning as catalysts, regulators of biochemical pathways, receptors, and as important elements in immune response. Given their diverse and important roles, it is not surprising that ligands that bind to proteins have been viewed by pharmaceutical researchers as attractive candidates for therapeutic agents. One traditional approach for drug discovery simply involved making modifications to natural regulators. As more data regarding structure function relationships became available, it became possible to engage in rational drug design using computers and x-ray structures to aid in synthesizing molecules tailored to fit the active site of an enzyme, for example. However, even using such advanced techniques, drug screening and development remained an often tedious and time consuming process.

More recent drug discovery methods take a different approach and involve screening extremely large libraries of compounds for their ability to bind protein targets of interest. This type of approach typically begins with the identification of a potential protein target, such as a receptor for example. A diverse library is then prepared containing ligands to be screened for their ability to bind the target. The libraries may be random peptide libraries, carbohydrate libraries, natural product libraries, etc. Often the libraries are prepared using recently developed combinatorial techniques. These libraries are subsequently subjected to high throughput screening to identify ligands that bind to the target. Because the key feature of this approach is to screen a huge number of molecules, the success of this approach hinges on the ability to rapidly screen and identify ligands that do bind the target. Ligands initially identified as binding the target are then used to develop more focused libraries that are then put through the same screening process. This process of screening and preparing new focused libraries typically is repeated several times until a relatively small population of lead compounds are identified. These lead compounds are then subjected to various pharmaceutical analyses to select useful drug candidates.

A primary limitation in current methods is that the screening tests simply detect binding, but are unable to distinguish between specific and non-specific binding. Some approaches also are not fully compatible with high-throughput screening procedures. Moreover, many current screening methods require labeling of either the target or ligand and are unable to detect binding complexes directly.

The present invention provides novel methods for analyzing protein binding events in which the formation of protein/ligand complexes can be directly detected. Using this system, it is possible to screen libraries on the basis of specific binding interactions. It is also possible to perform a variety of analytical and diagnostic analyses with the system of the present invention.

SUMMARY OF THE INVENTION

The present invention generally provides methods for detecting binding events between proteins and a variety of different types of ligands utilizing a system which is sensitive to the dielectric properties of molecules and binding complexes such as protein/ligand complexes. Other methods involve screening libraries of ligands to identify those ligands which bind to a protein of interest, such methods have particular utility in drug screening programs, for example. Other methods are diagnostic methods in which the system is used to detect the presence of a particular ligand that binds to a known protein, or of a particular protein that binds to a known ligand. The screening and diagnostic methods can be performed using arrays having multiple elements.

More specifically, some methods involve obtaining a spectrum for a protein/ligand complex. Such methods include acquiring a spectrum for a protein/ligand complex formed between a protein and a test ligand. The spectrum is acquired by propagating a test signal along a signal path and detecting a response signal for the protein/ligand complex, wherein the protein or test ligand is electromagnetically coupled to a portion of the signal path. The test signal propagated along the signal path is varied with time to obtain the spectrum. The test signal is varied, for example, by altering the frequency or wavelength with time.

Certain methods involve screening ligands for the ability to bind to a target protein or protein of interest. The method includes contacting a protein of interest with a ligand. The formation of a protein/ligand complex is detected through the formation of a response signal resulting from the complex. Typically, either the protein of interest or test ligand is electromagnetically coupled to a portion of a continuous transmission line.

Some screening methods of the present invention are more sophisticated and include acquiring a spectrum for a protein/ligand complex between a known protein and a test ligand wherein either the known protein or test ligand are electromagnetically coupled to a portion of a signal path. The spectrum is acquired by propagating a test signal that is varied with time along the signal path and detecting a response signal for the complex between the known protein and the test ligand. The resulting spectrum is then examined for the presence of a known signal which is characteristic for the binding of a known ligand at a particular site on the known protein. The presence of the known signal in the spectrum is indicative of the test ligand binding at the particular site to which the known ligand binds. For tests in which the known protein is an enzyme, the particular site can be the active site or an allosteric site, for example. When the known protein is a receptor, the particular site can be the site at which a natural ligand binds. The particular site for tests conducted with a known antibody typically is the antigen binding site for a known antigen.

In related screening methods, the spectrum is examined for the presence of a known signal which is characteristic for the binding of a particular class of ligand to the known protein. Thus, for methods in which the known protein is an enzyme, the known signal is for a complex with a competitive inhibitor or an allosteric inhibitor, for example. In instances in which the known protein is a receptor, the known signal is for a complex with an agonist or antagonist, for example.

The present invention also provides various diagnostic methods for detecting the presence of a particular protein or ligand in a sample. Hence, some methods include contacting a known protein that is electromagnetically coupled to a portion of a continuous transmission line with a sample potentially containing a particular ligand that specifically binds with the known protein. A sufficient period of time is allowed to elapse to permit the known protein and the particular ligand of interest, if present, to form a binding complex. Detection of a response signal for the binding complex is indicative of the presence of the particular ligand in the sample. Alternatively, a known ligand can be electromagnetically coupled to a portion of a transmission line and then contacted with a sample potentially containing a particular protein that forms a binding complex with the known ligand.

As with the more sophisticated screening methods, certain diagnostic methods include the use of characteristic signals for detection of the presence of a particular protein or ligand in a sample. More specifically, such diagnostic methods include contacting a known protein coupled to a portion of a signal path with a sample potentially containing a particular ligand that forms a binding complex with the known protein. A test spectrum is acquired by propagating a test signal along the signal path and detecting a response signal for the binding complex, wherein the propagating step comprises varying the test signal with time. The test spectrum is then examined for the presence of a known signal that is characteristic for the binding complex; the presence of such a signal indicates the presence of the particular ligand in the sample. Alternatively, a known ligand rather than a known protein is coupled to the signal path. In this instance, the methods include examining the acquired test spectrum for the presence of signals which are characteristic for a binding complex formed between the known ligand and a particular protein, the presence of such signals being indicative of the presence of the particular protein in the test sample.

Still other methods include the use of arrays that contain a plurality of sites or elements. Each element includes a continuous transmission line and a known protein (or plurality of proteins) electromagnetically coupled to a portion of the continuous transmission line located within the element. These elements are contacted with a sample containing a ligand. A response signal for the binding complex formed between the known protein and ligand is detected and indicates that the ligand is able to bind to the proteins. In other methods, known ligands rather than known proteins are attached to each site of the array and contacted with proteins contained in a sample.

Because the present methods involve direct detection of binding events, it is not necessary to use labeled proteins or ligands, thus simplifying the methods and reducing costs relative to other approaches for monitoring protein/ligand binding events. The ability to differentiate between different types of binding also makes it possible to much more rapidly screen for molecules that are of potential therapeutic value.

DESCRIPTION OF THE SPECIFIC EMBODIMENTS

I. Definition of Terms

Figure 1A:
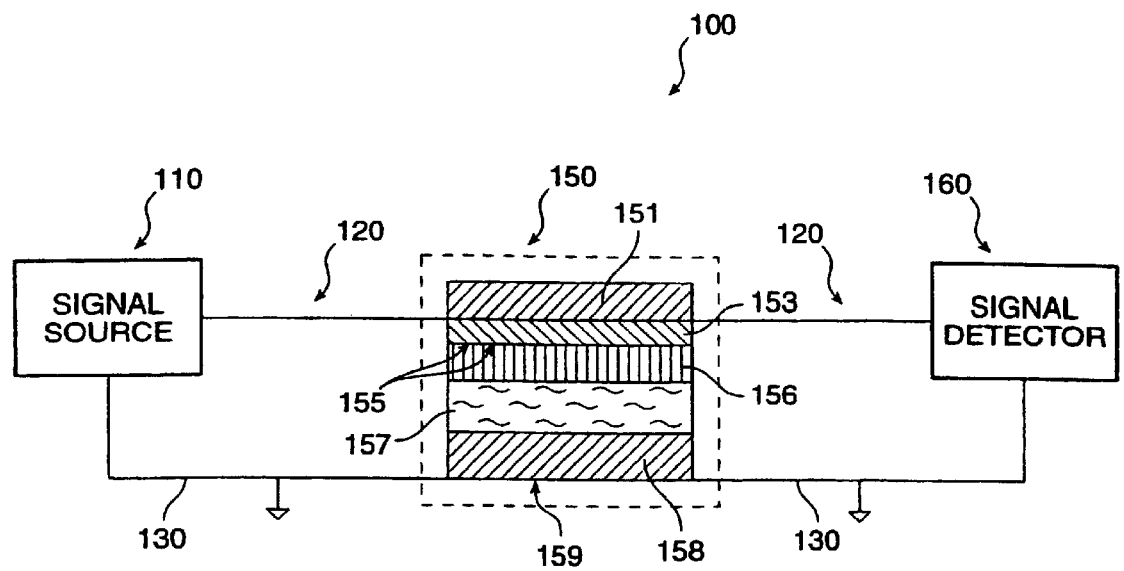
FIG. 1A illustrates one embodiment of the bio-assay system in accordance with the present invention.

The terms biological "binding partners" or "ligand/ antiligand" or "ligand/antiligand complex" refers to molecules that specifically recognize (e.g. bind) other molecules to form a "binding complex" such as antibody-antigen, lectin-carbohydrate, nucleic acid-nucleic acid, biotin-avidin, etc. Biological binding partners need not be limited to pairs of single molecules. Thus, for example, a single ligand may be bound by the coordinated action of two or more "antiligands".

The terms "ligand" or "analyte" or "marker" refers to any molecule being detected. It is detected through its interaction with an antiligand, which specifically or non-specifically binds the ligand, or by the ligand's characteristic dielectric properties. The ligand is generally defined as any molecule for which there exists another molecule (i.e. an antiligand) which specifically or non-specifically binds to said ligand, owing to recognition of some portion of said ligand. The antiligand, for example, can be an antibody and the ligand a molecule such as an antigen which binds specifically to the antibody. In the event that the antigen is bound to the surface and the antibody is the molecule being detected, for the purposes of this document the antibody becomes the ligand and the antigen is the antiligand. The ligand may also consist of cells, cell membranes, organelles and synthetic analogues thereof.

Suitable ligands for practice of this invention include, but are not limited to, antibodies, antigens, nucleic acids (e.g. natural or synthetic DNA, RNA, gDNA, cDNA, mRNA, tRNA, etc.), lectins, sugars, oligosaccharides, glycoproteins, receptors, growth factors, cytokines, small molecules such as drug candidates (from, for example, a random peptide library, a natural products library, a legacy library, a combinatorial library, an oligosaccharide library and a phage display library), metabolites, drugs of abuse and their metabolic by-products, enzyme substrates, enzyme inhibitors, enzyme co-factors such as vitamins, lipids, steroids, metals, oxygen and other gases found in physiologic fluids, cells, cellular constituents, cell membranes and associated structures, cell adhesion molecules, natural products found in plant and animal sources, tumor markers (i.e., molecules associated with tumors), other partially or completely synthetic products, and the like. A "natural ligand" is a ligand which occurs in nature and specifically binds to a particular site(s) on a particular antiligand such as a protein. Examples by way of illustration and not limitation include a receptor and a ligand specific for the receptor (e.g., an agonist or antagonist), an enzyme and an inhibitor, substrate or cofactor; and an antibody and an antigen.

An "antiligand" refers to a molecule which specifically or nonspecifically binds another molecule (i.e., a ligand). The antiligand is also detected through its interaction with a ligand to which it specifically binds or by its own characteristic dielectric properties. As used herein, the antiligand is usually immobilized on the surface, either alone or as a member of a binding pair that is immobilized on the surface. In some embodiments, the antiligand may consist of the molecules on the signal path or conductive surface. Alternatively, once an antiligand has bound to a ligand, the resulting antiligand/ligand complex can be considered an antiligand for the purposes of subsequent binding.

The term "specifically binds" when referring to a protein or polypeptide, nucleic acid, or receptor or other binding partners described herein, refers to a binding reaction which is determinative of the cognate ligand of interest in a heterogenous population of proteins and/or other biologics. Thus, under designated conditions (e.g. immunoassay conditions in the case of an antibody), the specified ligand or antibody binds to its particular "target" (e.g. a hormone specifically binds to its receptor) and does not bind in a significant amount to other proteins present in the sample or to other proteins to which the ligand or antibody may come in contact in an organism or in a sample derived from an organism. A ligand that specifically binds to a protein is one that binds at the same site as a natural ligand.

The terms "isolated," "purified," or "biologically pure" mean an object species is the predominant species present (i.e., on a molar basis it is more abundant than any other individual species in the composition), and preferably a substantially purified fraction in a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

"Polypeptide", "peptide," "protein" and "protein target" are used interchangeably to refer to a polymer of amino acid residues. The terms apply to amino acid polymers in which one or more amino acid residue is an artificial chemical analogue of a corresponding naturally occurring amino acid, as well as to naturally occurring amino acid polymers. The protein or protein target to which ligands are being screened in drug discovery methods can be of essentially any type capable of binding some type of ligand including, by way of example and not limitation, enzymes, receptors, antibodies and fragments thereof, hormones, and nucleic acid binding proteins. A protein or peptide may include a particular site, this site is the site at which a ligand and the protein or peptide form a binding complex. For an enzyme, the particular site can be the active site or an allosteric site; in the instance of a receptor, the particular site is the site at which a natural ligand binds.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to VH–CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879–5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complimentarily determining regions" or "CDRs" and are characterized, for example by Kabat et al. Sequences of proteins of immunological interest, 4th ed. U.S. Dept. Health and Human Services, Public Health Services, Bethesda, Md. (1987).

"Epitope" is that portion of an antigen that interacts with an antibody.

The terms "immunological binding" and "immunological binding properties" refer to the non-covalent interactions of the type which occur between an immunoglobulin molecule and an antigen for which the immunoglobulin is specific.

"Sample" refers to essentially any source from which nucleic acids can be obtained. A sample may be acquired from essentially any organism, including animals and plants, as well as cell cultures, recombinant cells and cell components. Samples can be from a biological tissue, fluid or specimen and may be obtained from a diseased or healthy organism. Samples may include, but are not limited to, sputum, amniotic fluid, blood, blood cells (e.g., white cells), urine, semen, peritoneal fluid, pleural fluid, tissue or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Similarly, plant material used in the invention may be conveniently derived from agriculture or horticultural sources, and other sources of natural products. Alternatively a biological sample may be obtained from a cell or blood bank where tissue and/or blood are stored, or from an in vitro source, such as a culture of cells. Techniques for establishing a culture of cells for use as a source for biological materials are well known to those of skill in the art. Freshney, *Culture of Animal Cells, a Manual of Basic Technique, Third Edition*, Wiley-Liss, N.Y. (1994) provides a general introduction to cell culture.

The term "signal path" refers to a transmission medium along the bio-electrical interface which is capable of supporting an electromagnetic signal of any useful frequency including a DC static field. A non-exhaustive list of signal paths include conductive and dielectric waveguide structures, multiple-conductor transmission mediums such as transverse electromagnetic (TEM) transmission lines, transmission lines with three or more conductive elements which support TE, TM or TEM mode propagation such as quadrupolar and octupolar lines, coupled waveguides, resonant cavity structures which may or may not be coupled, other non-modal structures like wires, printed circuits, and other distributed circuit and lumped impedance conductive structures, and the like. The signal path may structurally comprise the signal plane, the ground plane, or a combination of both structures. Typically, the signal path is formed along a direction which is non-orthogonal to the surface of the molecular binding region (MBR). In embodiments in which the signal path consists of a conductive layer or region, the conductive region extends continuously over that range. In embodiments in which the signal path is non-metallic, i.e., a dielectric waveguide, the signal path is defined as the path having the least amount of signal loss or as having a conductivity of greater than 3 mhos/m.

A "transmission line" is a conductive element, typically gold-plate nickel, which can support the propagation of an electromagnetic signal at some predefined frequency. "Signal path" is a broader term to use (i.e. a transmission line is one type of signal path).

A "molecular binding region" or "MBR" refers to a layer having of at least one molecular structure (i.e., an analyte, antiligand, or a ligand/antiligand pair, etc.) coupled to the signal path along the bio-electrical interface. The molecular binding region may consist of one or more ligands, antiligands, ligand/antiligand complexes, linkers, matrices of polymers and other materials, or other molecular structures described herein. Further, the molecular binding region may be extremely diverse and may include one or more components including matrix layers and/or insulating layers, which may have one or more linking groups. The MBR is coupled to the signal path either via a direct or indirect physical connection or via electromagnetic coupling when the ligand is physically separated from the signal path. The MBR may be of a derivatized surface such as by thiol linkers biotinylated metals and the like, all in accordance with standard practice in the art.

The term "binding event" refers to an interaction or association between a minimum of two molecular structures, such as a ligand and an antiligand. The interaction may occur when the two molecular structures as are in direct or indirect physical contact or when the two structures are physically separated but electromagnetically coupled therebetween. Examples of binding events of interest in a medical context include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Alternatively, the term "binding event" may refer to a single molecule or molecular structure described herein, such as a ligand, or an antiligand/ligand complex, which is bound to the signal path. In this case the signal path is the second molecular structure.

A "ligand/antiligand complex" refers to the ligand bound to the antiligand. The binding may be specific or non-specific, and the bonds are typically covalent bonds, hydrogen bonds, immunological binding, Van der Waals forces, or other types of binding.

"Coupling" refers to the transfer of energy between two structures either through a direct or indirect physical connection or through any form of signal coupling, such as electrostatic or electromagnetic coupling. Thus, "electromagnetic coupling" refers to energy transfer through electromagnetic interactions.

A "test signal" refers to a signal propagating at any useful frequency defined within the electromagnetic spectrum. For examples, the test signal frequency is at or above 1 MHz, such as 5 MHz 10 MHz, 20 MHz, 45 MHz, 100 MHz, 500 MHz, 1 GHz, 5 GHz, 10 GHz, 30 GHz, 50 GHz, 100 GHz, 500 GHz, 1000 GHz and frequencies ranging therebetween.

An "enzyme," refers to a protein which acts as a catalyst to reduce the activation energy of a chemical reaction in other compounds or "substrates", but is not a final product in the reaction.

"Solution" includes a material in which a ligand resides. A non-exhaustive list of solutions includes materials in solid, liquid or gaseous states. Solid solutions may be comprised of naturally-occurring or synthetic molecules including carbohydrates, proteins, oligonucleotides, or alternatively, any organic polymeric material, such as nylon, rayon, dacryon, polypropylene, teflon, neoprene, delrin or the like. Liquid solutions include those containing an aqueous, organic or other primary components, gels, gases, and emulsions. Exemplary solutions include celluloses, dextran derivatives, aqueous solution of d-PBS, Tris buffers, deionized water, blood, physiological buffer, cerebrospinal fluid, urine, saliva, water, organic solvents. The solution is used herein to refer to the material in which the ligand and/or antiligand are applied to the binding surface. The solution contains the sample to be analyzed.

A "linking group" or "linker" refers to chemical structures which are used to attach any two components on the bio-assay device. The linking groups thus have a first binding portion that binds to one component, such as the conductive surface, and have a second binding portion that binds to another component such as the matrix or the antiligand.

The term "bio-assay device" refers to a structure in which the molecular binding region is formed. The bio-assay device may consist of a surface, recessed area, or a hermetically sealed enclosure, all of which may be any particular size or shape.

A "bio-assay system" refers to the bio-assay device as described above, in connection with the components necessary to electromagnetically probe and detect the bio-assay device. These components include, but are not limited to, the signal path(s), substrate(s), electronic devices such as signal generators, oscilloscopes, and vector analyzers necessary to probe to and detect signals from the bio-assay device, microchips and microprocessors which can probe and detect electromagnetic signals and analyze data, and the like.

The terms "resonant" or "resonance" refer generally to a rapidly changing dielectric response as a function of frequency.

A "bio-electrical interface" refers to an interface structure between a signal path for supporting the propagation of a test signal and a molecular binding region.

The term "matrix" or "binding matrix" refers to a layer of material on the bioassay chip that is used as a spacer or to enhance surface area available for binding or to optimize orientation of molecules for enhanced binding, or to enhance any other property of binding so as to optimize the bio-assay device. The matrix layer may be comprised or carbohydrates such as dextran, poly amino acids, cross-linked and non-cross linked proteins, and the like.

II. Introduction

A. General

The present invention generally provides methods for analyzing protein binding events involving the binding of a protein (for example, a receptor, an enzyme, an antibody, etc.) to various types of ligands, such as inhibitors, agonists, antagonists, drugs, and the like. More specifically, certain methods include screening large libraries of molecules to identify those which bind to a particular protein of interest and which thus potentially have a biological activity of interest; such methods have particular utility in drug discovery programs, for example. Other methods include the use of proteins to assay for the presence of a particular ligand in a sample. Still other methods involve the use of profiles to distinguish, identify or quantify certain protein binding events, or to provide structural information about a protein or protein interaction.

Certain screening methods involve observing a signal that is generated due to binding of a ligand by a protein in which is the ligand or the protein is electromagnetically coupled to a signal path such as a transmission line. Other more complex screening methods involve acquiring a spectrum for a protein/ligand complex and then examining the spectrum for signals which are characteristic of certain structural motifs or binding interactions. With such methods, it is possible, for example, to obtain information regarding the type of ligand and the type of binding interaction.

The methods are amenable to being conducted using an array which includes multiple elements or sites, each element or site including a different protein or ligand. Each element of the array includes a signal path such as a transmission line. A protein or ligand (or plurality thereof) is electromagnetically coupled to each of the signal paths that are part of the array. A signal is launched down a plurality of transmission lines, each running to a different element of the array. A transmitted and/or reflected signal as modulated by the presence of a binding complex is then used to analyze the nature of the binding at the various elements on the array.

B. The Bio-Assay System

The present invention makes use of the observation that a vast number of molecules can be distinguished based upon the unique dielectric properties most molecules exhibit. These distinguishing dielectric properties can be observed by coupling a signal to the bound molecular structure. The unique dielectric properties of the bound molecular structure modulate the signal, giving it a unique signal response. The unique signal response can then be used to detect and identify the ligands and other molecules which make up the molecular binding region. Although the following description of the system is often described with reference to ligands and antiligands because of its broad applicability, it should be understood that the ligands and antiligands can specifically include a protein target and any of a number of different ligands capable of binding to the protein target. Similarly, although reference is broadly made to binding events, such events can include the binding of a ligand to a protein.

FIG. 1A illustrates one embodiment of a bio-assay system 100 in accordance with the present invention. The system 100 is illustrated in a two conductor, signal-plane ground-plane, circuit topology which may be realized in a multitude of architectures including lumped or distributed element circuits in microstrip, stripline, coplanar waveguide, slotline or coaxial systems. Moreover, those of skill in the art of electronics will readily appreciate that the system may be easily modified to a single conductor waveguide system, or a three or more conductor system.

As illustrated, the system 100 includes a signal source 110, transmission lines 120, a source/detector ground plane 130, a bio-assay device 150, and a signal detector 160. The illustrated embodiment shows two transmission lines 120 coupled to the bio-assay device 150, although in alternative embodiments a single transmission line can be coupled to the bio-assay device or further alternatively, three or more transmission lines can be coupled to the bio-assay device 150. Transmission lines 120 are formed from a material which can support the propagation of a signal over the desired frequency of operation. Transmission lines 120 are realized as a conductive layer, such as gold, deposited on a substrate, such as alumina, diamond, sapphire, polyimide, or glass using conventional photolithography or semiconductor processing techniques.

The system 100 further includes a bio-assay device 150 coupled to the transmission lines 120. The bio-assay device 150 contains a supporting substrate 151 onto which an interface transmission line 153 is disposed. The interface transmission line153 forms an interface for supporting the propagation of a test signal. The supporting substrate 151 may consist of any insulating material such as glass, alumina, diamond, sapphire, silicon, gallium arsenide or other insulating materials used in semiconductor processing.

A molecular binding region (MBR) 156 is coupled to one or more areas of the interface transmission line 153. As those of skill in the art of electronics will appreciate, coupling may occur either through a direct connection between the interface transmission line 153 and MBR 156 as illustrated, or alternatively through signal coupling, further described below.

The MBR 156 is primarily composed of one or more ligands, although other molecules and structures may also be included, as described herein. The MBR 156 may consist of only one bound ligand tier, for instance in the case of primary binding, or it may consist of two, three, four, five or more bound ligand tiers, in the instances where there are secondary or higher-order binding events occurring. Multiple ligand tiers may occur at different binding surfaces 155 over the same interface transmission line 153.

In the illustrated embodiment, dielectric substrate 158 is located between solution 157 and the bio-assay device ground plane 159. In the illustrated embodiment, dielectric layer 158 and the bio-assay device ground plane 159 are located within the bio-assay device 150, although in alternative embodiments, one or both may be located externally. Furthermore, the MBR 156 and solution 157 arrangement may be switched and moved towards the ground plane alternatively, or in addition to these layer's proximity to the interface transmission line 153.

The system 100 includes a signal source 110 which launches the test signal onto the transmission line 120 and towards the bio-assay device 150. A signal detector 160 is positioned along the transmission path to detect the resulting signal (either reflected or transmitted or both). When the signal propagates along the interface transmission line 153 of the bio-assay device 150, the dielectric properties of the MBR 156 modulates the test signal. The modulated signal can then be recovered and used to detect and identify the molecular binding events occurring within the bio-assay device, further described below.

In an alternative embodiment of the invention, detection and identification of a ligand, antiligand/ligand complex (e.g., a binding complex between a protein target and a ligand) or other molecular structure described herein is possible when it is physically separated from the interface transmission line 153. In this embodiment, the ligand is not physically connected to the transmission line 153 but is electrically or electromagnetically coupled to the interface transmission line 153. The coupling between the interface transmission line 153 and the suspended ligand will alter the response of the test signal propagating along the interface transmission line 153, thereby providing a means for detecting and/or identifying it. The maximum separation between the interface transmission line 153 and suspended ligand is determined by such factors as the effective dielectric constant of the medium between the interface transmission line 153 and the ligand, the total coupling area, the sensitivity of the signal detector, concentration of the ligands in solution, and the desired detection time. Separation distances are typically on the order of $10^{-1}$m, $10^{-2}$m $10^{-3}$m, $10^{-4}$m, $10^{-5}$m, $10^{-6}$m, $10^{-7}$m, $10^{-8}$m, $10^{-9}$m, $10^{-10}$m, range anywhere therebetween.

In some embodiments, such as cell based assays, the MBR may be electromagnetically coupled to the signed path through the solution. Thus, cells, and in particular cell membranes and membrane-based structures may couple to the signal.

Figure 1B:
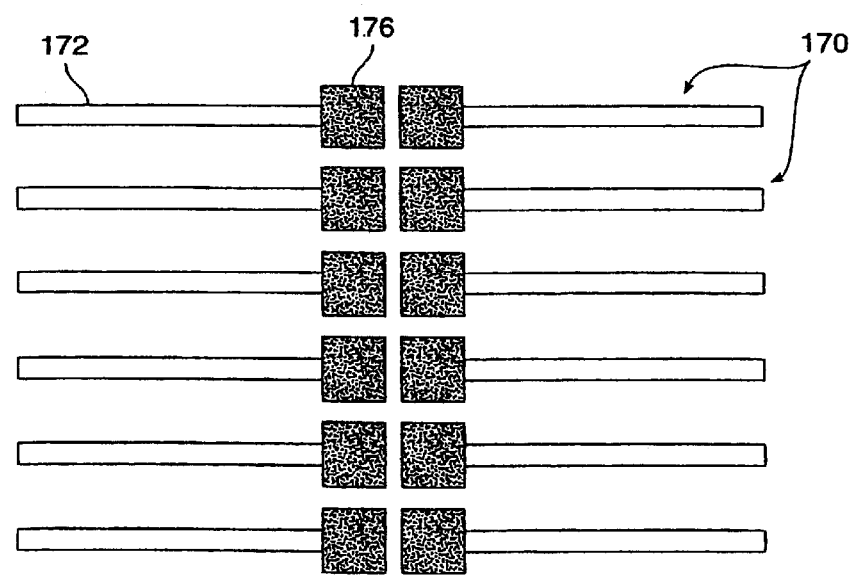
FIG. 1B illustrates a second embodiment of the bio-assay system in accordance with the present invention.

FIG. 1B illustrates a second embodiment of the bio-assay system comprising an array of resonant microstrip circuits 170. Each resonant circuit 170 consists of a transmission line 172 terminating in an open-circuited stub 176. Those skilled in the art of circuit design will appreciate other resonant structures may be employed in lumped element or distributed circuit topologies, or combinations thereof.

Figure 1C:
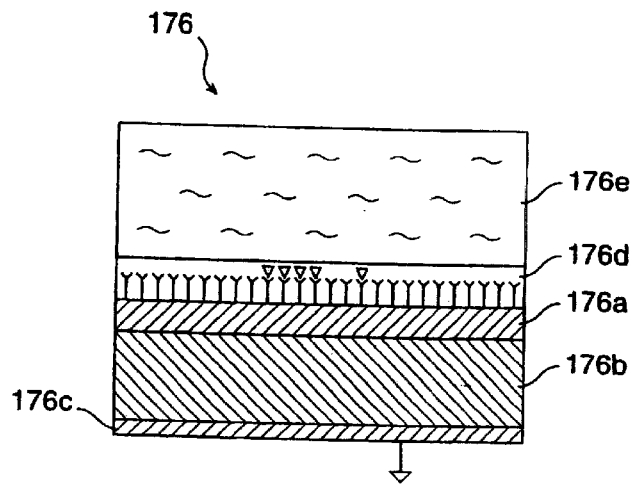
FIG. 1C illustrates a cross-section view of the bio-assay system shown in FIG. 1B.

FIG. 1C illustrates a cross-section view of one resonant circuit 170. The open-circuited stub 176 forms the bio-electrical interface of the resonant circuit 170 and closely parallels the bio-electrical interface shown in FIG. 1A. In particular, the open-circuited stub 176 consists of an interface transmission line 176a deposited on a dielectric layer 176b, and is positioned above ground plane 176c.

In this embodiment, the MBR 176d is coupled via a direct connection to transmission line 176a. The MBR 176d can bind along the interface transmission line in a specific or non-specific manner. As above, the subject molecular structure may be suspended from, but electrically coupled or electromagnetically coupled, to the interface transmission line 176a to provide binding event detection and identification information.

The dimensions of the interface transmission line 176a are influenced by considerations such as the desired measurement time (a larger area resulting in faster detection time), the desired resonant frequency fres, certain impedance matching conditions to achieve higher efficiency or cause discontinuities to highlight binding events, and the process by which the entire array is formed. For instance, if conventional microwave photolithography is used, the binding surface area may range from $10^{-1}m^2$ to $10^{-6}m^2$ using a relatively thick dielectric layer such as alumina, diamond, sapphire, duriod or other conventional substrate materials. Alternatively, if semiconductor processing is used, the binding surface area may range from $10^{-6}m^2$ to $10^{-12} m^2$ using a relatively thin dielectric layer of silicon or gallium arsenide.

Using conventional microwave design techniques or CAD tools such as Microwave Spice™, EEsof Touchstone™ and Libra™, the length and impedance of the transmission line 172, the dimensions of the interface transmission line 176a, and the thickness and dielectric constant of the dielectric layer 176b can be selected such that the resonant structure exhibits a resonant signal response at a desired resonant frequency point $f_{res}$. The desired resonant frequency $f_{res}$ point is typically the frequency range over which the molecules of interest exhibit a dramatic change in their dielectric properties, the measurement of which will enable their detection. Alternatively, the resonant frequency point $f_{res}$ can be defined as the center of the desired test frequency range to allow for the widest range of signal detection. In the illustrated embodiment, the resonant frequency $f_{res}$ includes 10 MHz, 20 MHz, 45 MHz, 100 MHz, 500 MHz, 1 GHz, 5 GHz, 10 GHz, 30 GHz, 50 GHz, 100 GHz, 500 GHz, 1,000 GHz or frequencies ranging therebetween.

During measurement, the solution 176e is applied over one or more of the open-circuited stubs 172. A MBR 176d is formed when one or molecules within the solution bind to the interface transmission line 176a. In this instance, the MBR 176d and the solution electrically behave as a parasitic circuit, further described below, which causes the resonant frequency point $f_{res}$ to shift above or below its original resonant frequency point. This shift in frequency can be detected, and is used to indicate the occurrence of a molecular binding event. The signal response may also be interrogated over a wide spectrum to ascertain the identity of the bound molecular structure, as described below. Each resonant circuit 170 may be fabricated to bind different molecular structures and each resonant circuit 170 be made addressable, thereby permitting simultaneous detection and identification of a large numbers of molecular structures within the same solution. In an alternative embodiment, each resonant circuit 170 may be designed to exhibit a distinct resonant frequency, in which case all of the resonant circuits 170 may be interrogated over a continuous frequency spectrum to determine molecular binding.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

C. Transmission Line and MBR

The binding interactions of the system generally occurs within the bio-assay device, and in particular along the conductive layer (interface transmission line in FIGS. 1A–1C). The conductive layer is fabricated from materials having a morphology which is conducive to support the propagation of the high frequency test signal. The conductive surface is constructed from materials exhibiting appropriate conductivity over the desired test frequency range as well as possessing good molecular binding qualities as described above. Such materials include, but are not limited to gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. The conductive layer may also be formed from semiconducting materials which may be either crystalline or amorphous in structure, including chemically doped or pure carbon, silicon, germanium, gallium-arsenide, idium-gallium arsenide, or the like. The conductive material may also be formed from polymers especially those that are conductive such as polyacetylene, polythiophene and the like. The conductive layer may be thick or only several molecular layers in depth as the application requires. The conductive layer may be comprised of an evaporated thin metal layer or an epitaxial layer of gallium arsenide or other semiconductor materials rendered conductive through known semiconductor processing techniques. In addition, the conductive layer may be derivatized, the process by which is well known, e.g., see Kumar et al., "Patterned Self-Assembled Monolayer and Mesoscale Phenomena," *Accounts of Chemical Research*, 28:219–226 (1995).

The conductive layer is additionally fabricated from materials having a morphology which is conducive to molecular binding. Ligands may bind directly, indirectly through other molecular structures, or through both configurations to bind to the conductive layer. The range of molecules that may bind to the conductive layer include, but are not limited to, proteins, nucleic acids, small molecules, saccharides, lipids, and any other molecule of interest. The chemistry may involve only a single species of molecules attached to the surface, a whole array of different species attached to the surface, or multiple binding events between species directly attached to the surface and ligands of interest in the solution.

The typical chemistry involved in attaching a ligand to the conductive layer will in general depend on the nature of the ligand and any antiligand to which it binds, and their functions in the assay. A list of possible types of interactions that may occur on the surface include but are not limited to: protein/protein interactions, DNA/protein interactions, RNA/protein interactions, nucleic acid hybridization, including base pair mismatch analysis, RNA/RNA interactions, tRNA interactions, enzyme/substrate systems, antigen/antibody interactions, small molecule/protein interactions, drug/receptor interactions, membrane/receptor interactions, conformational changes in solid phase ligands, protein/saccharide interactions, and lipid/protein interactions.

In general terms, binding events in one embodiment may be described as primary binding and secondary binding. Additional layers of molecular binding may also occur. Primary binding refers to the attachment of an antiligand to the conductive surface, which can be done through the assistance of a linker molecule. Secondary binding refers to the binding of a ligand to the antiligand, which may be another molecule in the MBR or directly to the conductive surface itself. Typically, the binding involves a liquid phase ligand binding to an immobilized solid phase antiligand. For example, primary binding could be the attachment of a specific antibody to the conductive layer of the bioassay device and secondary binding would involve the binding of a specific antigen in a sample solution to the antibody. Alternatively, secondary binding may be the direct attachment of a protein to the conductive surface, such as the amine terminus of a protein attaching directly to a gold conductive layer.

Figure 1D:
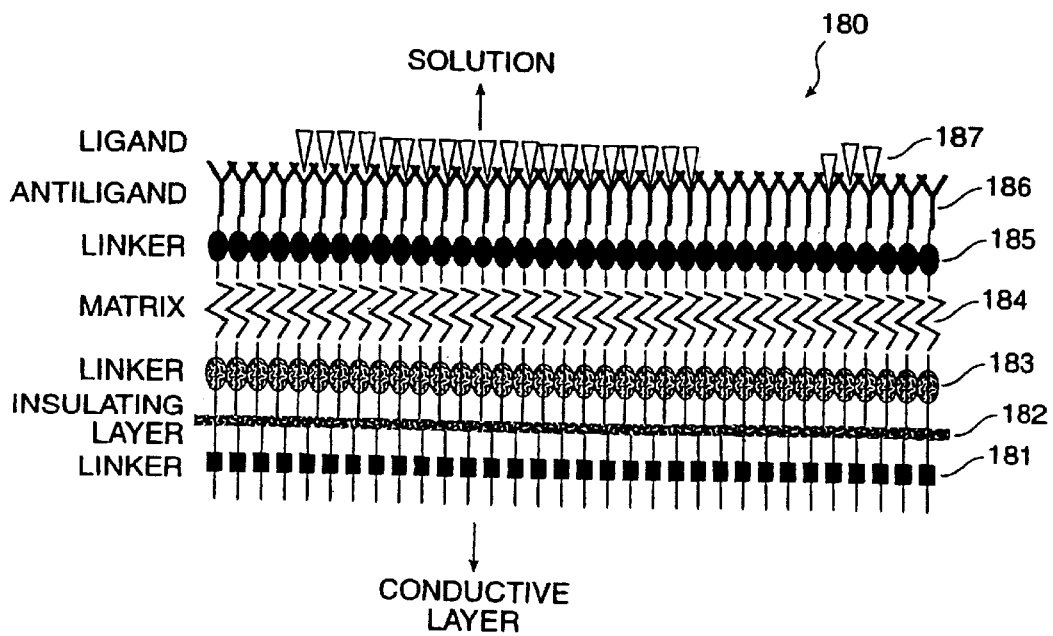
FIG. 1D illustrates one embodiment of a molecular binding region in accordance with the present invention.

The aforementioned binding results in the formation of a molecular binding region (MBR) 180 along one or more areas of the conductive layer, one embodiment of which is illustrated in FIG. 1D. In this embodiment, the MBR 180 optionally consists of a first linker 181, an insulator 182, a second linker 183, a matrix 184, a third linker 185, an antiligand layer 186, and a ligand layer 187.

First linker 181 provides attachment between insulating layer 182 and conductive layer (not shown). First linker 181 consists of molecule such as thiols, amines, amides, or metals such as chromium or titanium. Insulating layer 182 provides a barrier between the conductive layer and the MBR 180 and solution (not shown). Insulating layer 182 may provide a hermetic barrier to prevent structural deterioration of conductive layer due to exposure to the MBR and/or solution. Alternatively, or in addition, insulating layer 182 may consist of an electrically non-conductive material to prevent the flow of DC or low frequency energy from the conductive layer to the MBR and/or solution which could interfere with the measurement. The insulating layer may include polyimide, alumina, diamond, sapphire, non-conductive polymers, semiconductor insulating material such as silicon dioxide or gallium arsenide or other materials which provide hermetic and/or electrically insulating characteristics. The insulating layer may also consist of air, or another gaseous substance, in which case linker 181 may be deleted.

Second linker 183 provides attachment between the insulating layer 182 and matrix 184 and consists of the same or similar molecules as first linkers 181. Matrix layer 184 may consist of a polymer layer, but is also optionally a carbohydrate, protein, poly-amino acid layer or the like. Third linker 185 consists of molecules suitable for attaching the matrix layer to the antiligand 186 and may consist of the same or similar molecules as either first and/or second linkers 181 and 183.

Antiligand 186 is used to specifically or non-specifically bind the ligand 187 within solution and/or to measure physical properties of the solution, some examples of which are temperature, pH, ionic strength, and the like. Antiligand consists of a molecule or molecular structure which specifically or nonspecifically binds to ligand 187.

For instance, in the case in which the ligand consists of an antigen, antiligand 186 will consist of an antibody. Ligand 187 consists of a molecule or structure which specifically or nonspecifically binds to the antiligand 186.

Generally, the MBR will be sufficient to interact measurably as described herein with an electromagnetic test signal along the associated signal path. Thus, essentially any MBR composition that exhibits varying dielectric properties can be analyzed. In most embodiments, the MBR will range in thickness between about 1–5 Å to 1 cm. For simple molecular binding events, the range will usually be between about 10 Å to 10,000 Å, typically between 100 Å and 5,000 Å, or 500 Å to 1,000 Å. In larger interactions (e.g., cellular) the MBR will range between 1 $\mu$m and 100 $\mu$m, preferably 5 $\mu$m to 50 $\mu$m. With insulators, matrices and the like, the size will range significantly higher.

The embodiment of FIG. 1D is not intended to be exhaustive of all possible MBR configurations. Those of skill in the art will appreciate that a vast multiplicity of combinations making up the MBR can be designed, as dictated by the specific applications. For instance, in another embodiment first, second and third linkers 181, 183, 185, insulating layer 182, and matrix layer 184 are not utilized, such that the MBR consists of antiligand 186 and ligand 187. Further alternatively, first linker 181 and insulating layer 182 may be deleted. Other alternative embodiments in which one or more of the described layers are deleted, or additional layers added, will be apparent to one skilled in the art.

Figure 1E:
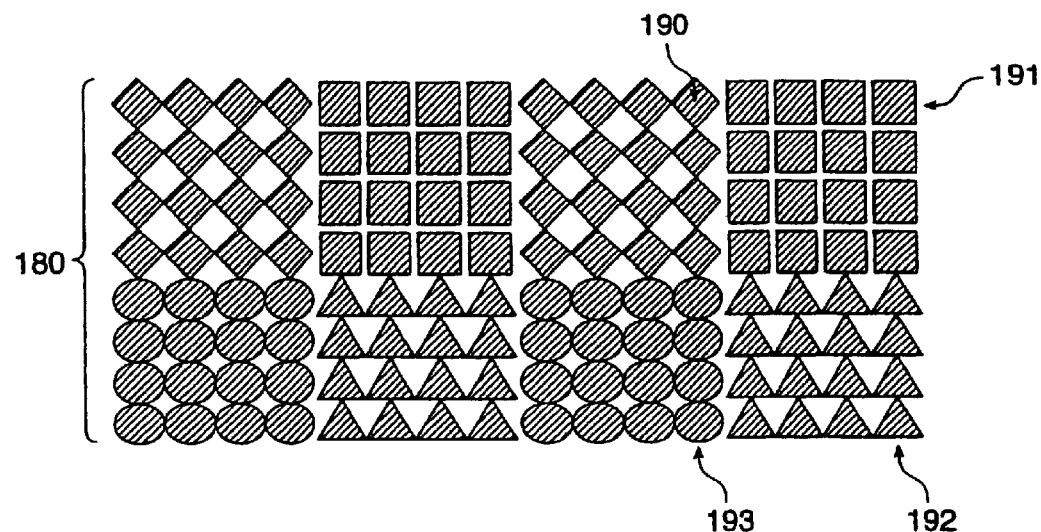
FIG. 1E illustrates one embodiment of a molecular binding region having multiple antiligands which are spatially separated in accordance with the present invention.
Figure 1F:
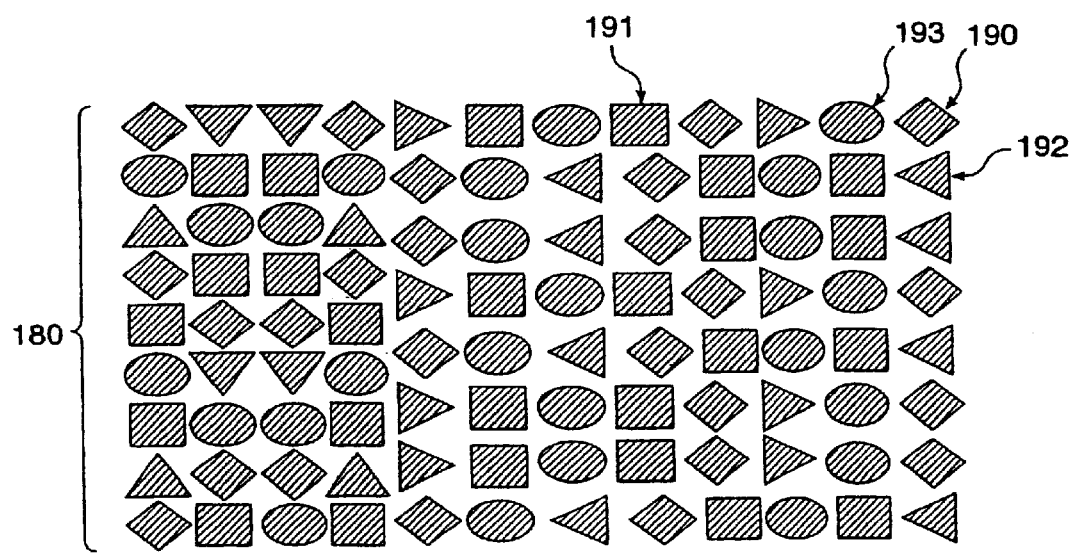
FIG. 1F illustrates one embodiment of a molecular binding region having multiple classes of antiligands in accordance with the present invention.
Figure 1G:
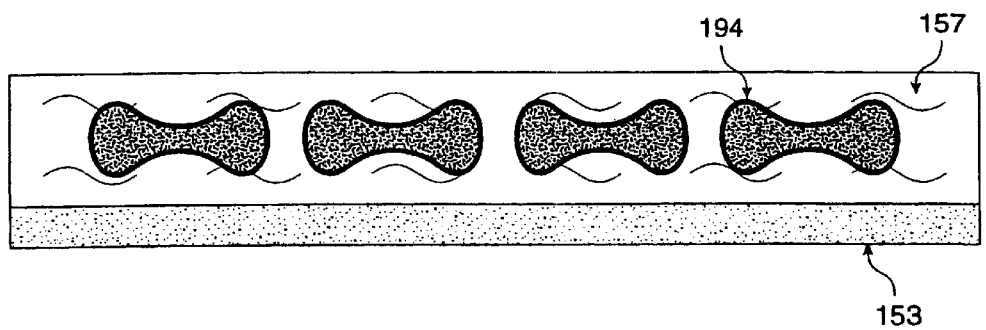
FIG. 1G illustrates a molecular binding region comprising one or more cells in accordance with the present invention.
Figure 1H:
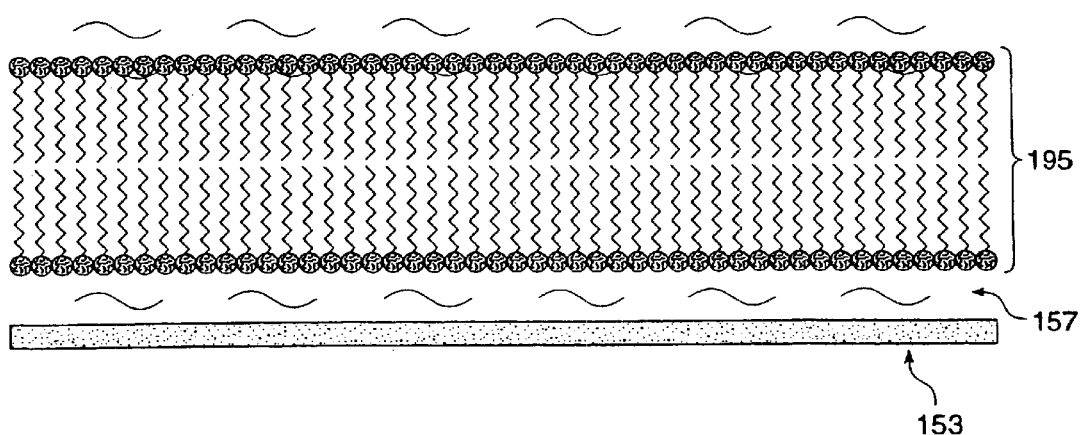
FIG. 1H illustrates a molecular binding region comprising cell membranes and membrane associated structures in accordance with the present invention.

Further, the MBR may be composed of heterogeneous molecules which may be spatially grouped or randomly layered or distributed depending upon the particular array format. For example, FIG. 1E illustrates a top view of an MBR 180 having four different antiligands 190, 191, 192 and 193, which are spatially separated. FIG. 1F illustrates an MBR 180 in which four different antiligands 190, 191, 192 and 193 are randomly distributed throughout. In another embodiment, FIG. 1G illustrates a cross-sectional view in which the MBR 180 contains cells 194 in solution 157 coupled to signal path 153. In another embodiment, a cell membrane 195, with membrane bound structures (not shown), is in solution 157 coupled to the interface transmission line 53. The layers may include for example, linkers, matrices, antiligands, ligands and one or more insulating layers. In some embodiments, one or more membranes may be employed, such as those controlling ion transport, size or charge selection or supporting the attachment of antiligand or other molecular structures.

Electrically, the MBR exhibits unique dielectric properties which are in part attributable to the structural and conformational properties, and changes therein, of bound molecules, both isolated and in the presence of environmental changes such as binding events, pH changes, temperature, ionic strength and the like. The dielectric properties of the bound molecular structures, along with the local structures of the solvating medium (the solution) may also be attributable to changes in the intramolecular and intermolecular bonds caused by primary or other higher-order binding, and the displacement of the solvating medium near the conductive layer.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

III. The Bio-Assay Device
A. Device Structure

Structurally, the bio-assay device includes a signal path and a bio-electrical interface. The signal path may consist of a single input/output signal port, one input signal port path and one output port path, or multiple input and/or output signal port paths. The signal path(s) may be realized in a number of different architectures, such as a conductive wire, a transmission line, a waveguide structure, resonant cavity, or any other transmission medium that will support the propagation of the test signal over the desired frequency range. For possible embodiments, see R. E. Collins *Foundations for Microwave Engineering*, McGraw-Hill Publishing Co., 1966; and S. March, *Microwave Transmission Lines and Their Physical Realizations*, Les Besser and Associates, Inc., 1986. Further, the bio-assay device may also be realized in a variety of different configurations. Non-exhaustive configurations include large to miniaturized structures using conventional manufacturing techniques, conventional etching and photolithography, or semiconductor processing techniques.

Figure 2A:
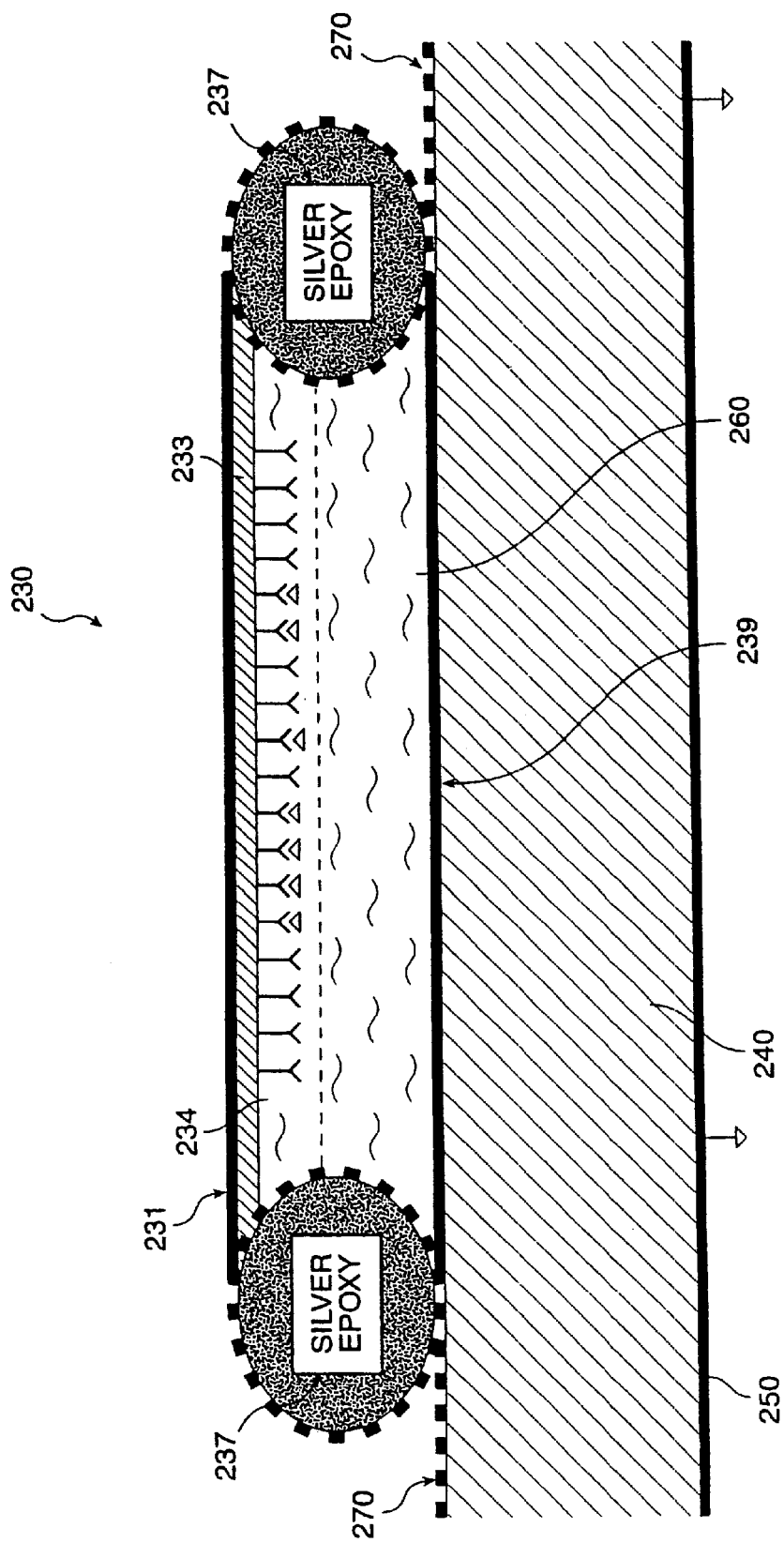
FIG. 2A illustrates one embodiment of the bio-assay device in accordance with the present invention.

FIG. 2A illustrates one embodiment of the bio-assay device as shown in cross-sectional view. The bio-assay device 230 consists of a top plate 231, contact terminals 237, and a bottom plate 239. Top plate 231 includes a bottom surface having an interface transmission line 233 disposed thereon. The dielectric substrate 240 and the ground plane 250 are located external to the bio-assay device. Top plate 231 and/or dielectric substrate 240 are formed from an insulating material, such as glass, which are preferably compatible with conventional photolithography or gold sputtering, etching or chemical vapor deposition (CVD) processing. Other materials such as alumina, silicon, gallium arsenide or other insulating materials, may alternatively be used.

As illustrated in FIG. 2A, the bottom surface of the interface transmission line 233 is in contact with the molecular binding region (MBR) 234. As illustrated, the MBR may consist of bound molecular structures of different layers or types as well as molecular structures occurring within the solution. In alternative embodiments, the MBR 234 may extend over small or large portions of the interface transmission line 233 and may consist of different bound molecular structures as shown. The MBR may consist solely of antiligand/ligand structures, or a variety intermediate of linker, matrix, and insulating layers, as shown in FIG. 1D. When implemented, the insulating layer 182 (FIG. 1D) may consist of air, polyimide, alumina, diamond, sapphire, or semiconductor insulating material such as silicon dioxide or gallium arsenide or a non-conductive material in addition to other conventional insulating materials. The thickness and dielectric constant of the insulating layer are such that the MBR 234 and the interface transmission line 233 are tightly coupled together during signal transmission. The thickness of the insulating layer 182 may be $10^{-1}$m, $10^{-2}$cm, $10^{-3}$m, $10^{-4}$, $10^{-5}$m, $10^{-6}$ m, $10^{-7}$m, $10^{-8}$ m, $10^{-9}$m, $10^{-10}$ m or less in thickness, or values ranging therebetween, depending the amount of coupling required, the dielectric constant of the insulating layer, and the total coupling area. Coupling may be accomplished through a number of different configurations, including broadside and offset coupled configurations in multi-layer, coplanar, or waveguide circuit topologies. Implementing an insulating layer may be advantageous for hermetically sealing the interface transmission line from the solution medium and/or for preventing DC or low frequency current from flowing into the solution which could possibly disrupt molecular binding events occurring therein.

The interface transmission line 233 consists of a material which is capable of supporting signal propagation and which is capable of binding the MBR 234. The material will vary depending upon the makeup of the MBR, but some will include gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. Alternatively, the interface transmission line 233 may include one or more molecular structures (antiligands) (which forms a part of the MBR 234) for forming bonds with one or more targeted molecules (ligands). The material comprising the interface transmission line may also be chosen to promote the attachment of linkers as well as to support signal propagation. Other materials that can be used to form the interface transmission line 233 will be readily apparent to those of skill in the art.

The ligands may be transported to the MBR 234 using a solution 260, such as various buffered solutions (e.g., Dulbecco's phosphate-buffered saline (d-PBS).) The ligand of interest such as protein can be applied to the binding surface using a variety of techniques such as wicking, pipeting, dipping, dropping, direct contact through capillary action, or via various fluidic devices.

In a specific embodiment, the interface transmission line 233 is designed to provide low signal loss and close impedance matching to the external transmission lines 270. Low signal loss is achieved by fabricating the interface transmission line 233 from a conductive material, some examples being gold, copper, aluminum, indium tin oxide (ITO) or other conductive materials described above. Close impedance matching is achieved by defining the width of the interface transmission line 233 at approximately the width of external transmission lines 270, depending on the relative dielectric properties of the substrate, the solution, and the MBR. Signal continuity between the interface transmission line 232 and the external transmission lines 270 is provided via contact terminals 237. As explained above, the MBR 234 and solution medium 260 may be located proximate to the ground plane 250 alternatively, or in addition to these layer's location proximate to the interface transmission line 232.

Additional analog and/or digital circuitry in lumped element form, distributed form, or a combination of both may be included at the input and/or output ports of the bio-assay device. For instance, impedance matching circuits and/or buffer amplifier circuits may be employed at the input port. Alternatively, or in addition, impedance matching circuitry and one or more output amplifiers may be implemented to further enhance the output signal. Those of skill in the art of electronics will appreciate that other types of conditioning circuitry may be used in alternative embodiments as well.

Figure 2B:
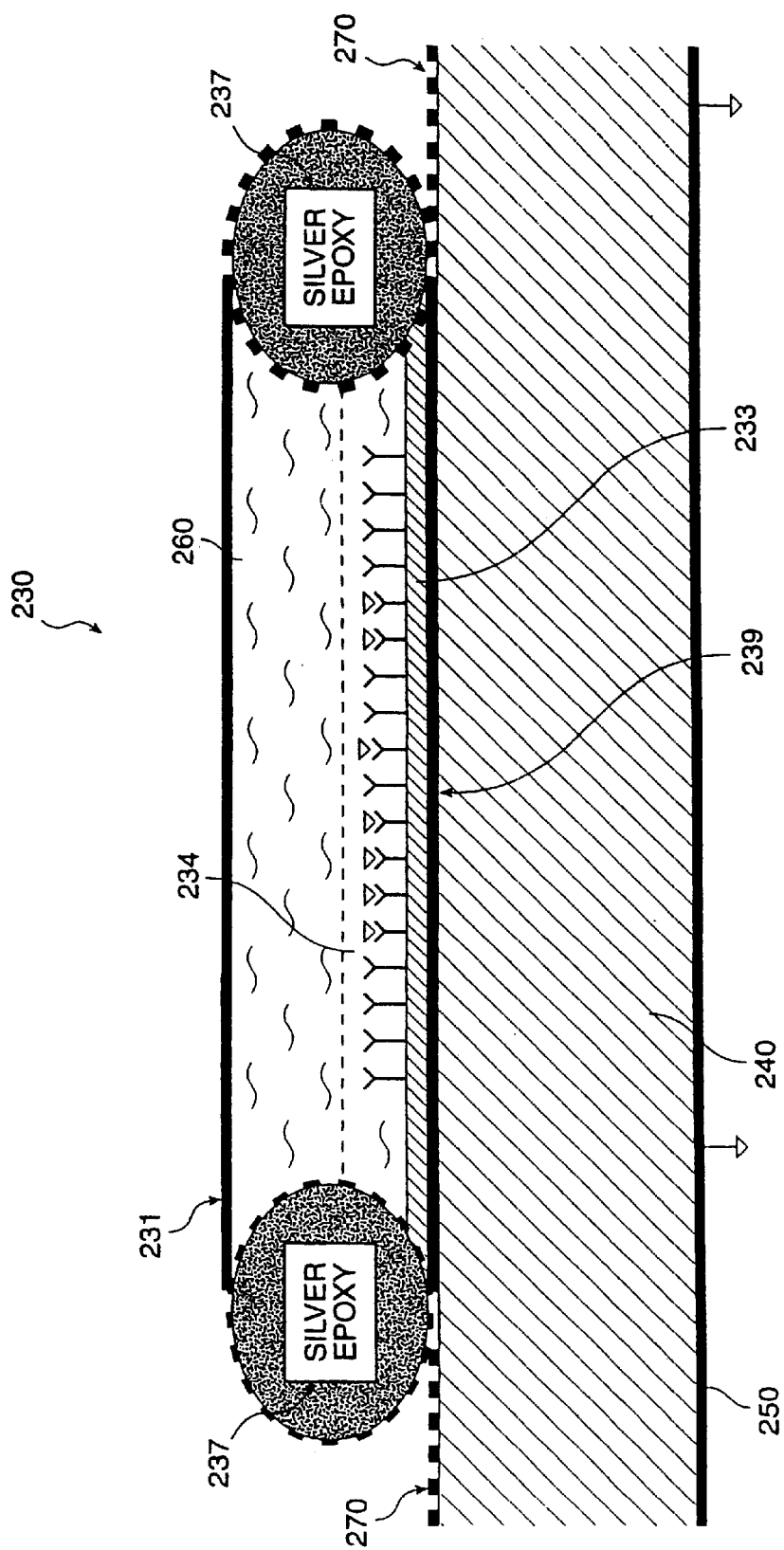
FIG. 2B illustrates a second embodiment of the bio-assay device in accordance with the present invention.

FIG. 2B illustrates a second embodiment of the bio-assay device. In this embodiment, the solution occupies a space above the interface transmission line 233 which is formed on the top surface of bottom plate 239. The top side of the interface transmission line 233 forms the binding surface to which the MBR 234 adheres. Dielectric layer 240 is positioned between interface transmission line 233 and the ground lane 250. Contact terminals 237 provide a signal path to the external transmission lines 270. The interface transmission line, top plate, bottom plate, contact terminals, and dielectric layer may be formed from the materials and the processes as described above. The MBR may also be configured as described above in FIG. 1D, or variations thereof. Further, the MBR 234 and solution medium 260 may be located proximate to the ground plane 250 alternatively, or in addition to these layer's location proximate to the interface transmission line 233.

Figure 2C:
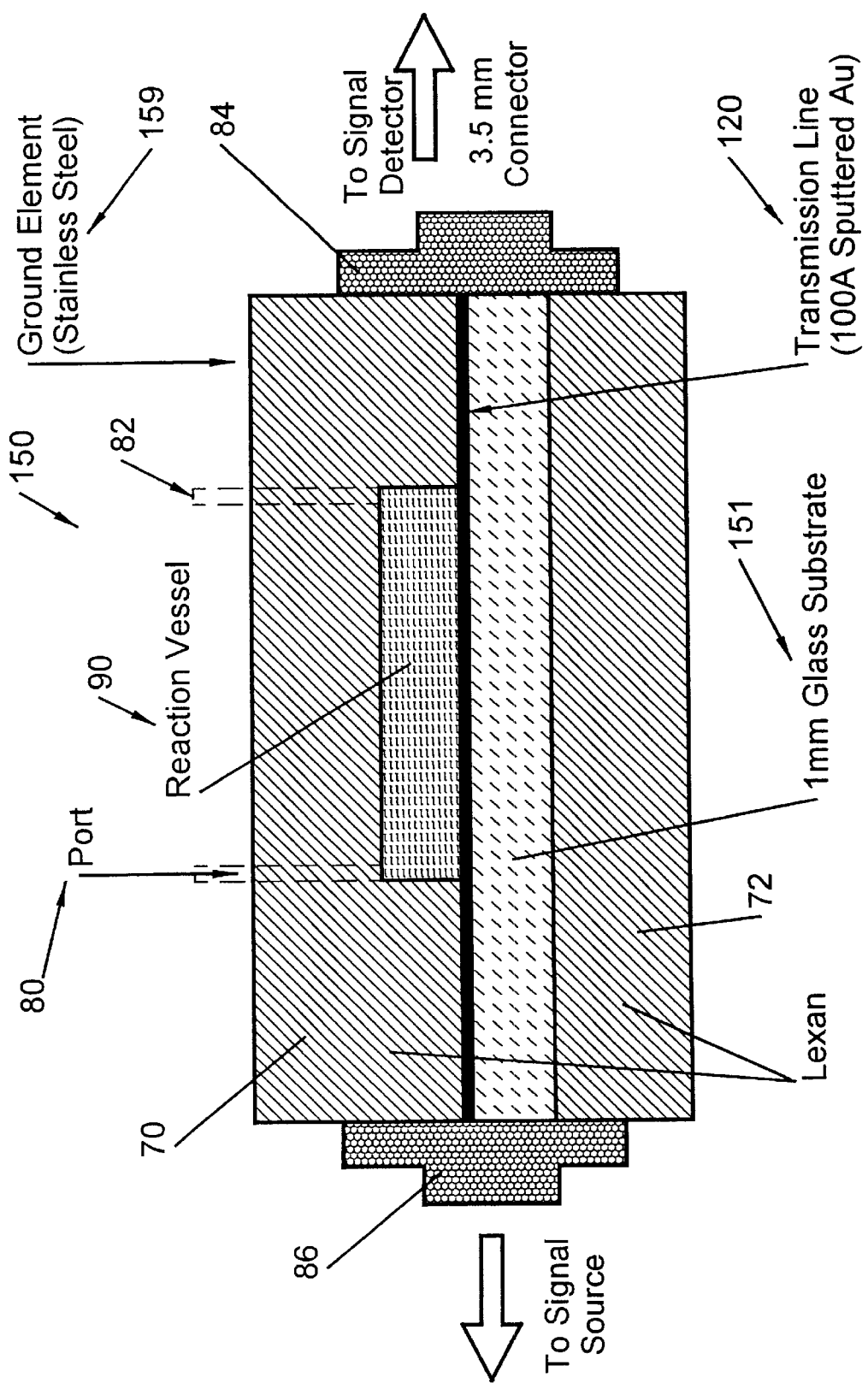
FIG. 2C is a cross-sectional view of a bio-assay device of the present invention.

FIG. 2C depicts a vertical cross-sectional view of another bio-assay device 150 of the present invention. This bio-assay device 150 comprises a two-element stripline configuration similar to that shown in FIG. 1A. The bio-assay device 150 includes a supporting substrate 151 made of glass (approximately 1 mm thick) onto the upper face of which a gold transmission line 120 is sputtered. A reaction vessel 90 (6.0 cm×1.5 cm×0.5 mm) made of LEXAN (a polycarbonate material manufactured by DuPont) is sealed to a section of the transmission line 120. The substrate 151 and attached transmission line 120, together with the reaction vessel 90 attached to the transmission line 120, are sandwiched between an upper and lower layer of a dielectric material 70, 72, respectively. In this particular embodiment, the dielectric material 70, 72, like the reaction vessel, is composed of LEXAN. The dielectric layers or spacers 70, 72 function so as to obtain the desired level of impedance in the system. Thus, other materials capable of achieving a like result can be used in place of LEXAN. In this particular embodiment, the transmission line is designed to give a nominal broadband impedance of 35 Ω, and was 1.5 cm in width, 7.5 cm in length and approximately 100 Angstroms thick.

The subassembly including the glass substrate 151, transmission line 120, reaction vessel 90 and dielectric layers 70, 72 are encased in a stainless steel cover plate which operates as the bio-assay device ground plane 159 to electromagnetically shield the transmission line 120 and provide mechanical support and pressure to keep the bio-assay device 150 sealed. A connector (e.g., a 3.5 mm connector) 84, 86 is attached at each of the two ends of the bio-assay device 150. The center pin of the connectors (not shown) is attached by conductive epoxy (not shown) to the transmission line 120 and substrate 151 with a 50 μ rubber gasket. An inlet and outlet port 80, 82 extend through the cover plate 159, the upper layer of dielectric material 70 and separately connect to the reaction vessel 90, (typically at opposing ends of the reaction vessel 90.) These two ports 80, 82 allow solutions to be flowed into and out of the reaction vessel 90.

The bio-assay device 150 can then be connected via one connector 84 to an analyzer or detector (not shown) capable of measuring S-parameters from 45 MHz to 40 GHz. The other connector 86 is connected to the signal source (not shown).

Additional structural embodiments include bio-assay devices having multi-element transmission lines, waveguides, and resonant cavities, in which the MBR may be attached to one or more of the line or cavity elements in such a way as to enhance detection specificity and sensitivity. Examples of such structures include parallel arranged signal combiners, resonant cavities, or waveguides along which the bound MBR on one element alters the signal propagation properties as compared to another parallel element without the bound structure, and thus serve to change the mode properties of the combined signal, resulting in readily detectable output signal properties. These latter effects make use of well-known techniques to measure frequency, frequency stability, and very small changes in the frequency with ultra-high precision.

B. Binding Surface

Figure 3:
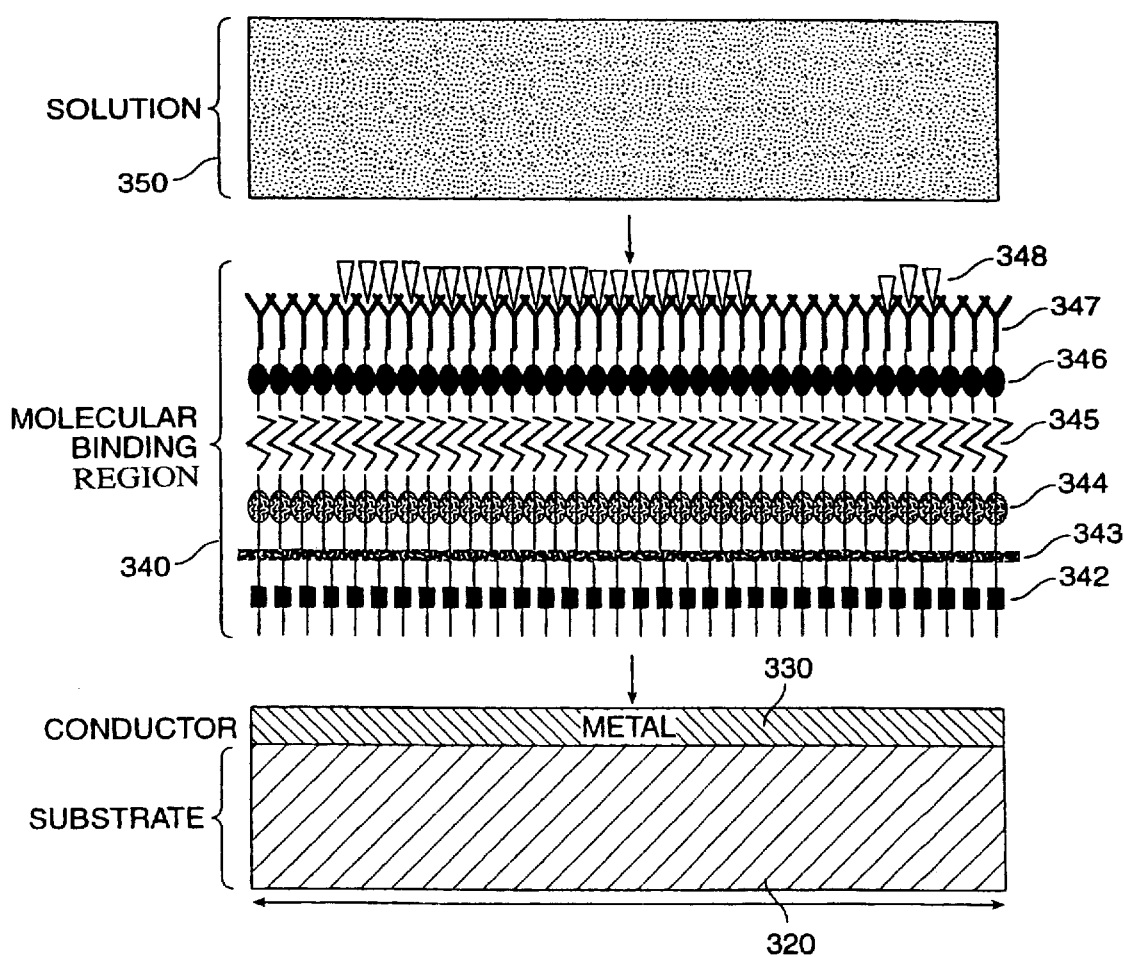
FIG. 3 illustrates one embodiment of the binding surface chemistry which occurs along the conductive layer of the bio-electrical interface.

FIG. 3 illustrates one embodiment of the binding surface chemistry which occurs along the conductive layer of the bio-electrical interface. The bio-electrical interface includes a substrate 320, a conductive layer 330, a MBR 340, and solution 350. The substrate 320 may be any of the dielectric layer or substrate materials described herein including alumina, diamond, sapphire, plastic, glass and the like and may provide structural support to the conductive layer 320. In an alternative embodiment, substrate 320 is removed and structural support is provided via insulating layer 342.

The conductive layer 330 consists of a material having a morphology which promotes signal propagation over the desired frequencies and which promotes binding of the MBR 340, as described above. In a two-conductor circuit topology, conductive layer 330 may comprise the signal plane or the ground plane. In either case however, a second conductive layer (either the signal plane or the ground plane, not shown) is located either below the substrate 320 (the arrangement of FIG. 2B) or at least one substrate layer removed from the solution 350 (an inverted arrangement of FIG. 2A). Alternatively, conductive layers may be positioned at both of these levels.

Solution 350 is coupled to the MBR 340 for permitting the flow of ligands to the MBR 340. Ligand flow from solution 350 to MBR 340 may directionally or non-directional. Solution consists of any transporting medium such as gases, ligius, or solid phase materials, some examples being aqueous d-PBS, Tris buffer, phosphate buffers, and the like.

Along the bio-electrical interface, the MBR is positioned between at least a portion of the solution and the signal path, such that the MBR is more proximate to the signal path than the solution along that portion. In the embodiment of FIG. 3, the MBR 340 is positioned between the solution 350 and the conductive layer 330, closer in proximity to the latter. In one embodiment (shown in FIG. 2A), the solution is positioned between the signal and ground planes. In a second embodiment (shown in FIG. 2B), the solution is positioned outside of the signal-ground plane region.

The MBR may consist of a ligand, ligand/antiligand complex, or other molecular structures as described herein. In this embodiment, the MBR 340 optionally consists of a first linker 342, an insulator 343, a second linker 344, a matrix 345, a third linker 346, an antiligand layer 347, and a ligand layer 348, the function and structure of which is described above in FIG. 1D. Typically, the ligand will be functionally intact, as close to the surface as possible, and the surface density of the antiligand will be high enough to provide the greatest dielectric effect, but not so high as to impair the function of binding, such as by steric hindrance or physically blocking the active binding site of the immobilized antiligand by neighboring molecules.

Ligands may bind specifically or non-specifically either directly to the conductive layer 320 or intermediate structures as shown in FIG. 3. If specifically bound ligands are desired, a linker is optionally used to facilitate the binding, for example to bind all proteins such that conductive layer 320 is exposed to solution. To ensure a densely pack binding layer, thiol groups, Fab, or proteins such as protein A may be used to facilitate the binding of antibodies or other antiligands along the conductive layer 320. Substances may be applied to the conductive layer 320 in a number of ways, including photolithography, semiconductor processing, or any other conventional application techniques.

In addition, some ligands and antiligands may be able to bind in multiple ways. These ligands typically have a statistically predominant mode of binding or may be engineered to bind in a site-specific way. Some antiligands optionally bind the surface in a site-specific manner. For example, an oligonucleotide might be bound at one terminus. Generally, the antiligand will be attached in a manner which will not impair the function of the antiligand, e.g., preferably at concentrations that minimize surface denaturation.

The concentration of the antiligand on the binding surface will vary, depending upon the specific analyte. For example, typical concentrations for proteins are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, or concentrations ranging therebetween. Typical concentrations for nucleic acids are $10^7/cm^2$, $10^8/cm^2$, $10^9/cm^2$, $10^{10}/cm^2$, $10^{11}/cm^2$, $10^{12}/cm^2$, $10^{13}/cm^2$, $10^{14}/cm^2$, $10^{15}/cm^2$, $10^{16}/cm^2$, $10^{17}/cm^2$, $10^{18}/cm^2$, $10^{19}/cm^2$, $10^{20}/cm^2$, or concentrations ranging therebetween Typical concentrations for analytes in whole blood range from 55M, 25M, 10M, 1M, 0.5M, $10^{-1}M$, $10^{-2}M$, $10^{-3}M$, $10^{-4}M$, $10^{-5}M$, $10^{-6}M$, $10^{-7}M$, $10^{-8}M$, $10^{-9}M$, $10^{-10}M$, $10^{-11}M$, $10^{-12}M$, $10^{-13}M$, $10^{-14}M$, $10^{-15}M$, $10^{-16}M$, $10^{-17}M$, $10^{-18}M$, or concentrations ranging therebetween.

Enough ligand should adhere within the MBR to alter the transmission of a signal through the bio-electrical interface. The quantity of ligands adhering to the binding surface may consist of 1, 10, $10^2$, $10^3$, $10^4$, $10^5$, $10^6$, $10^7$, $10^8$, $10^9$, $10^{10}$, $10^{11}$, $10^{12}$, $10^{13}$ or more ligands, as well as any number therebetween depending upon the surface area of the conductive layer. The ligands need not be applied in predefined regions along the conductive layer since the signal responses are determined by inherent dielectric properties of the MBR as opposed to placement on the bio-assay device or chip. The MBR will generally have a surface density for smaller molecules ranging from $10^{10}$ cm$^2$ to $10^{24}$ cm$^2$, typically $10^{15}$ cm$^2$ to $10^{20}$ cm$^2$. The ligand layer may be as thin as 1 layer, but 2, 3, 4, 5 or 10 or more layers are optionally used.

Once a ligand is bound to the conductive layer, the chemistry and/or structural biology of the system comes into play. The ligand's dielectric properties yield a signal response which is characteristic of the bound structure(s), thereby permitting binding event detection, as well as detection of other properties of interest in the structure. The unique response provided by the binding event will depend on the imrnobilized antiligand, its target ligand, and the rearrangement of the nearby solution molecules (such as water and free ions). The range of molecules that can bind to the surface include but are not limited to proteins, nucleic acids, small molecules, saccharides, lipids, and any other molecule of interest.

Typically, the molecules of the MBR are disposed within a solution which may consist of an aqueous solution of water, d-PBS, Tris, blood, physiological buffer, cerebrospinal fluid, urine, sweat, saliva, other bodily secretions, organic solvents, and the like. Other solutions may include gases, emulsions, gels, and organic and inorganic compounds.

The secondary binding reaction occurs at the MBR of the bio-assay device. A ligand in a solution is transported across the bio-assay device such that it contacts the antiligand of the binding layer. The concentration of the ligand in the solution varies and may consist of $10^{-1}$ M, $10^{-2}$ M, $10^{-3}$ M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, $10^{-16}$ M, $10^{-17}$ M, $10^{-18}$ M, $10^{-19}$ M, $10^{-20}$ M, M. When an interaction, such as binding, occurs between the ligand and the antiligand, the ligand, then optionally becomes part of the binding layer, as dictated by the chemical equilibrium characteristics of the binding event.

The MBR includes the bound ligands and may also include solution molecules. The bound ligands can be any molecule, including proteins, carbohydrates, lipids, nucleic acids, and all other molecules discussed herein. The MBR may further include a linker to aid in the binding of the antiligand to the binding surface layer.

Additionally, the interaction of the antiligand with the ligand changes the characteristic dielectric response of the binding layer with only the antiligand attached. For example, if antiligand A is the antiligand that forms the binding layer, the dielectric response of a test signal propagating along the transmission line will reflect the characteristic properties of the structure of antiligand A. When ligand B binds to antiligand A, the structure and/or dielectric properties of the binding layer will change due to the binding of A to B. The structure of A may change as B binds to it, thus providing a different signal response. The change in signal due to the binding interaction will be characteristic of the binding of A to B. Therefore, the presence of a binding interaction can be determined from the change in the signal.

Moreover, information about the type of bond or the structural and/or conformational changes upon binding is obtained by noting which parts of the signal response have changed due to the interaction. Ligand B is optionally detected and identified by the signal change upon its binding to antiligand A. The binding of ligand B to antiligand A induces a conformational change, or other change in the molecular structure or surrounding solution, in antiligand A and its environs. These changes alter the dielectric properties of the MBR, thereby altering the signal response of the test signal propagating along the signal path. The change in the test signal can be used to detect the ligand B binding event and the particulars of the change can be used to identify the ligand B. In as much as the relationship between structure and function of the molecule is known, for example in the case of enzymes, antibodies, receptors and the like, the function of the bound ligand can be deduced from its spectral identification.

In one embodiment, one type of antiligand is applied to the binding surface to form a MBR, and a ligand is applied across the MBR to detect a binding event between the two molecules. For example, the antiligand can be a target protein and the ligand can be any of a variety of compounds, for example, a molecule from a library, a hormone, a nucleic acid, etc. In another embodiment, the antiligand may be a mixture and the ligand that is applied across the binding layer is a known analyte. By detecting specific changes in the signal response, the particular ligand with which the antiligand interacted can be determined due to conformational and other changes induced in the ligand or antiligand, and the spectral response resulting therefrom. Such an embodiment does not require the spatial isolation of each of the specific antiligands, but rather derives the desired level of specificity from the spectral response, so that a given binding interaction is determined by looking at the electromagnetic response rather that noting on which part of the assay the binding event took place.

In another embodiment, the antiligand may be a known molecule on the binding layer and the ligand applied across the bio-assay device as a mixture of unknowns. In this case, the presence of a particular ligand is detected by the presence or absence of a particular peak or signal in the spectrum that results from passing a signal through the bio-assay device. Alternatively, the ligand can be detected due to the changes in the spectrum of the antiligand or ligand upon binding of the ligand. Such an embodiment increases the specificity of the detection over that of the binding chemistry alone, since the signal contains information about the nature of the binding event. Thus, specific binding may be distinguished over non-specific binding, and the overall specificity of detection may be greatly improved over the specificity of the chemistry alone.

The system of detection formed through use of the bioassay device provides a high throughput detection system because detection optionally occurs in real time and many samples can be rapidly analyzed. The response period is optionally monitored on a nanosecond time scale. As soon as the molecules are bound to each other, detection occurs. More time is optionally required to measure low concentrations or binding events between molecules with a low binding affinity. The actual time is optionally limited by diffusion rates. Other than these potential limitations, thousands of compounds are optionally run through the system very quickly, for example, in an hour. For example, using chip fabrication technologies, a 10,000 channel device (using some of the emerging microfluidics technologies) is possible, and with small volumes and thus short diffusion times, and kinetic measurements measuring only the beginning of the reaction, 10 million samples per hour are optionally measured. With known concentrations, the binding affinity is optionally calculated from the kinetics alone and thus the device can be probed at a very fast time scale and the affinity calculated and/or estimated from the slope of the kinetic curve. References for kinetics and affinities can be found in any standard biochemistry or chemistry text such as Mathews and van Holde, *Biochemistry*, Benjamin Cummings, N.Y., 1990.

C. Bio-Electrical Interface

The bio-electrical interface is the structure along which the MBR and the signal path are formed. As described above, the signal path may consist of a conductive or dielectric waveguide structure, a two conductor structure such as a conventional signal/ground plane structure, or three or more conductor structures known in the art. Generally, the thickness of the conductive region of the signal path is designed to provide minimal signal loss. For example, a typical thickness of gold transmission line is in the order of 0.1 to 1000 $\mu$m, preferably about 1–10 $\mu$m.

The signal path is formed along a direction which is non-orthogonal to the MBR. In one embodiment, the test signal propagates in parallel to a tangent on the surface on which the MBR is formed. In other embodiments, the test signal may propagate at an angle of ±1°, ±2°, ±3°, ±4°, ±5°, ±10°, ±15°, ±20°, ±30°, ±40°, ±45°, ±50°, ±60°, ±70°, ±80°, or ±85° relative to the MBR binding surface, or any ranges therebetween. In a first embodiment, the signal path consists of a transmission line in a two conductor structure and the direction of the signal path is defined by the Poynting vector as known in the art of electromagnetics. In a second embodiment, the transmission line may consist of a conductive region or layer which extends continuously along the bio-electrical interface region. In a third embodiment, the signal path maybe defined as the path having the least amount of signal loss along the bio-electrical interface over the desired frequency range of operation. In a fourth embodiment, the signal path maybe defined as having an a.c. conductivity of greater than 3 mhos/m, i.e., having a conductivity greater than that a saline solution, typically greater than 5 mhos/m, but ideally in the range of 100 to 1000 mhos/m and greater.

Thus, certain methods of the present invention involve placing a ligand or antiligand such as a protein, for example, so that it is coupled to a signal path. In such methods, the signal transmitted along the signal path need not pass through solution, for example from one electrical contact to another. This is important because, as described more fully below, aqueous solutions significantly attenuates electromagnetic signals that pass through water, thereby greatly reducing the sensitivity of such methods.

The bio-electrical interface region consists of a signal path designed to support the propagation of an electromagnetic signal at the desired test frequency. Many configurations are possible, one example being a sputtered gold transmission line operable between D.C. and 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

Additional details regarding the operation of the bio-electrical interface are set forth in copending and commonly owned U.S. application Ser. No. 09/243,194, filed Feb. 1, 1999, which has been previously incorporated herein by reference for all purposes.

IV. Measurement Methodology

A. General Overview

The measurement methodology of the present invention makes use of the observation that a vast number of molecules are distinguishable from one another based upon their unique dielectric properties which include dispersion effects, resonance effects, and effects on the solution surrounding said molecules. In the present invention, when a test signal couples to the MBR, the MBR interacts with the energy of the test signal, resulting in a unique signal response. The unique signal response can then be used to detect and identify the molecules which make up the MBR.

Those of skill in the art will appreciate that most molecules exhibit variation in dielectric properties over different frequencies. For instance, a molecule may exhibit a dramatic change in its dielectric properties as a function of frequency in one or more regions of the electromagnetic spectrum. The frequency band over which the molecule exhibits a dramatic dielectric change is often referred to as the molecule's dispersion regime. Over these regimes, the molecule's dielectric constant, permittivity, dipole and/or multipole moments, and susceptibility will change dramatically as a function of frequency. These quantities are often complex, having both real and imaginary parts to account for both the magnitude and phase changes that occur in the signal response. The dispersion regimes range over various frequencies, including the RF, microwave, millimeter wave, far-infrared, and infrared frequencies.

The molecule's dielectric properties can be observed by coupling a test signal to the molecule and observing the resulting signal. When the test signal excites the molecule at a frequency within the molecule's dispersion regime, especially at a resonant frequency, the molecule will interact strongly with the signal, and the resulting signal will exhibit dramatic variations in its measured amplitude and phase, thereby generating a unique signal response. This response can be used to detect and identify the bound molecular structure. In addition, because most molecules will exhibit different dispersion properties over the same or different frequency bands, each generates a unique signal response which can be used to identify the molecular structure.

Detection and identification of molecular binding events can be accomplished by detecting and measuring the dielectric properties at the molecular level. The dielectric properties at the molecular level can be defined by the molecule's multipole moments, the potential energy of which can be represented as an infinite series as is known in the art:

$$\Phi(x) = \frac{q}{r} + \frac{p \cdot x}{r^3} + \frac{1}{2}\sum_{i,j} Q_{ij} \frac{x_i x_j}{r^5} + \cdots$$

The infinite series consists of multiple terms, each of which describes in varying degrees the molecule's dielectric properties in the presence of an electric, magnetic or an electromagnetic field. The first term is referred to as the monopole moment and represents the scalar quantity of the electrostatic potential energy arising from the total charge on the molecule. The second term or "dipole moment" is a vector quantity and consists of three degrees of freedom. The third term or "quadrapole moment" is a rank-2 tensor and describes the molecule's response over 9 degrees of freedom. In general, the $N^{th}$ term is a tensor of rank N−1, with $3^{N-1}$ degrees of freedom, though symmetries may reduce the total number of degrees of freedom. As one can appreciate, the higher-order moments provide greater detail about the molecule's dielectric properties and thus reveals more of the molecule's unique dielectric signature. Since the gradient of the potential results in the electric field:

$$E = -\nabla \Phi(x),$$

The field strength of the higher-order moments falls off rapidly as a function of distance and thus their contribution is difficult to measure. For instance, the field due to dipole moment falls off as $r^{-3}$ and the field due to the quadrupole moment falls off as $r^{-4}$. Thus, this approach requires close proximity between the binding molecules and test signal path and low signal loss therebetween. Since it is often the case that molecular binding event detection occurs in strongly signal-absorbing solutions, such as whole blood samples or ionic solutions, signal loss between the binding events and signal path becomes quite high and detection of the higher order moments is very difficult.

In addition, each multipole term couples to the electric field in a different way. This is demonstrated by first looking at the energy of a given electrostatic system:

$$W = \int \rho(x)\Phi(x)d^3x$$

Expanding the electrostatic potential in a Taylor Series gives $$\Phi(x) = \Phi(0) + x \cdot \nabla\Phi(0) + \frac{1}{2}\sum_i\sum_j x_i x_j \frac{\partial^3\Phi(0)}{\partial x_i \partial x_j}$$

Since $E = -\nabla\Phi(x)$, $$\Phi(x) = \Phi(0) - x \cdot E(0) - \frac{1}{2}\sum_i\sum_j x_i x_j \frac{\partial E_j}{\partial x_i}$$

Further, for the external field, $\nabla \cdot E = 0$, so that we get $$\Phi(x) = \Phi(0) - x \cdot E(0) - \frac{1}{6}\sum_i\sum_j (3x_i x_j - r^2 \delta_{ij})\frac{\partial E_j}{\partial x_i}$$

Inserting this back into the equation for the energy given above yields $$W = q\Phi(0) - p \cdot E(0) - \frac{1}{6}\sum_i\sum_j Q_{ij}\frac{\partial E_j}{\partial x_i}$$

This shows the manner in which each multipole term interacts with the interrogating field: The total charge q with the potential, the dipole p with the electric field, the quadrupole $Q_{ij}$ with the gradient of the electric field, etc. This illustrates the second difficulty with the detection of the higher order multipole moments: It is difficult in a bulk sample to achieve sufficient field gradients to couple to the higher order moments.

The present invention overcomes the aforementioned obstacles by implementing the described bio-electrical interface. The interface includes a MBR which is coupled along the signal path. The MBR consists of a very thin and highly inhomogeneous layer (from a dielectric standpoint), thus providing the required proximity to the electromagnetically probing structure as well as the sufficient field gradients to couple to the higher order multipole moments. These qualities enable detection of higher order moments which provide a greatly enhanced view of the molecule's dielectric properties. The positioning of the MBR proximate to the signal and/or ground planes serves to isolate the signal propagating thereon from becoming absorbed into solution, thereby reducing the signal loss and enabling the usage of higher test frequencies to more accurately detect and identify the binding events. In this manner, the present invention enables to a greater degree the recovery or the signal response including the contributions from the molecule's dipole and other higher-order multipole moments.

The ability to detect and measure molecular dipole, quadrupole, and higher order multipole moments in solution represents a significant advance in the art for a number of reasons. First, many molecules of biomedical interest such as proteins have very distinct structures, and therefore distinct multipole moments. Thus identifying the multipole moments for a given molecule reveals properties of said molecule which are unique, and thus allows identification of said molecule. Second, structure and function are intimately related in many molecules of biomedical relevance, such as proteins. Thus, the ability to detect properties of a given molecule which relate directly to the function of said molecule means that functionality may be monitored for whole ranges of activities. Third, the local physiologic environment often plays an important role in the structure and function of a given molecule, so that an ability to detect the physical properties described above means that molecules may be used a monitors and probes for the purpose of measuring changes in a given system. Thus, with the ability to translate complex and informative properties about molecular and cellular systems into a detectable electronic data format, whole new possibilities emerge in the areas discussed herein.

B. Detecting Bound Molecular Structures

The bio-assay device described herein enables the detection of molecular binding events occurring along the signal path. Detectable binding events include primary, secondary, and higher-order binding events. For instance, in a two-conductor bio-electrical interface having no pre-existing MBR, the molecules of the conductive layer will form the antiligands for binding to the ligands, the ligands forming the MBR. In another embodiment, the antiligand and ligand are both included in the MBR. In this embodiment, the MBR is attached to the signal path surface via linkers, matrix molecules, insulating layers or a combination of each as show in FIG. 1D.

Figure 4A:
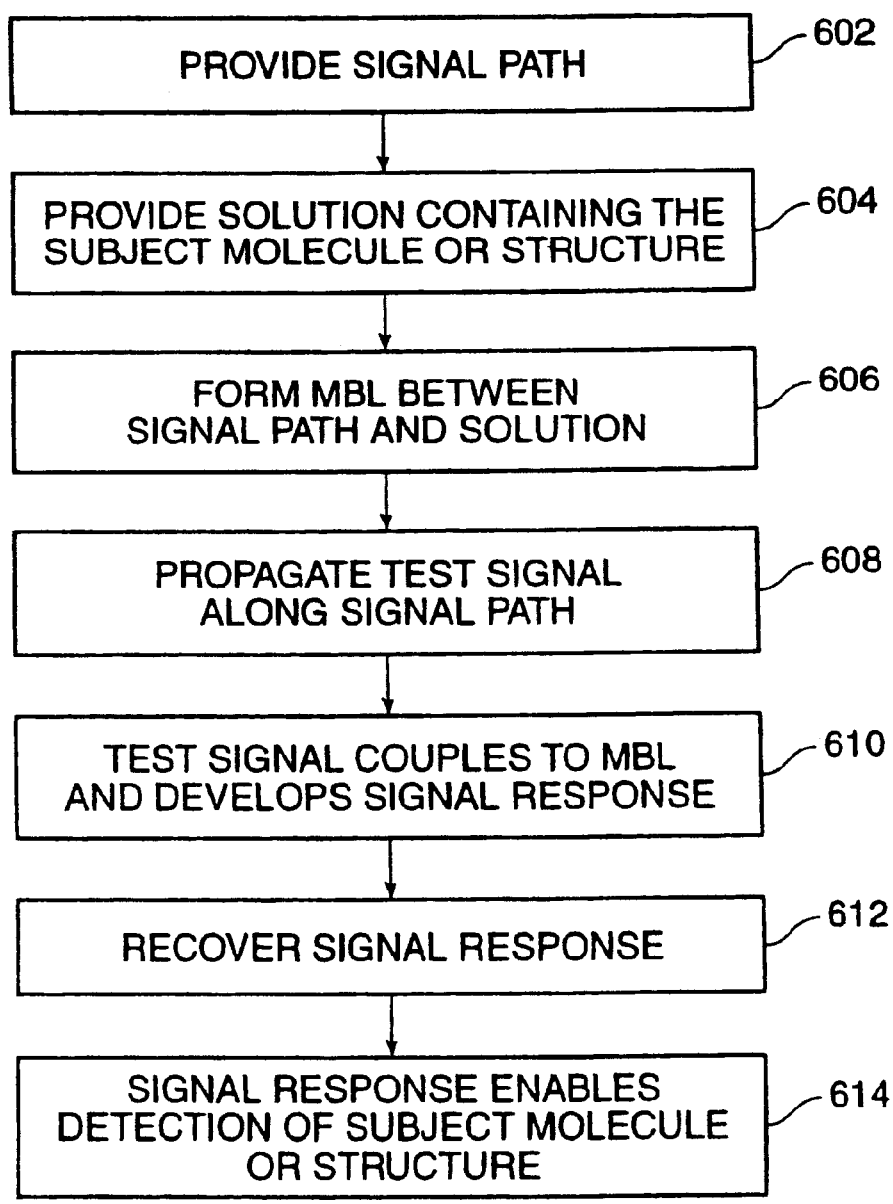
FIG. 4A illustrates one embodiment of a method for detecting molecular binding events in accordance with the present invention.

FIG. 4A illustrates one embodiment of this process. Initially at step 602, a signal path is formed from a material which can support the propagation of a signal over the desired frequency of operation. The signal path may consist of a single port path, a two port path, or a multiple port path within one of the bio-assay devices described herein. In addition, the signal path may be realized as a transmission line, resonant cavity, or as a waveguide structure.

Next at step 604, a solution is provided which contains the subject molecule or molecular structure. At step 606, a MBR consisting of the ligand is formed from the solution and is coupled between at least a portion of the signal path and the solution. Next at step 608, a test signal is propagated along the signal path. Alternatively, the test signal may be launched during the application of the solution in order to observed in real time the signal response occurring as a result of the binding events. At step 610, the test signal propagates over, couples to the MBR and develops a signal response which indicates the presence of the ligand. Next at steps 612 and 614, the test signal is recovered, the response of which indicates detection of the ligand.

The dielectric properties of the MBR may contribute to induce any number of signal responses, each of which may be indicative of molecular binding. For instance, the dispersive properties of the MBR may vary dramatically over frequency. In this instance, the test signal response will exhibit large changes in the amplitude and/or phase response over frequency when molecular binding events occur along the binding surface, thereby providing a means for detecting molecular binding events along the binding surface.

In another embodiment, the dielectric relaxation properties of the MBR will vary as a function of pulse period of the input signal. In this instance, the test signal response will indicate a change in the amount of power absorbed, or change in some other parameter of the test signal like phase or amplitude, at or near a particular pulse period. By observing a change in the absorbed power or other parameters, binding events along the binding surface may be detected. Other quantities such characteristic impedances, propagation speed, amplitude, phase, dispersion, loss, permittivity, susceptibility, frequency, and dielectric constant are also possible indicators of molecular binding events.

The above-described method may be used to detect the primary binding of an antiligand or ligand directly or indirectly along the signal path. Similarly, the process of FIG. 4A may also be used to detect secondary binding of a ligand to an antiligand. The method of FIG. 4A is not limited to detection of primary or secondary binding events occurring along the signal path. Indeed, tertiary, and higher-order binding events occurring either along the signal path or suspended in solution can also be detected using this method.

Figure 4B:
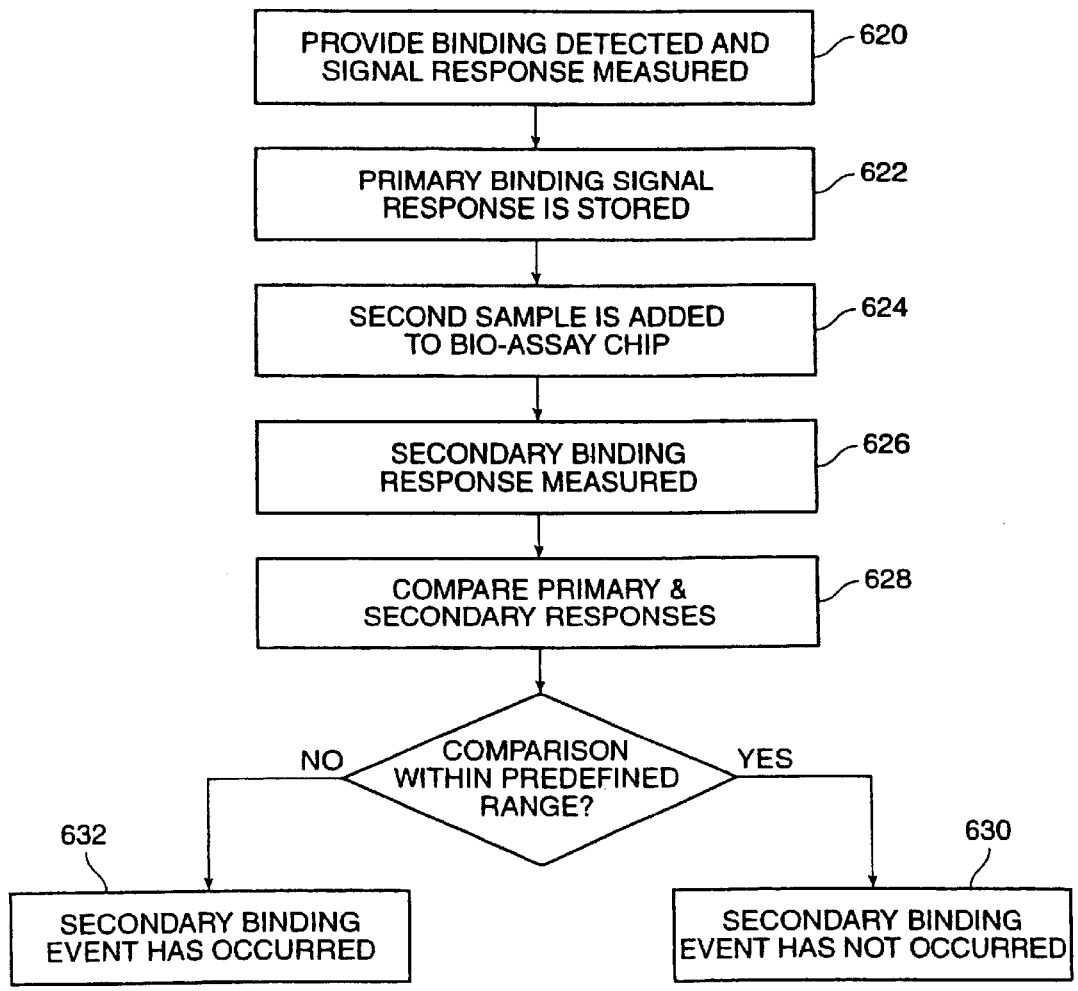
FIG. 4B illustrates one embodiment of a method for detecting secondary and higher-order binding events in accordance with the present invention.

FIG. 4B illustrates a second process for detecting secondary and higher-order binding events occurring either along the signal path. Initially at step 620, the primary binding event is detected and the signal response measured, one embodiment of which is shown in steps 602–612. Subsequently at step 622, the primary binding event signal response is stored and used as a baseline response. Next at step 624, a second molecular solution is added to the bio-assay device and allowed to circulate over the binding surface. Next at step 626, steps 608 through 612 of FIG. 4A are repeated to obtain a second signal response. Next at step 628, the second signal response and the baseline response are compared. Little or no change indicates that the two signal responses are very close, indicating that the structural and dielectric properties of the MBR have not been altered by the addition of the molecules within the new solution. In this case, secondary binding has not occurred to a significant degree (step 630). If the comparison results in a change outside of a predetermined range, the structure and/or dielectric properties of the MBR have been altered, thereby indicating secondary binding events (step 632). Quantities which can be used to indicate secondary binding events will parallel the aforementioned quantities, e.g., amplitude, phase, frequency, dispersion, loss, permittivity, susceptibility, impedance, propagation speed, dielectric constant as well as other factors. Tertiary or high-order binding events may be detected using this approach.

An alternative method of detecting secondary or higher order binding events does not required prior knowledge of the specific primary binding event. In this embodiment, the bio-assay device is designed in the assay development stage to operate with known parameters, so that whenever a pre-defined change in one of these parameters is detected, for example at the point-of-use, the binding event or events are then known to have occurred. In this embodiment, the pre-measurement of a primary binding event is not necessary, as the initial characterization has already been done either at the time of fabrication or at the time of design.

Secondary binding events can also be achieved by detecting changes in the structure of the primary bound molecule. When a molecule becomes bound, it undergoes conformational and other changes in its molecular structure relative to its unbound state. These changes affect the primary binding molecule's dielectric properties as well as inducing changes in the surrounding solution, the variation of which can be detected using steps 620–628 of FIG. 4B, described above.

Quantities which can be monitored to indicate a change in the dielectric properties of the primary bound molecule include the aforementioned quantities, e.g., amplitude, phase, frequency, dispersion, loss, permittivity, susceptibility, impedance, propagation speed, dielectric constant as well as other factors.

C. Detecting Changes in the Dielectric Properties of the Molecular Binding Layer The bio-assay device described herein may also be used to measure the dielectric changes of the MBR as a result changes in temperature, pH, ionic strength and the like.

Figure 4C:
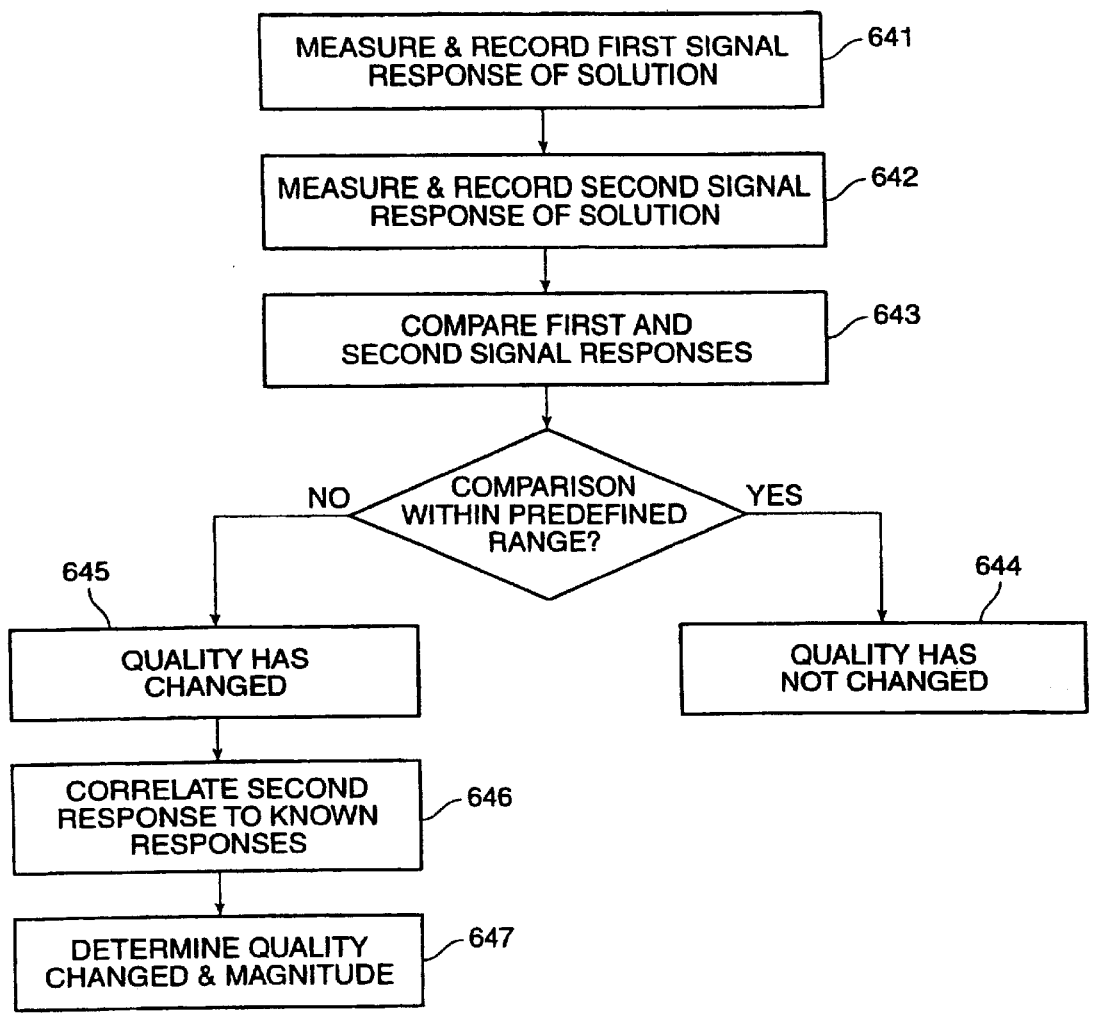
FIG. 4C illustrates one embodiment of a method for measuring dielectric changes of the molecular binding region in accordance with the present invention.

FIG. 4C illustrates an exemplary embodiment of the process. The process closely parallels the disclosed method for identifying binding events, the exception being that the method allows for the detection and quantitation of changes in dielectric properties of the MBR.

The process begins at step 641, when a solution having an initial dielectric property is added to the bio-assay device, the signal response is measured and recorded. In one embodiment, this step is performed according to steps 602–612. After a predetermined time or operation, a second measurement is made and a second signal response is recorded (step 642), again in one embodiment according to steps 602–612. At step 643, a comparison is then made between the first and second signals to determine whether the two signals correlate within a predefined range. If so, the properties of the solution are deemed to not have undergone any dielectric changes (step 644).

If the signal responses do not correlate within a predefined range, one or more dielectric properties of the solution is deemed as having undergone (step 645). Optionally the change in dielectric properties may be quantitated in the following manner. At step 646, the second signal is stored and correlated to a known signal response. The closest correlated response will identify the dielectric property of the solution and the first signal response can be correlated to the initial value of the dielectric property, the difference of which can be used to determine the amount by which the identified dielectric property has been altered (step 647).

D. Identifying Bound Molecular Structures

Figure 4D:
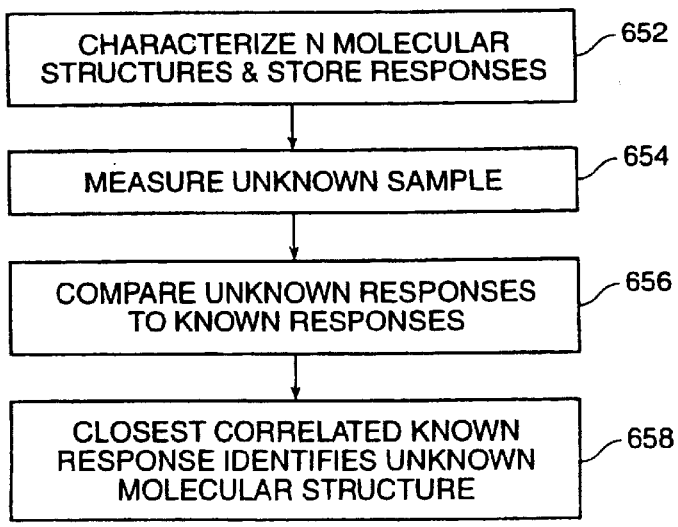
FIG. 4D illustrates one embodiment of a method for identifying a ligand in an unknown solution in accordance with the present invention.

Using the described bio-assay devices, it is possible to characterize a known ligand and subsequently identify it in a solution having an unknown ligand make-up. FIG. 4D illustrates one embodiment of this process. Initially at step 652, a large number of molecular structures are measured and their responses stored using one or more of the measurement systems, described below. In one embodiment, this step is performed according to steps 602–612. Each stored response may correspond to a single ligand occurring within the solution or multiple ligands occurring within the same solution. Subsequently at step 654, a measurement is made of an unknown solution. In one embodiment, this step is performed according to steps 602–612. Next at step 656, the signal response of the solution is compared to the stored signal responses to determine the degree of correlation therewith. At step 658, the unknown molecular structure is identified by selecting the stored response which exhibits the closest correlation to the unknown response. The comparison may be performed using one or more data points to determine the correlation between one or more stored responses, and may involve the use of pattern recognition software or similar means to determine the correlation. The process may be used to identify primary, secondary or higher-order bound molecular structures.

E. Identifying Classes of Bound Molecular Structures

It is also possible to characterize known molecular substructures such as domains or other structural homologies that are common to similar classes of proteins or sequence homologies in nucleic acids. In one embodiment, the process proceeds as shown in FIG. 4D, except that in step 652, N number of molecular sub-structures are measured and their responses stored. Each stored signal response may correspond to one or more sub-structures. The process continues as described in steps 654, 656 and 658 until a sufficient number or structures have been detected and characterized to identify the unknown compound. Once a sufficient number of correlations occur, it is then possible to classify the unknown molecular structure.

Figure 4E:
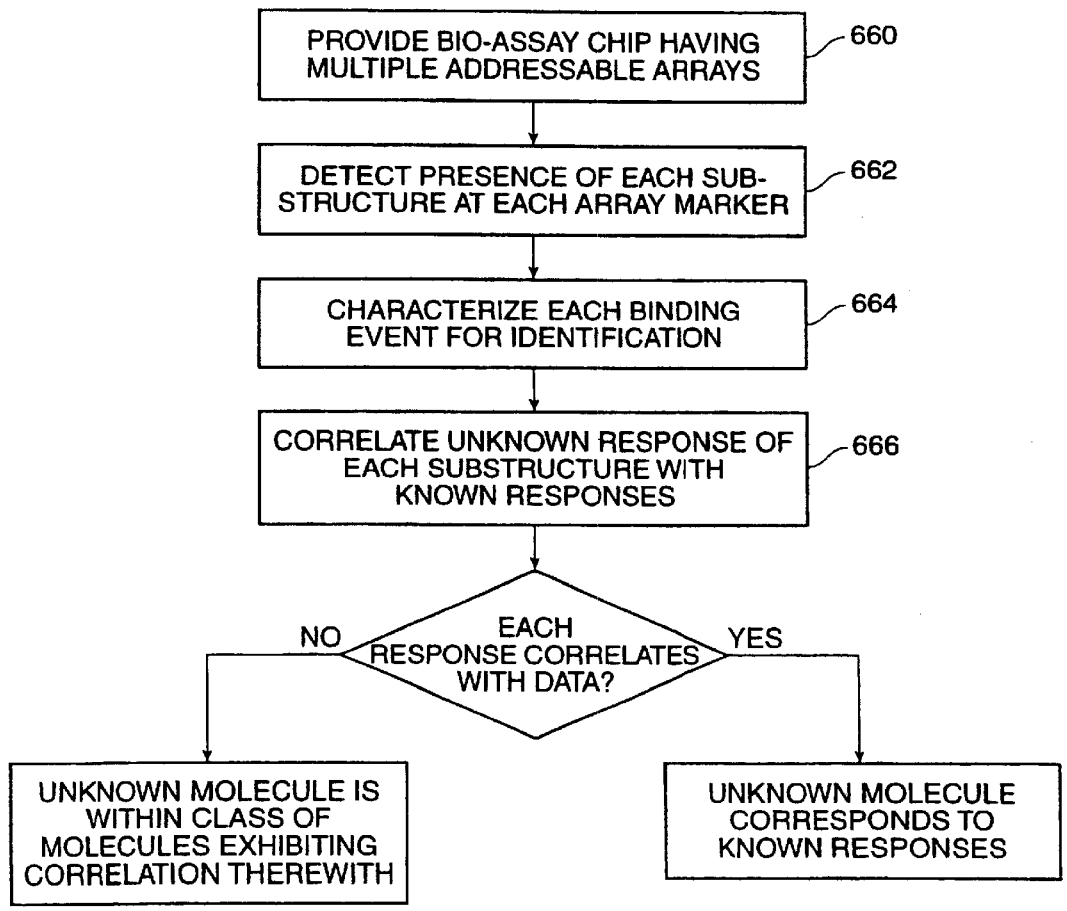
FIG. 4E illustrates one embodiment of a method for identifying the class of a ligand in accordance with the present invention.

FIG. 4E illustrates another process by which unknown ligands may be classified. The process identifies the unknown ligand by detecting binding to structural motifs on the unknown compound. Initially, at step 660 a bio-assay device is provided which has multiple addressable arrays, each of which has a antiligand for a specific ligand substructure. Next at step 662, the presence of particular sub-structures is detected by the binding of each to its respective antiligand, and subsequent characterization. In one embodiment, this step is performed according to steps 602–612. Subsequently at step 664, each of the binding events is then characterized by identification of qualities such as affinity, kinetics, and spectral response. At step 666, a correlation is then made between the known and unknown responses. If each of the unknown responses correlates to known responses, the ligand is identified as the ligand corresponding to the known response. If the sub-structures exhibit both correlated and uncorrelated responses, the correlated responses may be used to construct a more general classification of the unknown ligand. This process may be used to identify any molecular structure, for example proteins, which occur within the same class or have re-occurring structural homologies.

It is also possible that an intensive spectral analysis of a given unknown compound could lead to insights on structure and function, as comparisons can be made to known structures, and extrapolation will lead to some level of classification.

F. Specific v.s. Non-Specific Binding

Specific ligand binding is distinguished form non-specific binding by the spectral "signature" or "profile" of the binding event. A given binding event of interest, for example antibody binding to antigen, may be first characterized in a purified solution containing just the ligand of interest and the antiligand specific to said ligand on the MBR. A broad spectral study is then carried out to see when in the spectrum the strongest responses are found. The assay is then repeated in the solutions typically found in the dedicated applications, for example whole blood, to determine what effects non-specific binding has on the response. Then various points are found which are determinate of specific binding, and a separate set of points are found which are determinate of non-specific binding, and a subset of these frequency points are chosen for the actual assay application. By comparing the response due to specific binding with those due to the non-specific binding, the extent of specific binding can be determined.

G. Characterization of a Given Ligand

Often it is desirable to determine certain qualities of a given molecule. Examples include determining the class to which a protein belongs. This may be done in a number of ways.

Given that the dielectric properties of a given molecule is determined entirely by the geometry of the charge distribution of said molecule, and further given that most proteins have a unique structure or geometry, then each protein may be uniquely determined by measuring the dielectric properties of the protein. Thus a simple dielectric signature, such as the ones generated by the present invention, may serve to uniquely identify a given protein, and further, may allow classification of the protein into some previously known class of proteins.

A further refinement may be added to the classification methodology by using a group of antiligands on the bioassay device which are specific for particular sub-structures of a given protein. For example, a group of antibodies which are specific for particular sub-structures such as domains may be utilized for the determination of the existence or absence of said sub-structures. Thus, any given protein may be characterized by determining both the presence and absence of certain sub-structures as well as the dielectric properties of the protein itself. Further refinements to this classification strategy may include looking at temperature, pH, ionic strength, as well as other environmental effects on the above-mentioned properties In a similar manner, drug-receptor interactions may be characterized to determine the nature of a given binding event, such as whether a given interaction results in the receptor being turned on or off (i.e., whether the drug acts as an agonist or an antagonist), results in some partial agonistic and/or anagonistic effect, or some other form of allosteric effect or non-specific binding. For example, a given receptor may be used as an antiligand, and a known agonist may be used as the first ligand. The interaction is then characterized according to the dielectric response, and this response is saved. Subsequently, compounds which are being screened for drug candidates are then observed with respect to their binding properties with said receptor. A molecule which binds and yields a similar dielectric response is then known to have a similar effect on the receptor as the known agonist, and therefore will have a much higher probability of being an agonist. This paradigm may be used to characterize virtually any type of target-receptor binding event of interest, and represents a significant improvement over current detection strategies which determine only if a binding event has occurred or not.

In cases where no known affinity ligands are available for a given drug receptor (such as orphan receptors), the response of an unknown ligand to said receptor may be compared to drug-receptor binding events in systems with similar structural homologies. For example, G-protein coupled receptors include a large class of receptors with similar structural features and responses, so that an orphan receptor for such a class may be compared to a better-understood G-protein coupled receptor system in order to make a decision as to the nature of a given binding event. Those of skill in the art will readily appreciate that there are many other classes of binding events in which the present invention can be applied.

Proteins are often classified by number and types of structural homologies, or particular substructures which are found in the same or similar classes of proteins. For example, G-Proteins commonly found in cell membranes and which mediate signal transduction pathways between the extra-cellular environment and the intra-cellular environment, always have a structure which traverses the cell membrane seven times. Such a structure is virtually definitive of a G-Protein. Other classes of proteins have similar structural homologies, and as such, any method which can distinguish one class of proteins from another on the bases of these homologies is of enormous use in many of the biomedical research fields.

Examples of sub-structures which may be used in the above method include: Protein secondary and tertiary structures, such as alpha-helices, beta-sheets, triple helices, domains, barrel structures, beta-turns, and various symmetry groups found in quaternary structures such as $C_2$ symmetry, $C_3$ symmetry, $C_4$ symmetry, $D_2$ symmetry, cubic symmetry, and icosahedral symmetry. (G. Rose (1979), Heirarchic Organization of Domains in Globular Proteins, J. Mol. Biol. 134: 447–470).

H. Quantitating Concentrations

Figure 4F:
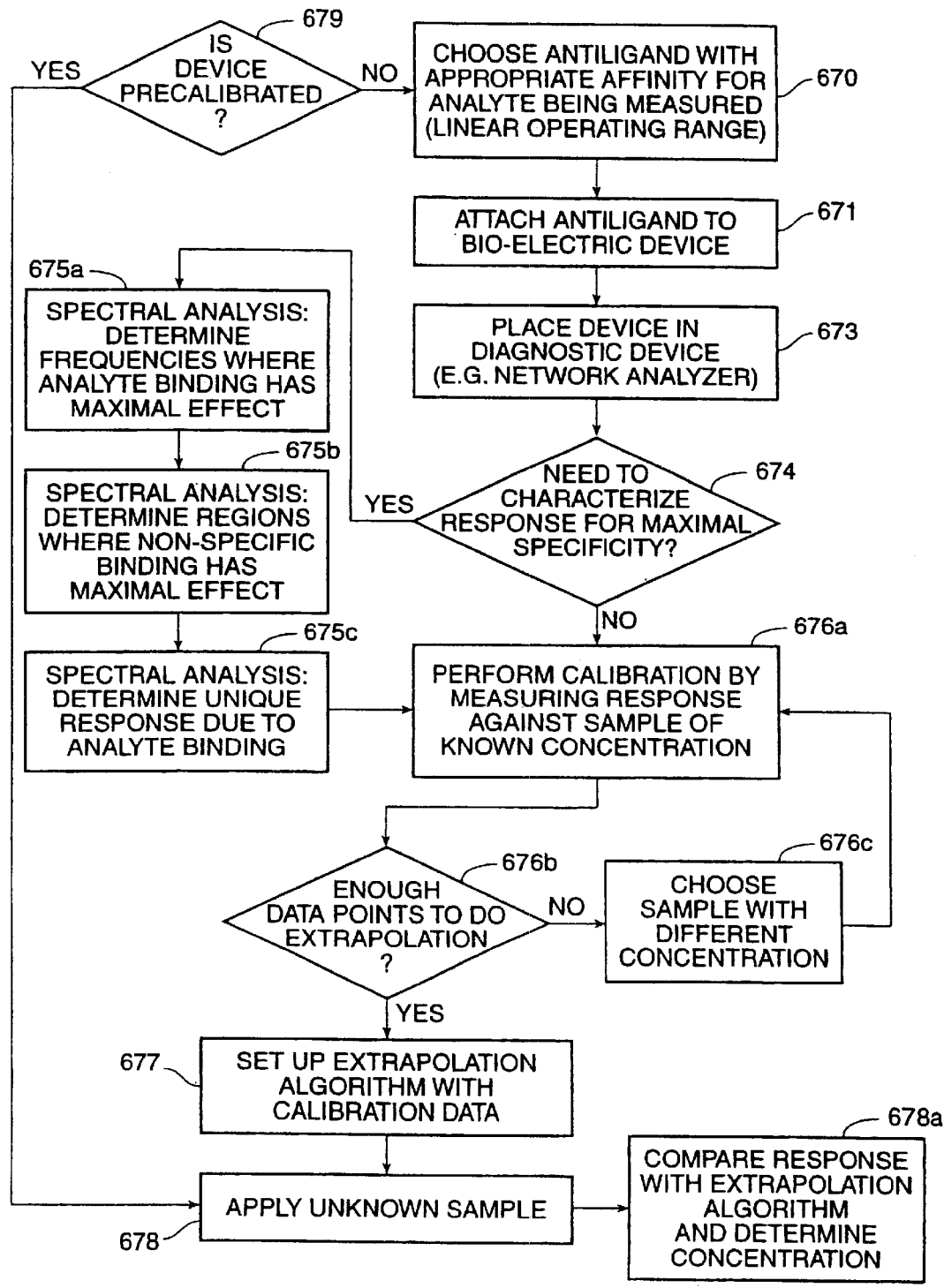
FIG. 4F illustrates one embodiment of a method for quantitating the ligand concentration of a solution in accordance with the present invention.

The bio-assay devices described herein may also be used to quantitate the concentrations of ligands. FIG. 4F illustrates one embodiment of this process. In the event the device is not precalibrated (step 679), initially at step 670, antiligands are chosen having the appropriate binding properties, such as binding affinity or kinetics, for the measured analyte. These properties are selected such that the antiligand's equilibrium constant is near the center of its linear operating region. For applications where the range of concentration is too wide for the use of a single antiligand, several antiligands may be used with differing affinities and/or linear operating ranges, thereby yielding a value for the concentration over a much wider range.

Next at step 672, the antiligands are attached to the bio-assay device or chip and at step 673 the device is connected to the measurement system. At step 674, a decision is made as to whether the response requires characterization for maximum specificity. If so, a spectral analysis is performed in which the frequencies where analyte binding has maximal binding is determined (step 675a), the regions where the non-specific binding has maximal effect is determined (step 675b), and the unique response due to analyte binding is determined (step 675c). If characterization is not required, or if so, after its completion, the device is calibrated. This step is performed in one embodiment by supplying a known concentration of ligands to the bio-assay device and measuring the resulting response (step 676a). Alternatively, if more data points are needed for the calibration (step 676b), then a sample may be chosen with a different concentration (step 676c), and the response against this concentration may be measured (step 676a). In one embodiment, the measurement is made in accordance with steps 602–612. Subsequently at step 677, an extrapolation algorithm is generated by recording the calibration points from the foregoing response. Next, a sample of unknown ligand concentration is measured. This process is accomplished in one embodiment by supplying the unknown sample to the bio-assay device (step 678), and correlating the response to the titration algorithm, and determining therefrom the ligand concentration (step 678a).

In the event that a given bio-assay device is either pre-calibrated, or calibrated by design, the only step required is to apply the ligand or analyte to the surface, and measure the response. Such a bio-assay device may be realized in many different ways. For example, some circuit parameter like impedance or characteristic frequency of a resonant circuit may be designed to change in a predetermined way when the binding event occurs, and the amount by which the parameter changes may further be designed to have a dose-response. Thus, a measurement of said circuit parameter will, when analyzed via a suitable algorithm, immediately yield a quantitative value for the concentration of a given analyte or ligand.

I. Bio-assay Device Self-Calibration

The described bio-assay devices possess a self-diagnostic capability and thus a point-of-use quality control and assurance. For a given dedication application, a particular antiligand (primary binding species) will act as an antiligand for some ligand (the secondarily binding species) of interest in the solution. The primary binding species may be attached at the point of fabrication, and the secondary binding species may be attached at the point-of-use. Thus, variations in fabrication—especially the attachment of the primary species—will cause variations in the ability of the device to bind its specific ligand. However, the amount of ligand bound will be in direct proportion to the amount of antiligand bound, thus a ratiometric measurement of the two is possible.

Figure 4G:
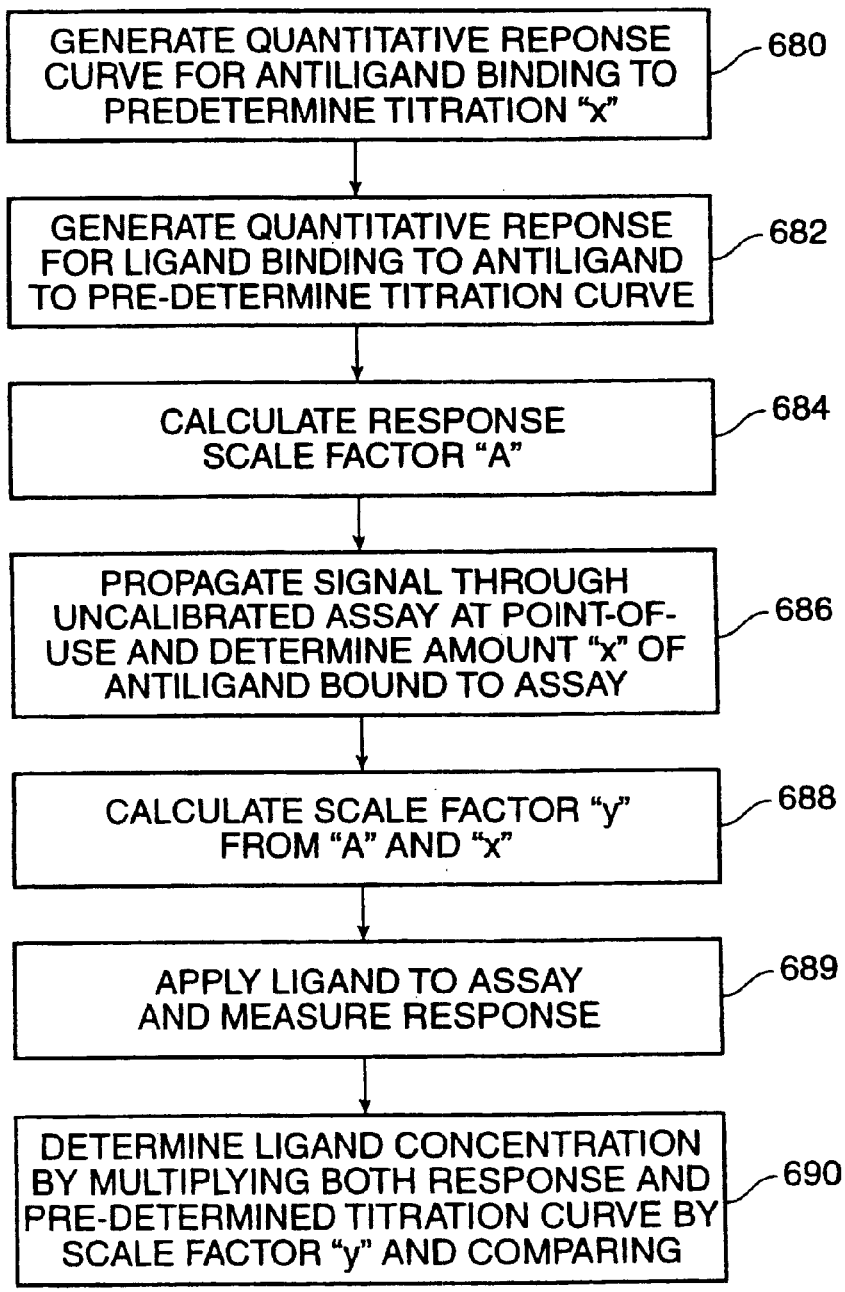
FIG. 4G illustrates one embodiment of a method for providing a self-diagnostic capability of the bio-assay device in accordance with the present invention.

FIG. 4G illustrates one embodiment of the process. Initially at step 680, a molecular binding surface is formed along the signal path by binding the appropriate antibody at various concentrations and characterizing the resulting response for each of these concentration, yielding some value "x" for each concentration. Next, at step 682, a similar titration curve is generated for the ligand by measuring the antibody/ligand binding response for several different concentrations of ligand, and a ligand titration curve is predetermined. Next, at step 684 a scale factor A is generated by taking the ratio of responses of antibody binding to ligand binding. At the point-of-use, the uncalibrated assay is then first probed (step 686) to determine the amount of bound antibody "x" and the scale factor "y" resulting therefrom. The ligand is then applied to the assay and the response is measured (step 689), and the response and predetermined titration curve are scaled by the scale factor "y" (step 690) to determine unknown concentration.

The process of FIG. 4F may also be modified to allow quantitating the amount of ligand in the solution. In the modification, the binding surface of the bio-assay device includes antiligands having a predefined affinity and ligand specificity. The solution is subsequently applied to the device, and a response is measured. The signal response will be proportional to the amount of the ligand that has bound. Thus, a titration of any given ligand may be carried out by choosing an antiligand with an appropriate linear operating range-the range in which the equilibrium constant is within a couple of log units of the desired range of concentrations to be detected. The same ratiometric analysis as described above can be applied to yield a robust and precise quantitative assay with internal controls and calibration necessary to insure reliability.

V. Measurement Systems

Various measurement systems may be used to perform the above-described methods. FIGS. 5–8 illustrate three examples of possible measurement systems: a frequency domain test system, a time domain test system and a dielectric relaxation measurement system.

A. Frequency Measurement System

Figure 5A:
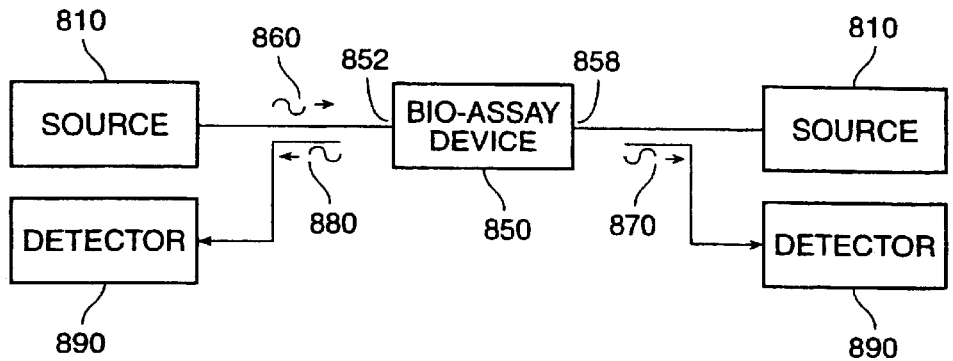
FIG. 5A illustrates one embodiment of a frequency measurement system in accordance with the present invention.

FIG. 5A illustrates one embodiment of a frequency measurement system in accordance with the present invention. The system 800 includes a signal source 810 coupled to the input port 852 of the bio-assay device 850 and a signal detector 890 coupled to the output port 858 of the bio-assay device 850. Optionally, an additional signal source may be coupled to the bio-assay device output 858 and an additional signal detector coupled to the bio-assay device input port 852 for providing complete two-port measurement capability. The system may be modified to a one-port test system in which a signal detector is coupled to the signal path for receiving a reflected signal. In a specific embodiment, the aforementioned frequency measurement system consists of a network analyzer such as model number 8510C from the Hewlett-Packard Company. Other high frequency measurement systems, such as scalar network analyzers, which provide signal information based upon transmitted and reflected signals may alternatively be used.

Figure 5B:
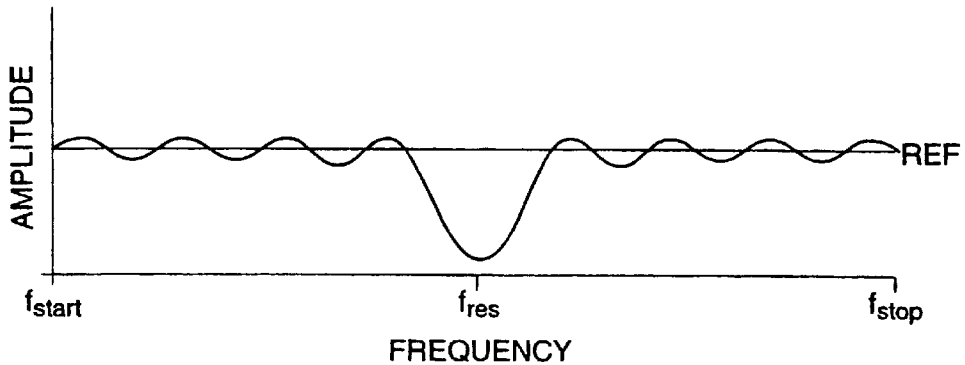
FIG. 5B illustrates a first frequency response measured which can be used to detect or identify a molecular structure in accordance with the present invention.
Figure 5C:
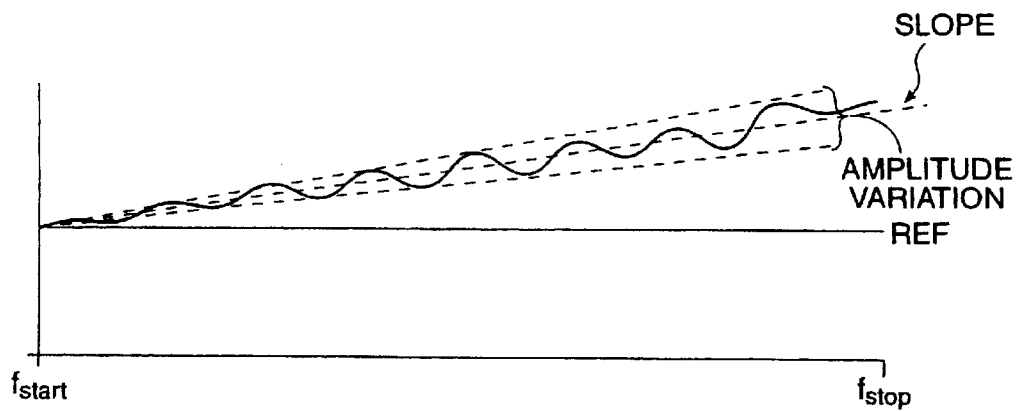
FIG. 5C illustrates a second frequency response which can be used to detect or identify a molecular structure in accordance with the present invention.

Measurements are made according to the aforementioned methodologies. Initially, an incident signal 860 is launched toward the test circuit and the transmitted and/or reflected signals 870 and 880, respectively, are subsequently recovered. The resulting signal responses will take the form of unique frequency responses or "spectral signatures," two examples of which are shown in FIGS. 5B and 5C. FIG. 5B illustrates one type of frequency response in which a resonance occurs at frequency $f_{res}$. Here, response 870 undergoes a steep fall and rise, indicating little or no signal energy reaches the output port at this frequency. The resonance is caused by the dielectric property and impedance of the MBR changing over frequency $f_{start}$ to $f_{stop}$. Different ligands will resonate at different frequency points. In addition, some ligands may exhibit multiple resonant frequency points over the measured band $f_{start}$ to $f_{stop}$. Once a ligand has been characterized as having one or more uniquely occurring resonance points, this data can be used to identify the presence of the ligand in an unknown solution. This characterization can be ascertained from empirical data or from theoretical calculations of multipole moments and resonant frequencies. Furthermore, when detecting the presence of secondary binding events, this data can indicate when an analyte is bound to a ligand by a change in the one or more unique resonance points.

FIG. 5C illustrates another type of frequency response which can be used to detect or identify a molecular structure. In this case, the frequency response exhibits a generally monotonically increasing or decreasing trend with some degree of amplitude variation. The response's slope and/or the amplitude variation may be used to detect and/or uniquely characterize the bound molecule. Thus in the described manner, the resonant frequency points, slope, trend, and variation of the test signal's phase may be used to uniquely identify the molecular binding event. The frequency response may be measured at the input port 852, at the output port 858 or at both ports to uniquely identify the bound molecular structure.

Figure 6:
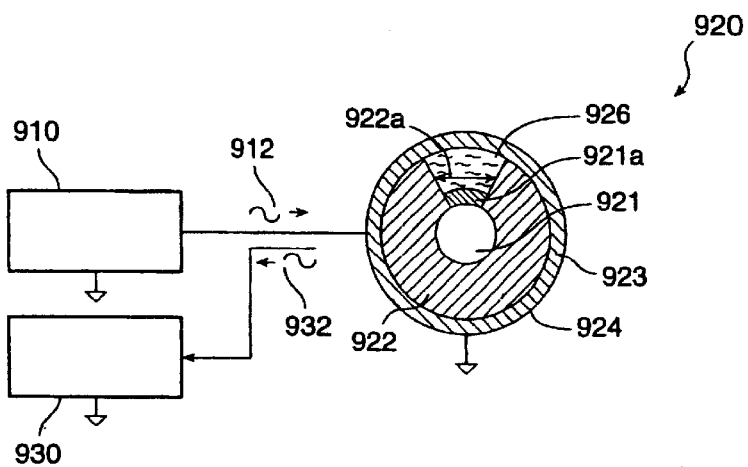
FIG. 6 illustrates a second embodiment of a frequency measurement system in accordance with the present invention.

FIG. 6 illustrates a second exemplary embodiment of a frequency measurement system in accordance with the present invention. The bio-assay device under test 920 consists of coaxial topology (shown in FIG. 5G) having a center conductor 921, a first insulator 922 having a cavity 922a, a second insulator 923, and an outer conductor 924. Solution 926 occupies cavity 922a. Of course, devices of other circuit topologies may be tested as well.

Once the solution 926 is added to the cavity 922a, the molecules within the solution 926 form a MBR 921 a proximate to the center conductor 921. During the measurement, a signal source 910 launches an incident test signal 912 to center conductor 921. The MBR 922a modulates the incident test signal 912, and the reflected test signal 932 provides a unique signal response which can be used to identify the ligand. The one-port coaxial configuration may be realized, for instance, as a sub-cutaneous needle structure.

B. Time Domain Measurement System

Figure 7:
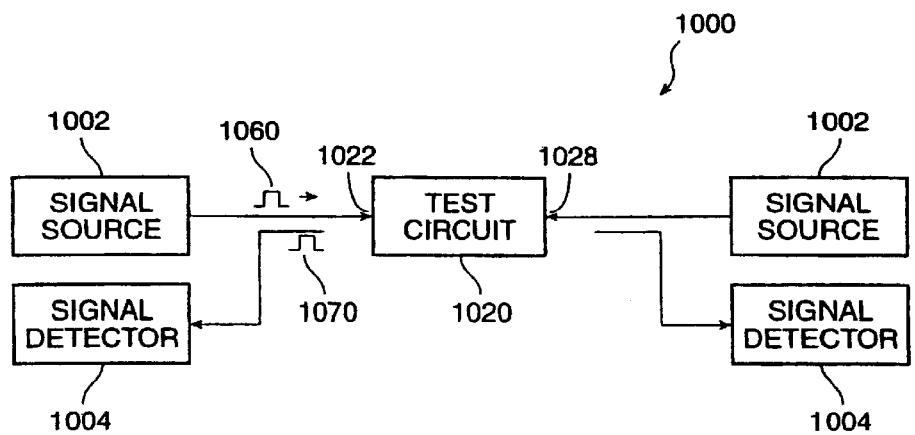
FIG. 7 illustrates one embodiment of a time domain measurement system in accordance with the present invention.

FIG. 7 illustrates one embodiment of a time domain measurement system 1000 in accordance with the present invention. The system includes a signal source 1002 and a detector 1004 coupled to the input port 1022 of the test circuit (consisting of any of the bio-assay devices described herein). In an alternative embodiment, an additional signal source and detector may be coupled to the output port 1028 to provide complete two-port measurement capability. Further alternatively, the system may comprise a one-port test system in which a signal detector is coupled to the signal path for receiving a reflected signal. In a specific embodiment, the time domain measurement system consists of a time domain reflectometer such as model number 11801 manufactured by the Tektronix Corporation. Other high frequency measurement systems, such as network analyzers having a time domain measurement mode which provide signal information based upon transmitted and reflected signal pulses may alternatively be used.

In the time domain measurement system, the input test signal 1060 consists of a time domain pulse, the reflected portions of which can be displayed over time. In the present embodiment, an incident pulse 1060 is launched toward the portion of the transmission line which is tightly coupled to the assay surface. Due to the dielectric property of the MBR, a portion of the incident pulse 1060 is reflected toward the detector 1004. The reflected pulse 1070 will exhibit a unique shape and/or time delay which is characteristic of the MBR's dielectric properties, which are in turn largely defined by the dielectric properties of the ligand, antiligand, and the surrounding solution. Thus, the pulse shape and delay of the reflected pulse 1070 can be used to characterize and identify the ligand. The time domain test system may be used separately or in conjunction with the high frequency test system to identify one or more unknown ligands.

C. Dielectric Relaxation Measurement System

As known in the art, the dielectric relaxation frequency of a ligand is the rate at which the dielectric properties of the molecular level changes when an electric field is applied to the molecule. As with the dielectric properties of the ligand, the dielectric relaxation frequency is primarily defined by the structure and binding geometries unique to each molecule. Thus once measured, the dielectric relaxation frequency of a ligand can be used to identify it.

Figure 8:
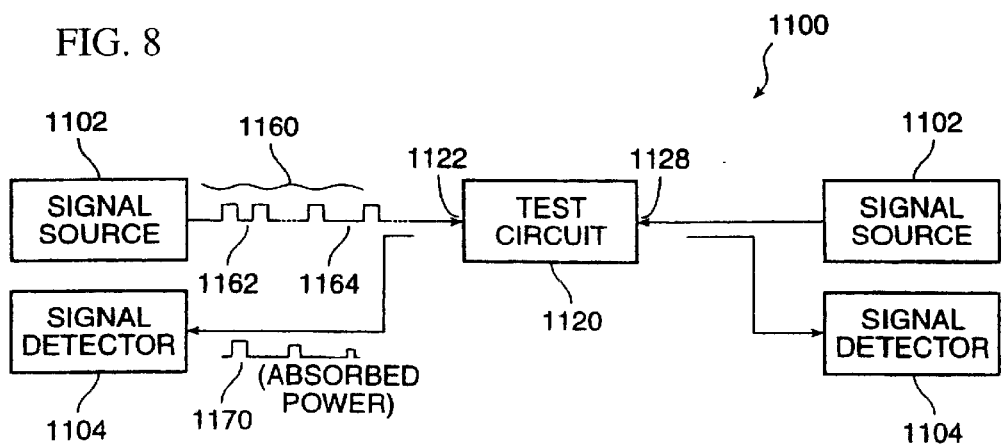
FIG. 8 illustrates one embodiment of a dielectric relaxation measurement system in accordance with the present invention.

The dielectric relaxation frequency can be quantified by measuring the rate at which the ligand absorbs power over frequency. FIG. 8 illustrates one embodiment of a system 1100 for making this measurement. The measurement system 1100 is similar to the time domain measurement system 1000 illustrated in FIG. 7 and includes a signal source 1102 and a detector 1104 coupled to the input port 1122 of the test circuit (consisting of any of the bio-assay devices described herein). An additional signal source and detector may be coupled to the output port 1128 to provide complete two-port measurement capability. In a specific embodiment, the time domain measurement system consists of a time domain reflectometer such model number 11801 manufactured by the Tektronix Corporation. Other high frequency measurement systems, such as network analyzers having a time domain measurement mode which provide signal information based upon transmitted and reflected signal pulses may alternatively be used.

The input test signal 1160 consists of separate pulse groups, each group having two or more incident pulses and a different pulse interval. The pulse groups 1162 and 1164 are launched toward the portion of the transmission line which is tightly coupled to the binding surface. If a pulse group 1162 has an interval substantially equivalent to the dielectric relaxation period (the reciprocal of the relaxation frequency), the MBR will absorb successively less energy in succeeding pulses. The decrease in signal absorption can be measured in the reflected response 1170 at the input port 1122 or at the output port 1128. As an alternative measurement quantity, the remaining signal power may be measured either at the input port 1122 or the output port 1128.

The rate of change of signal absorption and the pulse interval at which the change occurs can then be plotted and used to characterize and identify the unknown bound molecule(s). This system characterization may be used independently or in conjunction with the above-described time and/or frequency domain test systems.

In all of the above systems, one of skill in the art will readily appreciate that such systems can be scaled down to the chip level using such technologies as Microwave Monolithic Integrated Circuits (MMIC) and the like. Such miniaturized systems can be readily extended to highly parallel systems capable of detecting and measuring hundreds, thousands, or tens of thousands of compounds simultaneously. These systems can be configured to yield "logic gates" which are switched by the binding event itself, such as by changing a characteristic impedance and thus the transmission and/or reflection coefficients, or by changing the band pass properties of such a circuit, and using this as the on/off gate.

VI. Integration of Detection System with Chip Technology

A. General

The bio-assay device described above, can be included on an inexpensive and disposable chip. Because of the ease of miniaturization, very small chips with thousands or tens of thousands of addressable bio-assay devices contained therein can be prepared. As described in additional detail below, chips containing arrays can be used in detecting the presence of various analytes of interest in a sample and screening libraries of molecules.

The chips can be manufactured from a variety of inexpensive materials, such as plastic or glass substrates, for example. The chips can have a variety of shapes and sizes and the binding layer can vary in structure as described above in relation to FIGS. 1D–1F. The chip itself typically includes arrays containing multiple elements or sites. Each element of the array includes a signal path such as a transmission line and appropriate circuitry for addressing the element. In each element, a protein or ligand (often a plurality of proteins or ligands) are coupled to the signal path located within the element.

In current methodologies using chips to analyze protein binding events, the ligand contained in a sample typically must be labeled. The present invention eliminates the need to label ligands or target proteins and the problems associated with such labeling, since binding events can be detected directly through modulation of the transmitted signal.

B. Addressing Array Elements

In general terms, it is possible to interrogate each element of an array by propagating a signal down each of the signal paths which run to the various elements and detecting a signal resulting from the formation of a protein/ligand complex at a particular element. In some instances, signal detection involves transmitting a signal down a signal path when only a target is coupled to the signal path and measuring a baseline signal. After the target is contacted with sample and the array optionally rinsed, another signal is propagated down the transmission line and a measured signal compared with the baseline signal to obtain a difference between the signals. It is also possible to simultaneously transmit signals down multiple signal paths—one path extending to a test element and another path running to a control element which lacks either probe and/or target. Signals propagated down the various signal paths can be launched simultaneously or serially, i.e., launched at different times.

Arrays make use of the unique ability of the methods to measure simultaneously the affinity, kinetics, and unique dielectric profiles of each binding event, and to make these measurements at a multiplicity of addressable sites on the array. The exact nature of the addressing depends on the applications, but an example of the general strategy is as follows. A vector space is defined by the variables $K_{eq}$, $k_A$, and $\omega=(\omega 1,\omega 2,\omega 3, \ldots)$ where these variables represent the equilibrium constant, the kinetic constant, and a basis set of N frequencies at which the dielectric properties are probed. An N+2 dimensional space is thus defined into which every binding event can be mapped. A group of reference molecules (e.g., proteins) is subsequently chosen which represents a spectrum of binding events of interest, such as a group of antibodies having different binding specificities. These reference molecules are then attached to addressable points on the chip. A particular species of molecules or group of species (e.g., analytes that bind to the proteins serving as the reference molecules) is introduced to the chip, and each address is then probed for the value of each of the points in the vector space defined above (or a suitable subset thereof). Each species can then be represented by an address in the vector space. The complexity of the system will depend on the size of the vector space and the total number of different immobilized ligands on the surface.

As an example of the above, consider a simple system comprised of two different proteins which are analyzed at four different frequencies; and further, each of these frequencies can be parsed into ten different amplitudes. Such a system would have 100 million possible addresses. An unknown placed in the system can be represented by a unique address of the form [(1,5,3,7)(4,8,6,7)], where the first four numbers represent the spectral response of one of the proteins at the four selected frequencies, and the latter four numbers represent the spectral response of the other protein at the four selected frequencies. Thus with just two probes and four frequencies, 100 million unique addresses can be generated.

C. Detection

Signals are detected by launching a test signal down the signal path or transmission line and then detecting a response signal resulting from interaction of the test signal with the binding complex. In some methods, the detection first involves propagating a reference signal and measuring a baseline signal when one or more of the components of the binding complex is not present. For example, the baseline signal can be obtained with just a buffered solution; in other instances, the baseline signal is obtained with either the protein or ligand coupled to the signal path, but not both. In certain embodiments, the transmitted signal is a microwave.

Signals generated as a result of the formation of a protein/ligand complex at the various sites can be tracked using a computer to monitor and store the signals from the various elements. In this way, it is possible to identify which elements include a protein/ligand complex. In those instances in which the ligand is attached to the array, it is possible to identify the ligand that binds the target protein because each element is individually addressed and monitored.

Often signal measurement involves scanning a range of frequencies or wavelengths. As indicated above, the signal generally ranges from the MHz to hundreds of Gigahertz level. In some embodiments, the signal is a microwave. In certain instances, for example, a signal may be scanned from 1 to 21 GHz.

The detector for the modulated signal can include a version of a "logic gate" in which the presence of a particular ligand or analyte has the effect of either turning on the gate or turning off the gate, as is appropriate for a given application. Such a gate may be realized in any number of ways which translate the binding event into an electromagnetic signal which can be assigned to one of two possible states corresponding to off and on, 1 or 0, and the like. The two states could be different frequencies of a resonant cavity or waveguide corresponding to bound and unbound, or amplitude changes in a transmission line or waveguide which correspond to bound and unbound, or changes in the band-pass of a particular circuit, or the like.

D. Specific Array Embodiments

1. Test System

Figure 13:
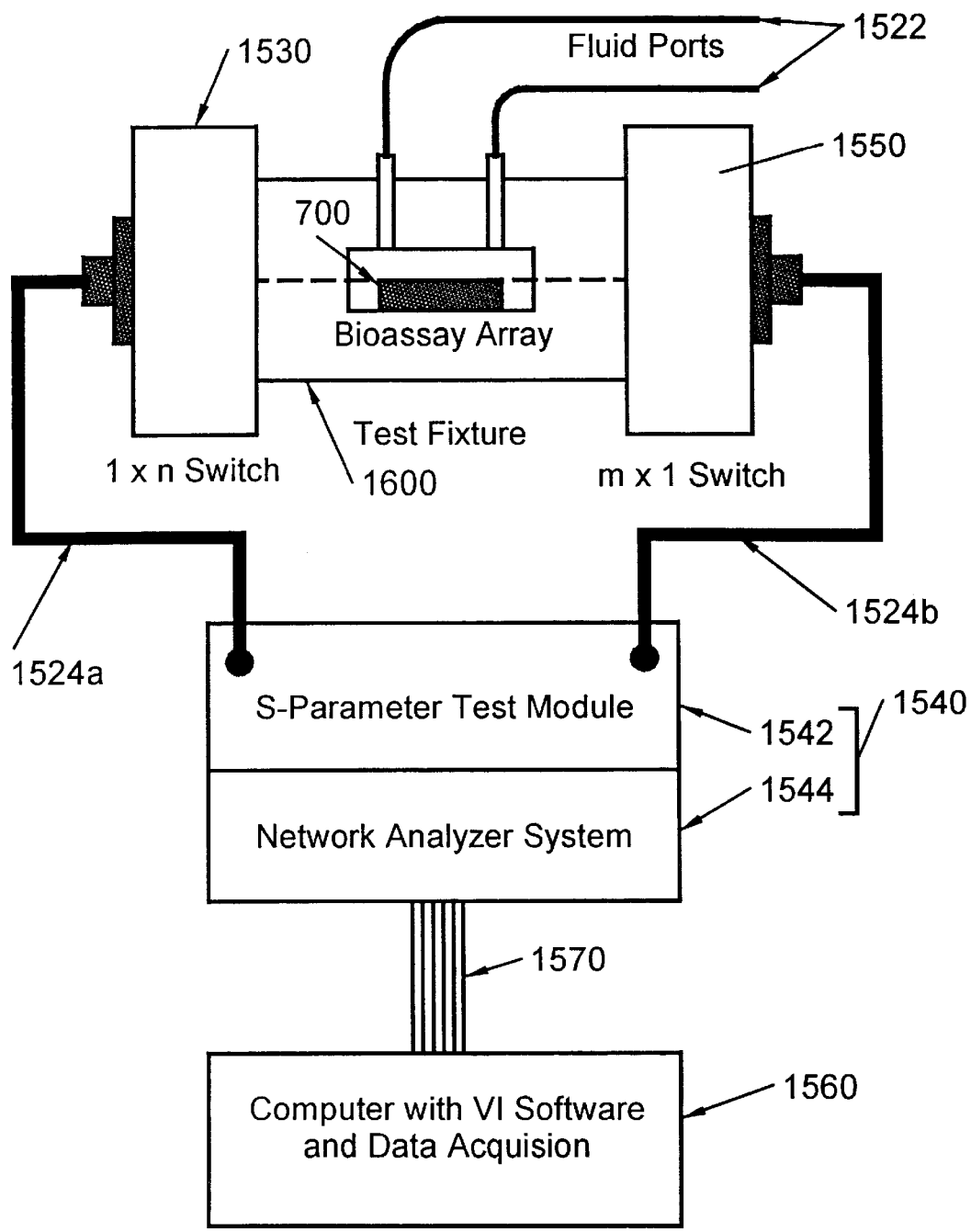
FIG. 13 illustrates one possible embodiment of an N×M array test system in accordance with the present invention.

FIG. 13 illustrates one possible embodiment of an N×M array test system 1500 in accordance with the present invention. The test system includes a test fixture 1600 further described below, a 1×N input switch 1530, a measurement system 1540, a M×1 output switch 1550, and a computer 1560. Measurement system 1540 communicates test signals to the test fixture 1600 via input test cable 1524*a* and 1×N input switch 1530. The test signal is subsequently received from the test fixture via M×1 output switch 1550 and output test cable 1524*b*. Computer 1560 controls 1×N input switch 1530, measurement system 1540, and M×1 output switch 1550 via a control bus 1570.

In one embodiment, measurement system 1540 includes an S-Parameter Test Module model no. 8516A (1542), a Frequency Synthesizer (not shown) model no. 8341B, and a Vector Network Analyzer model no. 8510B (1544), all of which are manufactured by the Hewlett Packard Company of Palo Alto, Calif. (www.hp.com). In this embodiment, measurement system 1540 provides a measurement capability between the frequencies of 45 MHz and 40 GHz. In an alternative embodiment, measurement system 1540 may consist of model number HP 8751A network analyzer which provides a measurement capability between 5 Hz and 500 MHz. In a further embodiment, measurement system may consist of model number HP 85106D which provides a measurement capability between 33 GHz and 110 GHz, both manufactured by the Hewlett Packard Company. Other measurement systems such as scalar network analyzers, Time Domain Reflectometers, an other similar measurement systems may also be used to detect a change in the test signal which is attributable to the dielectric properties of the MBR.

Test cables 1524 support the propagation of the test signals at the desired frequency. In one embodiment, test cables consists of model number 6Z PhaseFlex™ Microwave test cables manufactured by the W. L. Gore and Associates, Inc. of Newark Delaware (www.gore.com). Control bus 1570 provides communication between the test system and computer 1560 and in the illustrated embodiment consists of a General Purpose Instrument Bus (GPIB). In alternative embodiments, measurement system 1540 and computer 1560 may be integrated within a single automated measurement unit.

Computer 1560 controls measurement system 1540 to generate test signals at one or more frequencies, output power levels, signal shapes, phase offsets or other measurement settings. In the preferred embodiment, computer 1560 includes a +450 MHz microprocessor, such as those manufactured by the Intel Corporation of Santa Clara, Calif. (www.intel.com). Test system control, data acquisition, and analysis may be performed using a graphical programming software tool, such as LabVIEW® manufactured by the National Instruments Corporation of Austin, Tex. (www.natinst.com).

Alternatively or in addition, measurement system 1540 may include a Time Domain Reflectometer (TDR) system, such as those optionally available with the above-described network analyzers or described in the incorporated patent application entitled: "Method and Apparatus for Detecting Molecular Binding Events," Ser. No. 09/243,194. Essentially, TDR systems transmit a signal pulse towards a unit under test. The return signal (either reflected from or transmitted through the unit under test) can be analyzed to ascertain information about the unit under test. Specifically in the present embodiment, the dielectric properties of the MBR will modulate the signal pulse, thereby enabling detection and identification of the molecular binding events therein.

TDR measurements may be made at the fixture level using the aforementioned systems, or at the bio-assay device level utilizing one or more of the standard techniques of microwave monolithic circuit (MMIC) technologies. When a TDR measurement is made at the device level, a time-domain test signal is generated in close proximity to the bio-assay device. This signal is then propagated along the signal path to the bio-assay element via standard conductive geometries used in MMIC technologies. The molecular binding region modulates the time-domain test signal, and the modulated signal is then recovered to be analyzed.

The 1×N input switch 1530 routes the test signal from the input test cable 1524*a* to one of the N test fixture signal inputs. The M×1 output switch 1550 routes the test signal from one of the M test fixture outputs to the output test cable. Input and output switches 1530 and 1550 may consist of any switching or multiplexing means which will upport the propagation of the desired test signal. For instance, input and output switches 1530 and 1550 may consist of low frequency switches (DC to 2 GHz), such as those manufactured by Amplifonix, Inc. of Philadelphia, Pa. (www.amplifonix.com). Switches for use at higher frequencies (2–18 GHz), such as those manufactured by the General Microwave Corporation of Amityville, N.Y. (www.generalmicrowave.com) may alternatively be employed. Connection between bio-assay device and input and output switches 1530 and 1550 may be made using insulated cables, wire bonds, or other conventional interconnection means appropriate for the test frequency of operation.

In an alternative embodiment, input and output switches 1530 and 1550 and the bio-assay array form a monolithic integrated circuit. For instance, when the bio-assay array is fabricated using GaAs semiconductor processing techniques, input and output switches 1530 and 1550 may consist of integrally formed PIN diodes which are coupled to the bio-assay array. Further alternatively, input and output switches 1530 and 1550 may form an integrated assembly in which the input and output switches 1530 and 1550 are discrete components which are connected (via wire or ribbon bonds) to the bio-assay array. Both alternative embodiments provide advantages in that the interconnecting structures are miniaturized or eliminated, thereby reducing or eliminating the signal loss associated therewith.

As explained, the bio-assay array may be fabricated in wafer form using semiconductor processing techniques. In this embodiment, the array test system 1500 may consist of a wafer probe test station, such as those manufactured by Cascade Microtech, Inc. of Beaverton, Oreg. (www.cascademicrotech.com) which includes or is coupled to the aforementioned input and output switches 1530 and 1550, and computer 1560. The wafer probe station utilizes one or more probe cards, each of which is capable of providing a large number of low loss, low VSWR signal interconnections to the bio-assay array.

The probe card(s) may be used to provide N and/or M signal interconnections to the remotely located input and/or output switches 1530 and 1550, respectively. Alternatively, input and/or output switches 1530 and 1550 may be monolithically fabricated with the bio-assay array, in which case the probe card(s) provides a single input and/output signal transition to the measurement system 1540. In this latter embodiment, the probe card(s) includes probes for providing switch control voltages to the monolithically formed switches.

Alternatively or in addition, measurement system 1540 may include a Time Domain Reflectometer (TDR) system, such as those optionally available with the aforementioned network analyzers or described in the incorporated patent application entitled: "Method and Apparatus for Detecting Molecular Binding Events," Ser. No. 09/243,194.

2. Array Test Fixture

Figure 14A:
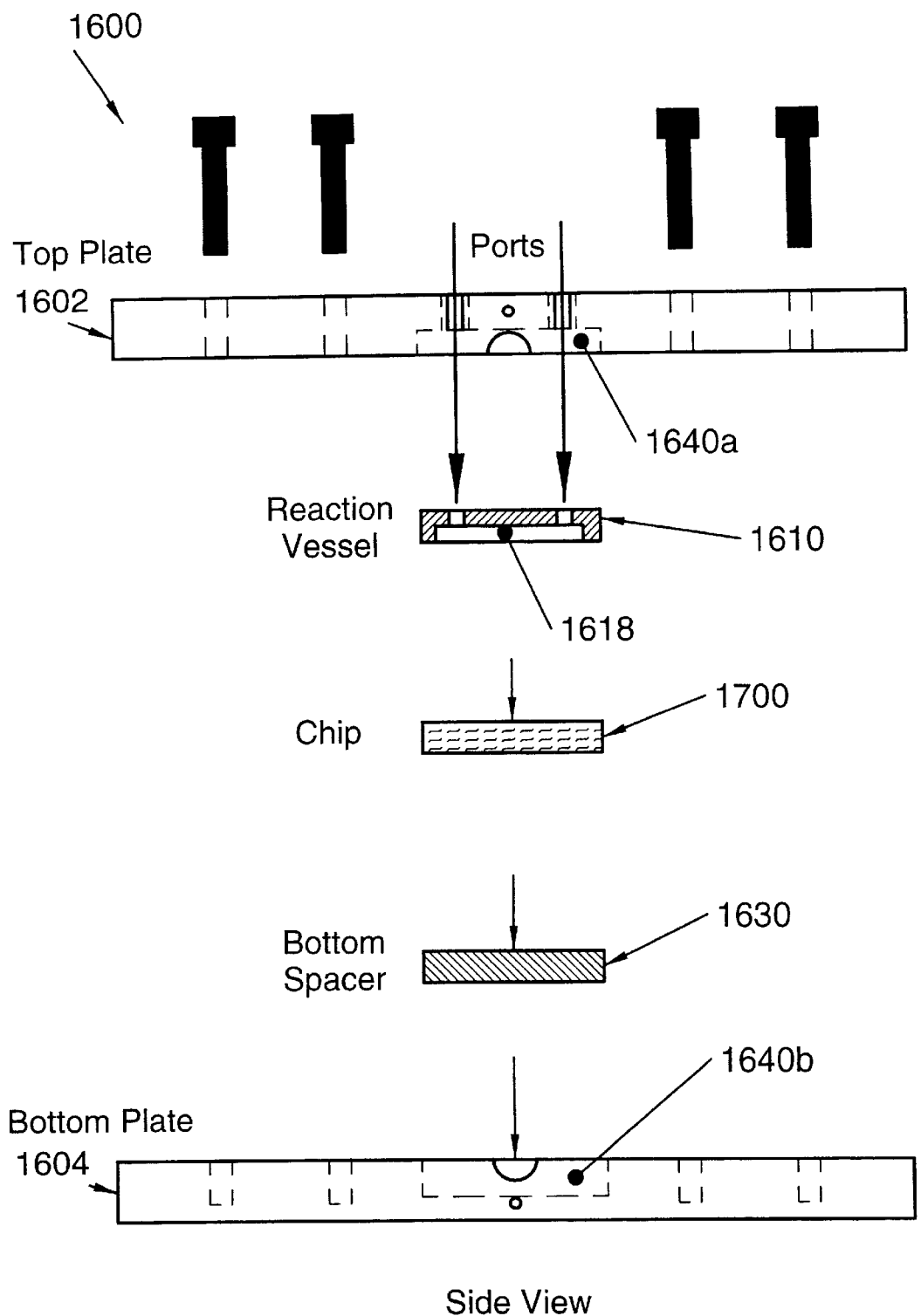
FIG. 14A illustrates a side exploded view of an N×M array test fixture in accordance with the present invention.

FIG. 14A illustrates a side view of one possible embodiment of the N×M array test fixture 1600 in accordance with the present invention. Test fixture 1600 includes a top plate 1602, bottom plate 1604, and a sample cavity consisting of top and bottom recesses 1640a and 1640b, respectively, which holds the aforementioned reaction vessel 1610, bio-assay array 1700 (further described in FIG. 15A below), and bottom spacer 1630 elements. In the N×M array test fixture embodiment, the dimensions of sample cavity 1640 and correspondingly reaction vessel 1610 and bottom spacer 1630 are designed to accommodate the bio-assay device 1700 which may be larger or smaller than the bio-assay device. Each array element includes a small, monolithically deposited structure to form a recessed area over the signal path in order to hold a portion of the applied sample in electromagnetic communication with the signal path of each array element.

Figure 14B:
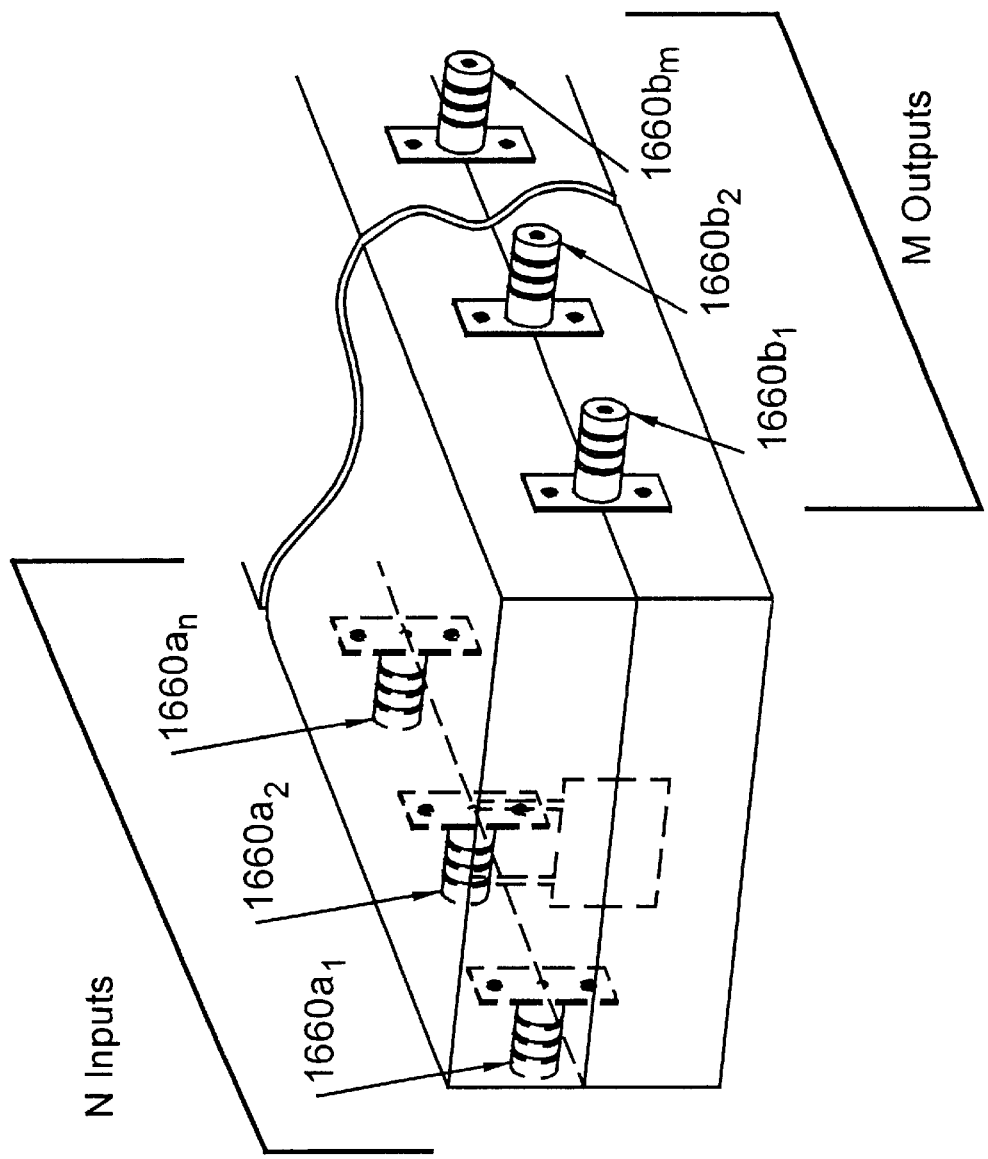
FIG. 14B illustrates a perspective view of an N×M array test fixture in accordance with the present invention.

FIG. 14B illustrates an end view of the N×M array test fixture 1600. Test fixture 1600 includes N input connectors $1660a_1$ to $1660a_n$ and M output connectors $1660b_1$ to $1660b_m$. Test fixture 1600 also includes N input transmission lines (not shown) which provide a signal transition between the fixture's N connectors $1660a_1$ to $1660a_n$ and the bio-assay's N inputs. Test fixture 1600 further includes M output transmission lines (not shown) which transition between the bio-assay's M outputs and the fixture's M output connectors $1660b_1$ to $1660b_m$. The input and output transmission lines may be realized as insulated conductive wires, microstrip, stripline, coplanar waveguide transmission lines deposited on a dielectric substrate, or other conventionally known signal path architectures. The choice of the transmission line's architecture will be influenced by the test frequency band and the bio-assay device's input and output port density.

3. Bio-assay Array

Figure 15A:
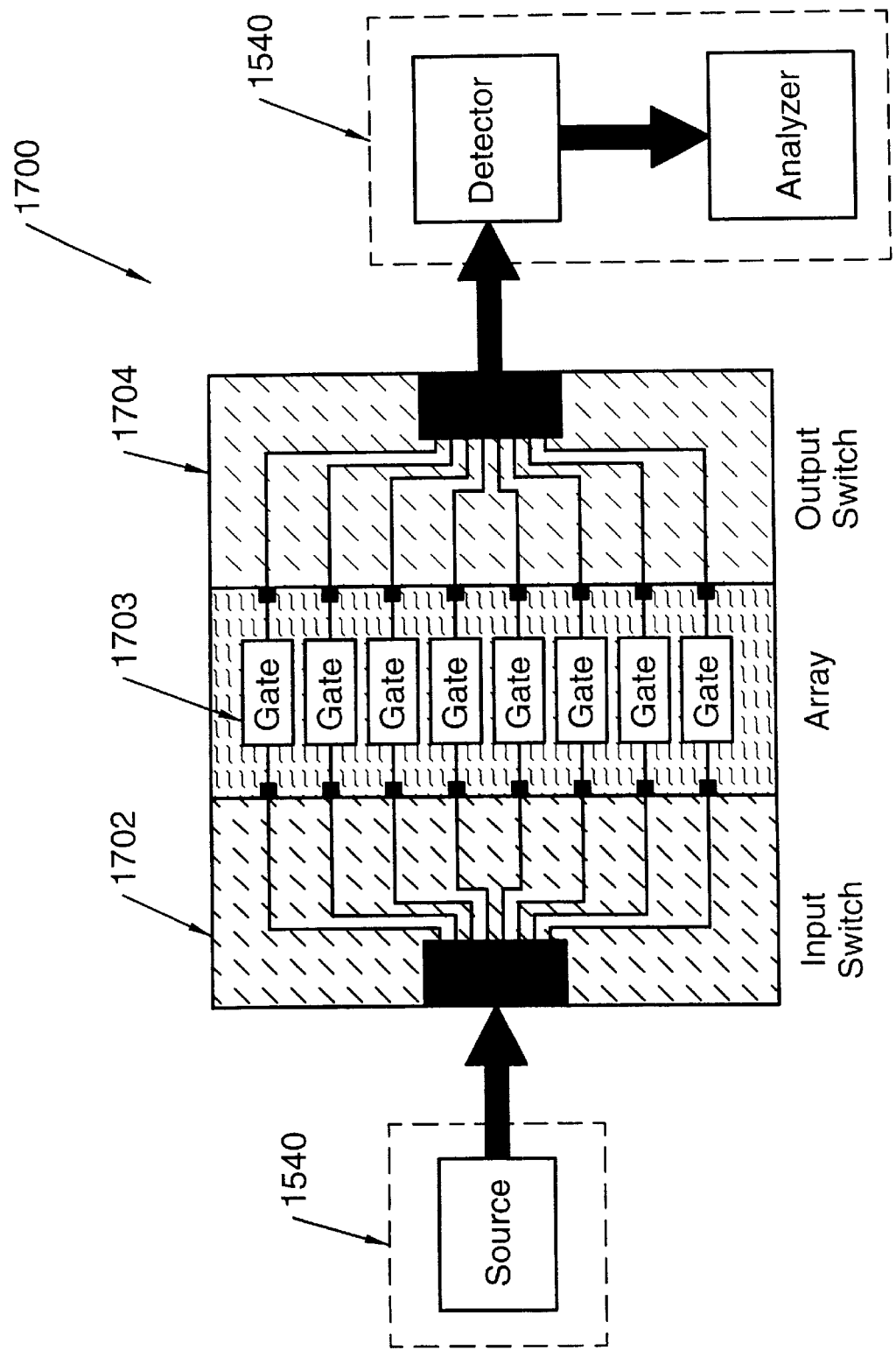
FIG. 15A illustrates one embodiment of a bio-assay array in accordance with the present invention.

FIG. 15A illustrates one embodiment of an integrated bio-assay array 1700 in accordance with the present invention. The integrated array 1700 is supplied with a test signal via the signal source of measurement system 1540. The array 1700 includes an integrated 1×N input switch and M×1 output switch which are monolithically formed during the semiconductor fabrication process. The number of inputs may be the same as the number of outputs in which case M=N, the number of inputs and outputs may differ.

The 1×N input switch 1702 routes the incoming test signal to the desired array element within array 1703. The MBR in the array element $1703_j$ modulates the test signal according to the dielectric properties of the molecular binding events which make up the MBR. An M×1 output switch 1704 routes the modulated test signal to a detector of the measurement system 1540. An analyzer of the measurement system 1540 compares the input and modulated test signals to determine the measured signal response. While each array element $1703_j$ is illustrated as a two-port device, those of skilled in the art will appreciate that one-port or multiple port array elements may be used alternatively.

As explained above, the array 1703 and the input and output switches 1702 and 1704 may be fabricated either as discrete components or in wafer form and integrated in varying degrees depending upon the application. In the illustrated embodiment, the array [1700] 1703 and input and output switches 1702 and 1704 are monolithically formed on a semiconductor wafer. In another embodiment, the input and output switches 1702 and 1704 are monolithically formed separately from the detector array 1703 and connected via wire or ribbon bonds. In a further embodiment, input and output switches 1702 and 1704 and array 1703 are each discrete units. Those skilled in the art will appreciate that other arrangements are also possible.

Figure 15B:
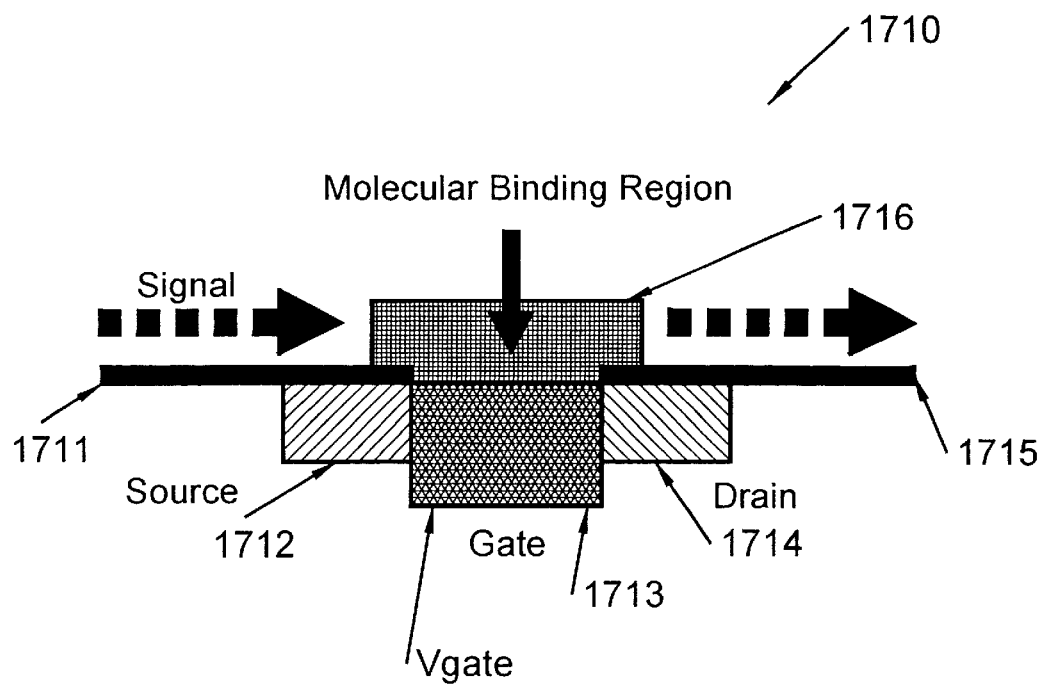
FIG. 15B illustrates one embodiment of an array element in accordance with the present invention comprising a series-connected, electronically switched Field Effect Transistor.

FIG. 15B illustrates one embodiment of an array element, shown as a series connected, electronically switched Field Effect Transistor (FET) 1710. FET 1710 may be a Metal Semiconductor Field Effect Transistor (MESFET) fabricated using GaAs processing. Other transistor configurations are also possible for instance, High Electron Mobility Transistors (HEMT), heterostructure FETs, homogenous or heterojunction bipolar transistors, or PN junctions devices such as PIN diodes to name a few. Other active or passive array elements may be used alternatively or addition to these as well.

In the embodiment of FIG. 13B, the source and drain terminals 1712 and 1714 of FET 1710 are employed as the input and output ports, 1711 and 1715 respectively, and the on/off state of the FET 1710 is controlled via a voltage applied to the gate terminal 1713. The sample is applied over FET 1710 such that the MBR 1716 provides a parallel path between the source and drain terminals 1712 and 1714. FET 1710 is designed such that when turned off, it presents a drain to source resistance ($R_{ds}$) which is much higher than resistance through the MBR 1716. In this instance, the signal path propagates through the MBR 1716 which modulates the test signal. The modulated test signal is recovered (through a DC blocking capacitor to remove the DC bias) and compared to the input test signal to detect and/or identify the molecular binding events occurring within the MBR 1716. When the FET 1710 is activated, it provides a much lower $R_{ds}$ compared to the resistance of the MBR 1716. In this instance, the MBR 1716 is effectively switched out of the signal path and the signal propagates largely unaffected by it. Thus by simply opening or closing a switch, an array element may be addressed.

Figure 15C:
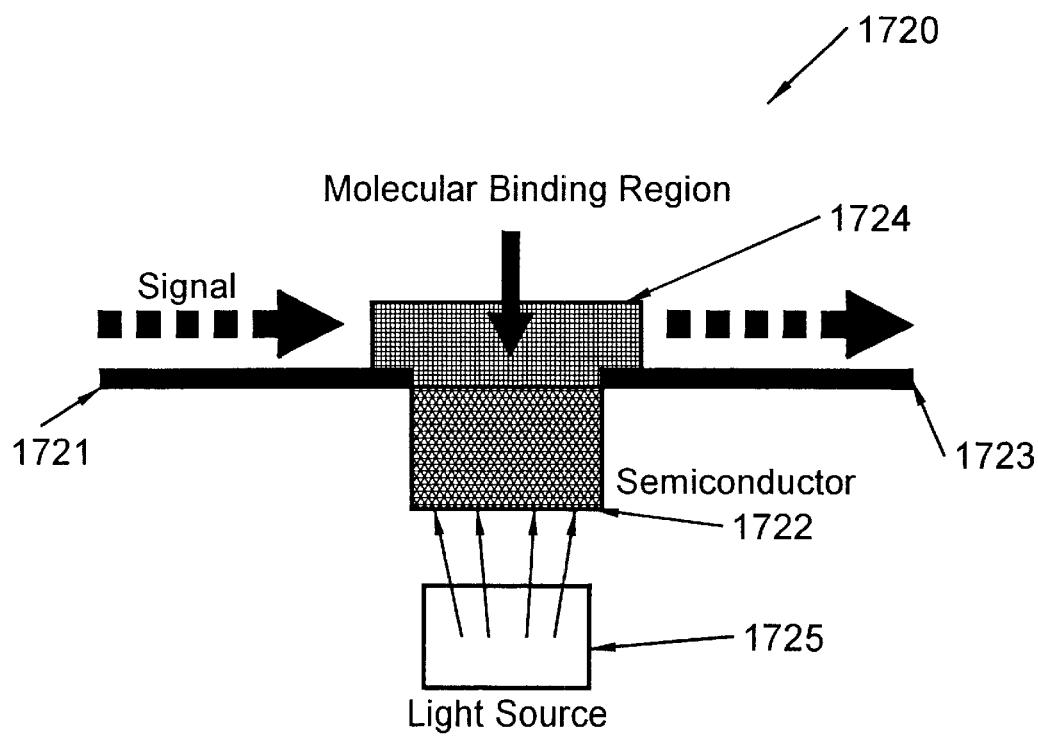
FIG. 15C illustrates one embodiment of an array element in accordance with the present invention comprising a series-connected, optically switched Field Effect Transistor.

FIG. 15C illustrates a further embodiment of a FET used as an array element which is optically switched. FET 1720 is connected similarly to FET 1710 described in FIG. 15B and may consist of a photosensitive transistor, diode or other photosensitive device. The gate junction 1722 may be illuminated, for instance, with normal sunlight, a laser, a Light Emitting Diode (LED) 1725, or other source having a wavelength to which FET 1720 has a high sensitivity. The incident light activates FET 1720 to switch out the MBR 1724. When the FET 1720 is deactivated, the test signal propagates from the FET input 1721 to the FET output 1723 through the MBR 1724 and is modulated thereby. The modulated test signal is recovered (through a DC blocking capacitor not shown) and analyzed to determine the presence and/or identity of molecular binding events within the MBR 1724.

Figure 15D:
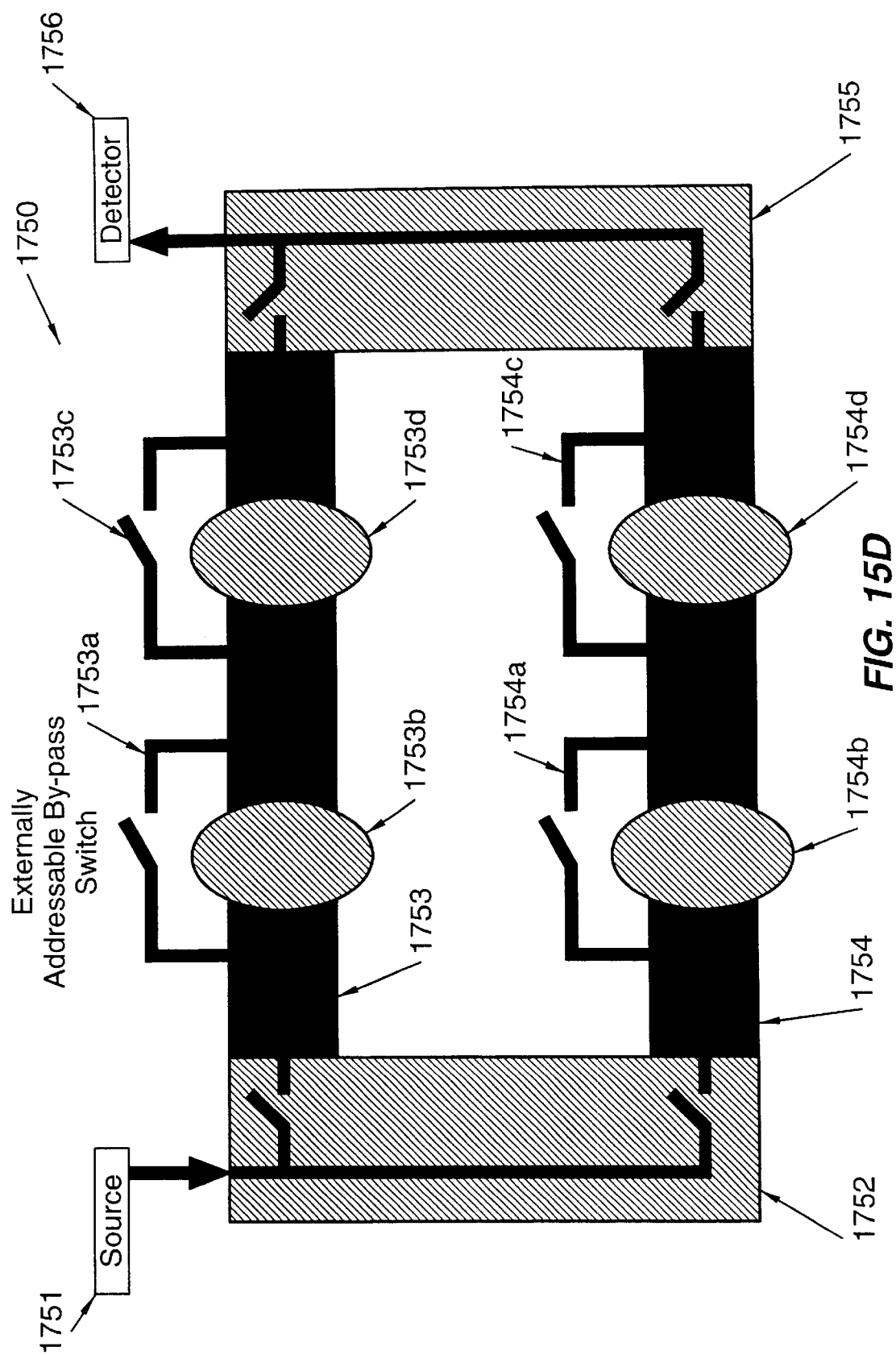
FIG. 15D illustrates one embodiment of an array in accordance with the present invention comprising two paths of two, serially-connected FET devices.

FIG. 15D illustrates an extension of FIG. 15B and 15C in which two or more FETs are serially-connected. Array 1750 includes a first test path 1753 along which addressable switches 1753a and 1753c are coupled. In one embodiment, addressable switches are electronically or optically controlled MESFETs, described above. Array path 1753 further includes sample regions 1753b and 1753d, each of which provides a parallel signal paths to the corresponding addressable switches 1753a and 1753c.

As described above, addressable switches 1753a and 1753c operate to switch in and out the sample regions 1753b and 1753d between a signal source 1751 and a signal detector 1756 via input switch 1752 and output switch 1755. Thus, a particular row is made into a transmission path in which a single assay site appears as an impedance mismatch. Each assay site can be either switched into the circuit, or switched out of the circuit, as desired. The nature of the impedance mismatch is a function of binding and other changes in the MBR. Additional signal paths such as signal path 1754 (having addressable switches 1754a and 1754c connected in parallel to sample regions 1754b and 1754d) may be included in the array and cross-strapped to the other paths using other low loss switches (not shown) to allow the test signal to propagate between signal paths 1753 and 1754. Input and output switches 1752 and 1755 are used to inject and recover the test signal to/from the array 1750. As those of skill in the art will appreciate, the described array may be extended to any number of N×M elements to provide a two dimensional array device.

Figure 15E:
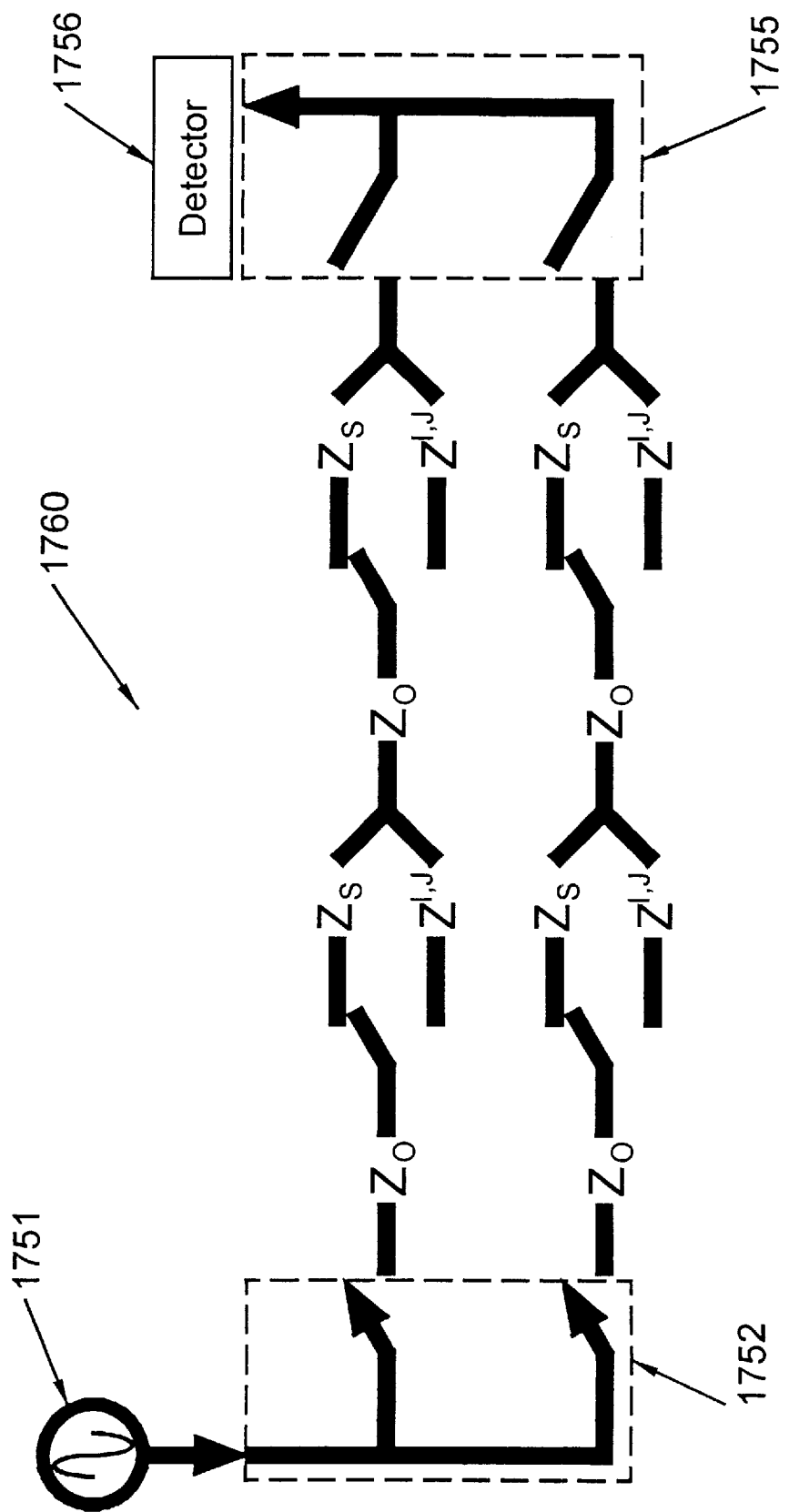
FIG. 15E illustrates the circuit equivalent model of the array shown in FIG. 7D in accordance with the present invention.

FIG. 15E illustrates the circuit equivalent model of the array shown in FIG. 13D. The input source 1751, input switch 1752, output switch 1755, and signal detector 1756 are as illustrated in FIG. 13D. The switch impedance Zs is designed to be a close match with the reference impedance of the signal path Zo, and the assay impedance $Z^{I,J}$ is designed to be much different than either the switch or reference impedance. Thus, small changes in the assay impedance will dominate the electrical properties of any given row, and will therefore be easily detectable. The exact values for the impedances will depend on the design criteria for the particular array, but certain general principles of engineering apply, such as the greatest efficiency in terms of delivering power to the load (detector) is obtained with matched-impedance design, and reference impedances are frequently taken to be 50 Ω.

In an alternative embodiment, each array element may consist of a logic gate which is capable of occupying one of two possible states, depending on the conditions of gating. As an example, the conditions of gating may be whether or not a particular binding event has occurred. Such a condition may be the hybridization of nucleic acid material to specific capture probes on the surface of the device, or a particular drug-receptor interaction. In any case, the device is engineered so that a binding event or structural change in the MBR triggers the gating. Essentially the modulation of any circuit parameter may trigger the gating; all that is required is to have the necessary hardware and software in place to make the decision as to whether or not the circuit parameter has been modulated.

As an example, one may monitor a characteristic frequency of a given system such as a resonant structure. The shift in this frequency as a result of a particular binding event may serve as the modulation which signals the logic state. Any parameter which changes as a function of binding may be used to trigger logic gate. Such parameters include, but are not limited to: frequency, voltage, current, power, phase, delay, impedance, reactance, admittance, conductance, resistance, capacitance, inductance, or other parameters.

Figure 15F:
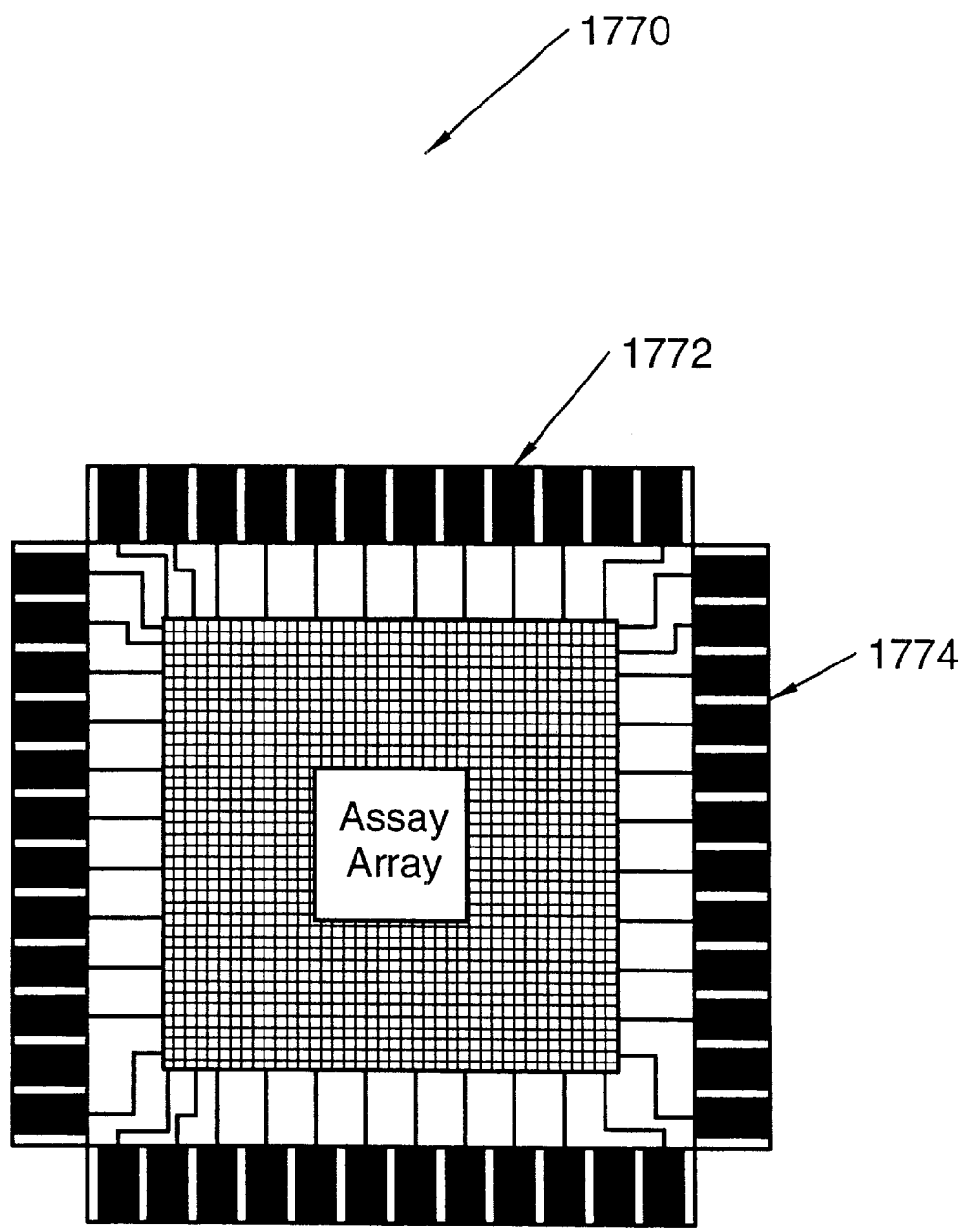
FIG. 15F illustrates one embodiment of a two-dimensional bio-assay array in accordance with the present invention.

FIG. 15F illustrates one embodiment of a two-dimensional bio-assay array 1770. As shown, the array 1770 includes a first input/output (I/O) axis 1772 and a second I/O axis 1774 for inputting/outputting test signals.

The array is interfaced with conventional external diagnostic hardware which is capable of generating and detecting the appropriate frequency or frequencies, then communicating it to and from the assay array via a multiplexer, through the ports as illustrated above. Such an externally supported system may be comprised of any number of electromagnetic sources such as vector and scalar network analyzers, time-domain devices like TDR analyzers and other pulsed techniques; utilize any of the detection schemes mentioned herein, including vector and network analyzers; and use any number of well-known techniques to deliver the signals to and from the assay array via standard and non-standard multiplexing techniques.

Generically, such a chip may be fabricated using standard semiconductor chip approaches. Those of skill in the art will readily appreciate that such a configuration may be used in a one-port format, a two port format, or utilize more than two ports.

The bio-electrical interface region consists of a signal path designed to support the propagation of an electromagnetic signal at the desired test frequency. Many configurations are possible, one example being a sputtered gold transmission line operable up to 110 GHz. In another embodiment, the signal path consists of a dielectric medium, such as the MBR itself. In this embodiment, the signal path blocks DC voltages and currents but otherwise supports the propagation of the desired test signal, occurring at frequencies, for instance 1 MHz, 5 MHz 10 MHz, 20 MHz, 45 MHz, 80 MHz, 100 MHz, 250 MHz, 500 MHz, 750 MHz, 1 GHz, 2.5 GHz, 5 GHz, 7.5 GHz, 10 GHz, 12 GHz, 18 GHz, 20 GHz, 22 GHz, 24 GHz, 26 GHz, 30 GHz, 33 GHz, 40 GHz, 44 GHz, 50 GHz, 80 GHz, 96 GHz, 100 GHz, 500 GHz, 1000 GHz, or frequencies ranging therebetween. Accordingly, the signal path is designed using high frequency circuit design techniques, known in the art. Such design techniques include impedance matching the signal path to the interconnecting structures, minimizing the insertion loss of the signal path, and minimizing the Voltage Standing Wave Ratio (VSWR) of the signal path. In the preferred embodiment of the present invention, the signal path and MBR are oriented in a non-orthogonal orientation.

The present invention is not limited to the detection of a molecule of an anticipated size or structure attached to the signal path. The MBR may consist of 1, 2, 3, 4, 5, 10, 20, 30, 50, 100, 1000, or more molecular lengths attached or separated from but coupled to the signal path. Further, the MBR may consist of a multiple layers of homogeneous molecules, a single but heterogeneous molecular layer or multiple heterogeneous molecular layers.

Additional information regarding arrays of the present invention is set forth in a copending and commonly owned U.S. application entitled "Test Systems and Sensors for Detecting Molecular Binding Events", which was filed concurrently herewith and which was previously incorporated herein by reference in its entirety for all purposes.

VII. Attachment of Proteins to Transmission Line

The transmission line is generally constructed of materials which exhibit appropriate conductivity over the desired test frequency range and which possess good molecular binding qualities as described above. Such materials include, but are not limited to gold, indium tin oxide (ITO), copper, silver, zinc, tin, antimony, gallium, cadmium, chromium, manganese, cobalt, iridium, platinum, mercury, titanium, aluminum, lead, iron, tungsten, nickel, tantalum, rhenium, osmium, thallium or alloys thereof. The conductive layer may also be formed from semiconducting materials which may be either crystalline or amorphous in structure, including chemically doped or pure carbon, silicon, germanium, gallium-arsenide, idium-gallium arsenide, glass, quartz, ceramics, or the like. The conductive material may also be formed from polymers including, without limitation, polyethylene, polypropylene, polyacetylene, polythiophene and the like.

In one embodiment, the transmission line is gold. One method for fabricating a gold transmission line is as follows. A support material such as glass or other inexpensive, relatively smooth material is used as the underlying physical structure. On top of this material, a thin layer of titanium (10–100 Angstroms) is deposited through thermal evaporation, sputtering, chemical vapor deposition or other means. The titanium acts as an adhesive layer between the gold and support. Subsequent to titanium deposition, gold (10–10000 Angstroms) is deposited through thermal deposition, sputtering, chemical vapor deposition, or like methods.

In certain embodiments, targets may be attached to the transmission line directly or via various linkers. Attachment may include electrostatic interactions, covalent bonds, and hydrophobic interactions, for example. Often targets can be attached directly because many biological molecules contain functional groups which can be used to form the attachment; the particular procedure varies according to the chemical structure of the particular molecule (for example, a protein, antibody, glycoprotein, nucleic acid, lectin, sugar, carbohydrate, etc.) being attached to the surface. For example, polypeptides typically contain variety of functional groups, e.g., carboxylic acid (COOH) or free amine (—$NH_2$) groups, which are available for reaction with a suitable functional group on the surface of the transmission line or to a suitable linker. Similarly, other biological molecules such as nucleic acids, sugars, and carbohydrates, for example, contain other functional groups (e.g., —OH, —NH2, —COOH, —SH, etc.) that are suitable points for attachment.

Alternatively, the target can be derivatized to expose or attach additional reactive functional groups. Derivatization can involve chemical treatment of the target or transmission line. For example, a silica or glass substrate can be silanized to create functional groups thereon. Similarly, a glycoprotein, can be derivatized, e.g., by glycol cleavage of a sugar moiety attached to the protein antibody with periodate to generate free aldehyde groups. The free aldehyde groups on the glycoprotein may be reacted with free amine or hydrazine groups at the surface to bind the binding partner thereto (see U.S. Pat. No. 4,671,958). Procedures for generation of free sulfhydryl groups on polypeptide, such as antibodies or antibody fragments, are also known (see U.S. Pat. No. 4,659,839).

Instead of being directly attached, targets can be attached via one or more linkers as shown in FIGS. 1D–1F and described in the accompanying text. A linker is a molecule that may be used to join the biological binding partner (e.g., ligand or antiligand) to the underlying (e.g., apparatus or device) surface. The linker is capable of forming covalent bonds with a nucleic acid and the transmission line. A bifunctional linker having one functional group which can react with a group on the surface of the transmission line, and another group reactive with the nucleic acid can be used to form the desired conjugate. Many procedures and linker molecules for attachment of various biological molecules to various metal, glass, and plastic substrates are known in the art. See, for example, European Patent Application No. 188,256; U.S. Pat. Nos. 4,671,958; 4,659,839; 4,414,148; 4,699,784; 4,680,338; 4,569,789; 4,589,071 and 5,670,381; and Borlinghaus et al., Cancer Res. 47: 4071–4075 (1987), each of which is incorporated herein by reference.

Proteins can be attached to the transmission line using a variety of different protocols. In some instances, proteins can be attached without modification of the protein or transmission line. For example, a solution of protein is prepared in a standard buffer and the solution contacted with the bare gold followed by washing. Another approach involves applying a hydrophobic compound, such as an alkane thiol, to the gold surface (see for example, Bain, et al., Angew. Chem. 101:522–528, (1989)). Proteins can also be attached using a variety of homofunctional and biofunctional linkers (see for example, Pierce Catalog and Handbook, Life Science and Analytical Research Products, 1994).

Alternatively, proteins can be engineered to include a linkage site which facilitates attachment to a transmission line. Preferably, the linkage site is engineered so that it does not interfere with protein binding function. The linkage site may be engineered to control the direction in which the protein is oriented once it is attached to the transmission line. Examples of this general approach include engineering the linkage site to include a relatively high concentration of cysteines (and thus a high thiol concentration) or amino groups to facilitate attachment. It is also possible for the site to be engineered so that a second protein is attached at a linkage site and it is the second protein which is actually connected with the transmission line. A variety of other such approaches are known in the art.

Methods of conjugating antibodies, proteins, and glycoproteins abound in the immunotoxin literature and can be found, for example in "Monoclonal Antibody-Toxin Conjugates: Aiming the Magic Bullet," Thorpe et al., Monoclonal Antibodies in Clinical Medicine, Academic Press, pp. 168–190 (1982); Chapter 4 in *Monoclonal Antibodies: Principles and Applications*, Birch and Lennox, Eds., John Wiley & Sons, Inc., N.Y. (1995); Waldmann, Science, 252: 1657 (1991), U.S. Pat. Nos. 4,545,985 and 4,894,443.

VIII. Label Free Detection

The methods of the present invention are capable of detecting the formation of protein/ligand complexes without having to utilize labels. This is true regardless of the type of ligands involved in the binding event being analyzed. Most existing methods, in contrast, require the use of labels to detect the formation of binding complexes. The types of labels used in existing methods vary, but frequently include radioactive labels or fluorescent labels.

Because the methods of the present invention involve direct detection, it is not necessary to use labeled compounds. Hence, in the particular case of methods for analyzing protein/ligand complexes, it is unnecessary to prepare labeled proteins or ligands to conduct an experiment, thus simplifying the procedure and reducing costs. Not having to use labels also insures that there is no steric hindrance caused by the presence of the label which might interfere with the formation of the protein/ligand complex. Furthermore, unlike most other methods, the methods described herein are insensitive to background signal resulting from unbound labeled molecules (e.g., background fluorescence resulting from unbound ligand). This means that the methods of the present invention can monitor the formation of the protein/ligand complex in real time, thereby allowing kinetic studies to be undertaken. Although labels are not necessary with the present invention, the nature of the detection system does not preclude their use.

IX. Analysis Using Protein/Ligand Profiles
A. Acquiring a Profile or Signature With the detection system of the present invention it is possible to obtain spectral scans which include signals that are characteristic for certain ligand/antiligand complexes or for certain types of binding interactions. Such scans are referred to herein as profiles, signatures or fingerprints. Profiles can be obtained for essentially any type of ligand/antiligand complex. Such profiles are particularly useful in studying protein/ligand complexes. As described in greater detail below, profiles can be used in identifying the formation of a particular complex, classifying ligands according to the type of binding interaction, and distinguishing between different types of binding interactions.

Hence, certain methods of the present invention include determining the profile or signature for various types of ligand/antiligand complexes, in particular, various types of protein/ligand complexes. Within the context of protein binding studies, such a process typically involves monitoring an electromagnetic signal transmitted down a signal path to which a protein target bound to a ligand is coupled. Modulations of a signal (transmitted and/or reflected) are measured as either the frequency or wavelength is scanned over a desired range to obtain a spectrum which depicts the measured signal as a function of frequency or wavelength. Since each protein/ligand complex gives a different spectrum, the spectrum can serve as a signature or profile for that particular complex.

For example, it is possible to identify certain peaks or signals at particular frequencies in the spectrum which are unique to a particular protein/ligand complex. Likewise, certain signals can be correlated with particular substructures, for example, domains, binding sites, active sites, allosteric sites, etc. Thus, by detecting and monitoring such characteristic peaks, it is possible to conduct a variety of analyses including, for example, unambiguously identifying the presence of certain analytes in a sample, distinguishing between the types of binding interactions, conducting quantitative studies and performing kinetic studies.

By repeating this procedure and analysis with numerous different protein/ligand complexes, a database of signatures or profiles can be accumulated. By storing these profiles in an electronic storage medium for example, the profiles can be rapidly accessed during an experiment and compared to an experimental spectrum to aid in the types of analyses just listed.

X. Quantitative Analysis

Because the detection methods can be performed without labels (as described above, thus allowing signals to be monitored in real time) and because it is possible to correlate certain signals with particular protein/ligand complexes (i.e., to identify characteristic signals in the profile or signature of the spectrum for the protein/ligand complex), it is possible to perform certain quantitative analyses. For example, the concentration of a particular complex can be measured with time from changes in certain signals in the spectrum known to arise from a particular protein/ligand complex. Changes which can be measured include changes in peak amplitude or changes in peak frequency, for example, although other changes could be monitored as well.

Association kinetics can be performed by monitoring signals characteristic for a particular protein/ligand complex. In such studies, change in signal intensity, for example, is plotted as a function of time to obtain an association curve. Affinity constants can be determined from multiple association curves obtained at different ligand concentration levels. Affinity constants and other kinetic data can be calculated according to methods which are known in the art. References for kinetics and affinities can be found in any standard biochemistry or chemistry text such as Mathews and van Holde, *Biochemistry*, Benjamin Cummings, N.Y., 1990.

XI. Library Synthesis

A variety of different types of libraries can be used with the methods of the present invention. Libraries are intentionally created collections of different molecules which are prepared using organic synthetic methods or biochemically. In the latter case, the molecules can be made in vitro or in vivo. A non-exhaustive list of such libraries includes random peptide libraries, combinatorially synthesized libraries, phage display libraries, natural product libraries, oligosaccharide libraries and legacy libraries (a collection of molecules synthesized over time and collected, such as by a group of chemists at a particular research facility for example).

Biologically synthesized libraries constructed using techniques of molecular biology in bacteria or bacteriophage particles can also be used to prepare libraries for use in the present invention. For example, U.S. Pat. Nos. 5,270,170 and 5,338,665 (both of which are incorporated herein by reference in their entirety) describes the construction of a recombinant plasmid encoding a fusion protein created through the use of random oligonucleotides inserted into a cloning site of the plasmid. This cloning site is placed within the coding region of a gene encoding a DNA binding protein, such as the lac repressor, so that the specific binding function of the DNA binding protein is not destroyed upon the expression of the gene. The plasmid also contains a nucleotide sequence recognized as a binding site by the DNA binding protein. Thus, upon transformation of a suitable bacterial cell and expression of the fusion protein, the protein binds the plasmid which produced it. The bacterial cells are then lysed and the fusion proteins assayed for a given biological activity. Moreover, each fusion protein remains associated with the nucleic acid which encoded it; thus through nucleic acid amplification and sequencing of the nucleic acid portion of the protein/plasmid complexes which are selected for further characterization, the precise structure of the candidate compound can be determined.

Other libraries often called display libraries can also be used. These libraries are prepared using nucleic acid vectors wherein a random oligonucleotide is fused to a portion of a gene encoding the transmembrane portion of an integral protein. See, for example, U.S. Pat. No. 5,223,408, which is incorporated herein by reference. Upon expression of the fusion protein it is embedded in the outer cell membrane with the random polypeptide portion of the protein facing outward. Thus, in this sort of library, the compound to be tested is linked to the cell itself. Since the cell also contains the recombinant vector encoding the random portion of the fusion protein, cells bearing random polypeptides which appear promising in a preliminary screen can be lysed and their vectors extracted for nucleic acid sequencing, deduction of the amino acid sequence of the random portion of the fusion protein, and further study.

Similarly, random peptide libraries can be generated using phage display technology. In general, this approach involves batch cloning millions of variants of proteins or fragments thereof into a phage genome as a fusion to a gene encoding one of the phage coat proteins. Once expressed, the coat protein fusion products are incorporated into new phage particles that are assembled in the host bacterium. Subsequent incorporation of the fusion protein into the mature phage coat protein causes the ligand (e.g., peptide or peptide fragment) to be presented on the phage surface, while the corresponding genetic material resides within the phage particle. This connection between displayed ligand and ligand genotype makes it possible to enrich for phage which display a ligand that binds a target of interest. For reviews of this approach, see for example, Phizicky and Fields, Microbiological Reviews, 59:94–123 (1995) and Hoogenboom et al., Immunotechnology 4:1–20 (1998), both of which are incorporated herein by reference in their entirety. See also, Devlin et al., Science 249:404–406 (1990); Scott and Smith, 249:386–390 (1990); Cwirla et al., Proc. Natl. Acad. Sci. USA 87:6378–6382 (1990); Fong, et al., Drug Development Research, 33:64–70 (1994); Smith and Scott, Methods of Enzymol. 217:228–257 (1993); Smith, Science 228:1315–1317 (1985); Sawyer et al., 4 Protein Engineering 947–53 (199); Takamatsu et al., 151 J. Immunol. 4651–59 (1993), and Dower et al., U.S. Pat. No. 5,427,908, each of which is incorporated herein by reference in its entirety.

Combinatorial chemistry is a synthetic strategy in which the chemical members of the library are made according to a systematic methodology by the assembly of chemical subunits. Each molecule in the library is thus made up of one or more of these subunits. The chemical subunits may include naturally-occurring or modified amino acids, naturally-occurring or modified nucleotides, naturally-occurring or modified saccharides or other molecules, whether organic or inorganic. Typically, each subunit has at least two reactive groups, permitting the stepwise construction or larger molecules by reacting first one then another group of each subunit to build successively more complex and potentially diverse molecules. Through use of design strategies in which a fixed number of individual building blocks, for example, the twenty naturally-occurring amino acids, are made equally available at each stop of the synthesis, a very large array or library of compounds can be assembled after even a few steps of the synthesis reaction.

One general combinatorial approach involves chemically synthesizing the combinatorial libraries on solid supports in a methodical and predetermined fashion, so that the placement of each library member gives information concerning the synthetic structure of that compound. See, for example, U.S. Pat. No. 4,833,092; WO94/05394; and Geysen et al. J. Imm. Meth. 102:259–274 (1987), each of which is incorporated herein by reference in its entirety. Other approaches involve a combination of standard solid-phase protein chemistry and photolithography using photoliable protecting groups. See for example, U.S. Pat. No. 5,143,854 to Pirrung; WO 90/15070; WO 92/10092; and Fodor, et al., Science 251:767–773 (1991), each of which is incorporated herein by reference in its entirety.

XII. Screening/Drug Discovery
A. General

Current drug discovery programs typically involve an iterative process in which large libraries are screened to identify ligands that bind a target of interest which are then used to prepare more focused libraries that are subjected to further screening. For such an approach to work well, it is necessary to have a rapid screening protocol. A limitation of many screening methods is that it is not possible to detect target/ligand complexes directly. Instead, it is typically necessary to use labels to identify binding complexes. Furthermore, it usually is not possible to distinguish between specific and non-specific binding. Thus, focused libraries often include ligands that bind non-specifically to the target, even after multiple rounds of screening. A further limitation is that many screening methods are separation based approaches involving a washing step to physically separate the bound ligand from free rather than homogeneous assay wherein a separation step is not necessary.

B. Screening to Identify Ligands that Bind

Most existing methods for screening for ligands that bind proteins simply involve detecting ligands that bind to the protein of interest. Ligands identified during the initial round of screening are subjected to subsequent rounds of screening to develop a more focused library from which potential lead compounds can be selected.

The methods of the present invention can also be used in screening protocols in which screening simply involves detecting binding between a protein of interest and a ligand. In general, such methods involve coupling a protein target to a signal path and then contacting the protein target with a sample containing a ligand. A signal is propagated along the signal path, followed by the detection of a response signal resulting from modulation of the test signal by the protein/ligand complex. The protein target is directly attached to a continuous transmission line in some methods. In other methods, a ligand(s) is coupled to the signal path and a protein target is contacted with the ligand. As described above, the ligand used in this assay can be virtually any compound capable of binding a protein including, for example, antibodies, peptides, nucleic acids, whole cells, cell surface receptors, vesicles, lipids, and the like.

C. Screening Based Upon Biological Function

The detection system of the present invention can be used to conduct a variety of screening assays to identify molecules which affect some type of biological activity or function. For example, it is possible to screen for ligands that affect the binding between a protein target and another compound, such as binding between the protein target and another protein, a nucleic acid, or a cell. In one approach, a variety of different test ligands (typically from a library) are each individually mixed with a ligand known to bind to the target protein. This mixture is then contacted with the target protein coupled to the signal path of the bio-assay device. The detection of a response signal for the target protein/known ligand indicates that the test ligand does not significantly affect binding; the absence of a response signal, on the other hand, indicates that the test ligand is capable of inhibiting binding between the target protein and known ligand.

Thus, in the instance in which a screen is conducted to identify ligands that disrupt binding between a particular target protein and a known nucleic acid that binds the target protein, a sample containing the known nucleic acid is mixed with a test ligand. This resulting mixture is then contacted with the target protein coupled to the signal path. A signal is transmitted along the signal path to interact with any complexes formed between the target protein and nucleic acid. Detection of a response signal indicates that the test ligand does not prevent the target protein from binding the nucleic acid; absence of the expected signal indicates that the test ligand prevents binding and thus may potentially have useful biological activity. In an alternate approach, the target protein and the known ligand are mixed together first to form a binding complex and the test ligand subsequently added. Loss of the response signal indicates that the test ligand destabilizes the binding complex involving the target protein and known ligand.

Another example of a screening assay involving detection of binding that correlates with biological activity is one in which the ability of a test ligand to actually transduce a signal through a biological receptor is screened for (see, for example, WO 98/25146, which is incorporated herein by reference in its entirety). In this type of assay, a detectable binding complex is only formed if a test ligand is able to bind to a receptor in a cell and trigger the expression of a reporter molecule which then binds to form the detectable binding complex.

A wide variety of other such screening mechanisms which involve assaying for the formation of binding complexes with biological activity can also be developed as would be appreciated by those with skill in the art.

D. Screening using Profiles or Signatures

1. Specific v. Non-Specific Binding

Many current screening approaches are limited in that they simply indicate whether a test ligand binds to a target protein. Such information is of somewhat limited value in screening for test ligands that have real biological relevance because it is impossible to distinguish between specific and non-specific binding. Although certain methods such as that just described for assaying test ligands for the ability to bind to a cell receptor and trigger expression have been developed, these assays tend to be quite complex and time consuming.

Some methods of the present invention, in contrast, are capable of distinguishing between specific and non-specific binding as generally described above. The ability to make such a distinction is of great value in more rapidly identifying test ligands that bind to biologically relevant sites on the target protein. Methods capable of making the distinction utilize the profiling or signature based methods described above. In screening methods involving proteins and ligands capable of binding thereto, a profile is obtained for a target protein and a natural ligand known to form a specific binding complex. From such a profile, it is possible to identify signals which are characteristic for specific binding as described above. Thus, during a screening experiment, certain methods of the present invention are able not only to simply identify those test ligands which bind to the target protein, but to also identify from the group of ligands that bind those which bind at the site at which natural ligands bind. The ability to make such distinctions makes it possible to much more rapidly focus in on those test ligands that are likely to be of the most value.

2. Classification by Nature of Interaction

With certain methods of the present invention it is possible to screen at a more advanced and biologically relevant level than even distinguishing between specific and non-specific binding. Again, using the approach described above for obtaining profiles or signatures, it is possible using the methods of the present invention to identify signals which are characteristic for the specific type of interaction which exists between the target protein and a bound ligand. Thus, with certain methods, it is possible not only to identify whether a ligand is specifically bound at the site to which a natural ligand binds, but further possible to distinguish the nature of the interaction. Thus, some methods involve screening for ligands that not only bind specifically, but which also bind with the target protein in a specific way.

For example, in certain methods it is possible to identify a signal or set of signals that is characteristic for the binding of various agonists to a target protein. This set of signals or set of signals is useful in examining an experimental spectrum between a target protein and a test ligand for the presence of the signal or set of signals that is characteristic of agonist binding to the target protein. The presence of such a signal or set of signals indicates that the test ligand is an agonist. Similar types of analyses can be conducted using signals which are characteristic of inhibitors binding to a particular target protein. Such signals can be used to screen a library of test ligands for signals characteristic of inhibition complexes for the particular target protein, indicating that such a test ligand is a strong candidate to inhibit the target protein.

It is even possible with certain methods to distinguish between related types of ligands, for example to distinguish between agonists and antagonists and between competitive inhibitors and allosteric inhibitors. For example, since agonists and antagonists induce different conformational structures in the target protein upon binding, it is possible to identify a signal or set of signals which is characteristic for the binding of an agonist with a particular target protein and another signal or set of signals which is characteristic for antagonist binding. An experimental spectrum can thus be examined for the presence of the agonist or antagonist signals to determine whether a test ligand that binds appears to be an agonist or antagonist. Similar types of studies can be used to distinguish and screen for competitive inhibitors and allosteric inhibitors. A variety of other types of distinctions can be utilized to make similar types of highly sophisticated screening analyses to identify only those ligands which are likely to be the most biologically relevant.

3. Multi-Site Proteins

Some protein targets have multiple active sites or multiple sites at which ligands can bind, thus altering the conformation of the protein and inducing a physiological effect. The physiological effect may be unique for each binding site. Conventional technologies such as fluorescence can only identify a binding event; with conventional approaches it is difficult to distinguish between binding at the various sites. With the methods of the present invention, however, it is possible to distinguish between binding at different sites because the methods are sensitive to structural features and changes which alter the dielectric properties of the binding complex. In particular, it is possible using the methods described above to identify certain signals which are characteristic of binding at the various sites. With knowledge of such signals, it is possible to distinguish between binding events at the various sites.

E. Screening Orphan Receptors

"Orphan receptors" is a term used in the art to refer to receptors for which no known ligands have been identified. Studies on such receptors is complicated with many existing methods because the methods frequently involve competitive binding studies to identify those test ligands which are capable of binding the protein target of interest. In a competitive binding assay, a labeled ligand capable of binding a target protein competes with a test ligand for binding to the target protein. From knowledge of the amount of labeled ligand present and the amount bound, it is possible to generate standard curves which can be used to assess the ability of the test ligand to bind to the target protein.

Such competitive studies, however, are not possible with orphan receptors, because by definition a ligand capable of binding to the protein target is not known. With the methods of the present invention, in contrast, ligands capable of binding to orphan receptors can be identified because it is possible with the methods of the present invention to directly monitor binding between a target protein and ligand without the use of labels.

XIII. Screening Using Arrays

A. Methodology

Certain methods of the present invention utilize arrays to conduct the screening process. The use of arrays makes it possible to greatly increase sample throughput. Structurally, the array is typically formed on a solid support that includes multiple elements or sites. In the screening methods of the present invention, each element of the array includes a signal path such as a transmission line to which a protein target or ligand is electromagnetically coupled or directly attached. In many screening tests, the goal is to screen a large number of compounds against one protein target. Thus, in such methods, all the protein targets located within any element, as well as all the targets at different elements, are the same. Each element is contacted with different samples, each sample containing a different compound. In this way, it is possible to screen the different compounds in a library with a common target.

In other methods, however, it may be desirable for all the protein targets in any particular element to be the same, but for the protein targets in different elements to vary from one another. This allows one test ligand or group of ligands to be screened against several different protein targets. So, for example, assuming ten different protease inhibitors are used as targets, the array would preferably include ten rows or columns of elements, each element having a different protease.

Regardless of the identity of the targets at the various array elements, a signal is launched down the signal path running to each element to monitor binding at each of the various elements. Modulations in the launched signal are used to detect binding between the target and a ligand in the sample. An array may be used in conjunction with a microfluidic device to controllably add microquantities of different samples to the different arrays. In the situation in which all the targets are identical, typically the fluidic device is used to dispense different samples to the various arrays; whereas, when the protein target in the various elements vary, the fluidic device dispenses the same sample to the different elements of the arrays.

Some methods utilize arrays synthesized on a solid support as described above. In certain methods, it is possible to focus the screening process towards ligands more likely to have a desired biological activity by utilizing the sequence of a ligand known to bind to the protein target of interest (a "lead sequence") to inform the selection of sequences synthesized on the array to be used in subsequent rounds of screening. See, for example, U.S. Pat. No. 5,770,456, which is incorporated herein by reference in its entirety. Thus, a series of ligands related to the lead sequence are synthesized by making systematic variations at one or more positions of the lead sequence. The theory is that minor alterations of a sequence (e.g., a peptide) known to bind a target protein may result in a sequence with even higher binding affinity.

B. Array Design

The number of elements in an array varies widely, based primarily on the type of screening application for which the array is to be used. In the initial stages of screening of a library, for example, a large number of elements is preferred so that a large number of compounds can quickly be screened. Arrays for such applications can have up to $10^6$ elements. In other instances, there are up to $10^3$ elements in the array. In yet other methods, there may only be a single element, such as when it is desired to conduct higher resolution studies with a compound that appears from initial rounds of screening to be a good candidate for a lead compound having potential therapeutic value. Hence, in general, the number of elements in the array can be 1, 10, $10^2$, $10^3$, $10^4$, $10^5$, or $10^6$, or any number or range therebetween.

The density of the protein target or ligands that make up the array can also vary significantly. The density required varies on various factors such as the degree of signal sensitivity, the number of ligands in solution and whether characteristic peaks for a particular complex under study are well-defined and are resolved from signals from other complexes. In the optimal situation, the sensitivity of the present system and the ability to conduct analyses using signals known to be correlated with certain complexes means that an element may contain a single protein target or ligand. In other situations, however, the density of protein targets or ligands may be up to 100 targets/cm$^2$. In still other, methods, the density may be up to $10^8$ targets/cm$^2$, up to $10^{12}$ targets/cm$^2$ and up to $10^{18}$ targets/cm$^2$. Hence, in general the number of targets can include 1 target/element, or up to $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ targets/cm$^2$, or any number therebetween.

C. Coupling of Arrays and Microfluidic Devices

It is possible through the use or array and microfluidic technology to use the methods described herein in a high throughput screening process (HTS). In such an approach, hundreds of thousands of compounds are screened for their ability to bind a particular target or screened according to the higher levels of analysis described above. For example, the invention described herein can be miniaturized, so that highly parallel screening platforms can be realized; platforms which are capable of screening hundreds or thousands of compounds simultaneously, and at the same time determining the effect of binding (e.g. agonist or antagonist), affinity, kinetics, etc. Additionally, such miniature systems require very small amounts of compound, thus greatly saving costs in purchasing said compounds from combinatorial libraries.

The system of detection formed through use of the bio-assay device provides a high throughput detection system because detection optionally occurs in real time and many samples can be rapidly analyzed. The response period is optionally monitored on a nanosecond time scale. As soon as the molecules are bound to each other, detection occurs. More time is optionally required to measure low concentrations or binding events between molecules with a low binding affinity. The actual time is optionally limited by diffusion rates. Other than these potential limitations, thousands of compounds are optionally run through the system very quickly, for example, in an hour. Using chip fabrication technologies, a 10,000 channel device (using some of the emerging microfluidics technologies) can be manufactured. Using small volumes to minimize diffusion times and making kinetic measurements at only the start of the binding reaction, 10 million samples per hour are optionally measured. With known concentrations, the binding affinity is optionally calculated from the kinetics alone and thus the device can be probed at a very fast time scale and the affinity calculated and/or estimated from the slope of the kinetic curve.

XIV. Focused Screening

In the most straightforward approach, the initial rounds of screening simply involve identifying which ligands in a library bind to a protein of interest. In some instances, this initial group of ligands is then tested a second time to confirm the results from the first round of screening. The resulting subgroup of ligands that demonstrate reproducible binding are then typically subjected to a dose response test. In a dose response test, different concentrations of ligand are contacted with a constant number of protein targets and the resulting signal for the binding complexes measured. A plot of a signal parameter (e.g., intensity of a particular peak(s)) versus concentration is prepared. A good dose response yields a sigmoidal curve in which typically there is little signal response at very low concentrations of ligand, a rapid change in signal at higher concentrations and then finally a plateau in the signal as the protein target becomes saturated.

The dose response should have good dynamic range, such that at certain concentrations there is a significant change in signal with a relatively small change in concentration. Otherwise it is necessary to give large amounts of the ligand in order to achieve the desired physiological response. At higher concentrations, the risk of unwanted side effects and toxicity increases. Dose response studies can be conducted using arrays. In such instance, for example, solutions having different concentrations of ligand can be exposed to different elements in the array, each array having the same number of peptide targets. If the number of protein targets varies from element to element, it is necessary to normalize the results for the different elements.

Those ligands exhibiting good dose response typically are then used as the basis for synthesizing various analogs. The analogs are then subjected to additional rounds of screening to identify strong binding ligands and form a more focused collection of ligands that potentially have therapeutic value.

Screening approaches using signatures or profiles significantly streamlines testing and reduces excessive rounds of screening. In such methods, the initial screening round involves classifying ligands as either specifically or non-specifically binding to the target protein, or classifying the ligands according to structural features, for example. Thus, in the initial screening process, only those ligands which are within the desired class are selected out. Thus, if the screening process is to identify agonists, the spectra are examined for signals that are characteristic of agonists. By excluding all ligands which fail to show signals characteristic for agonist binding, a much greater percentage of the ligands in the library can be ignored. Through the use of profiles, not only is it possible to exclude compounds that simply do not bind, but also possible to eliminate certain ligands which form binding complexes but are of the wrong type. This more focused group of ligands can then be subjected to the dose response, synthesis and additional screening tests set forth above to identify ligands showing therapeutic promise. By using more selective criteria in the screening process, it is possible to much more quickly identify ligands of potential value as therapeutic agents.

XV. Antibodies

A. General

The present invention provides a variety of methods using antibodies or fragments thereof that can be used in a variety of analytical and diagnostic applications. The methods can utilize complete antibodies or any of a variety segments thereof such as $F(ab)'_2$, Fab, or scFv fragments. As used herein, the term antibody includes such fragments.

Traditional studies using antibodies such as competitive binding studies, ELISA (enzyme linked immunosorbent assay), and sandwich type assays, for example, often involve complex procedures to detect the presence of an antigen or antigen/antibody complex and almost always involve the use of labels. As indicated above, the methods of the present invention involve the direct detection of ligand/antiligand complexes, hence greatly simplifying and increasing the rate at which analyses can be performed.

B. Attachment to Transmission Line

In general, the chemistry for attaching an antibody to the transmission line is the same as described above for the attachment of proteins generally to the transmission line. However, in those instances in which an antigen rather than an antibody is attached to the transmission line, it may be desirable to attach the antigen to the transmission line via a linker, especially when the antigen is a small molecule, in order to get the antigen out from the transmission line so it can be bound by an antibody. In other instances, the antigen can be bound to a macromolecule such as a protein (e.g., BSA) which is then attached to the transmission line.

C. Diagnostic Applications

1. General

The present invention provides methods for conducting diagnostic tests to identify the presence of a particular antigen or antibody of medical relevance. In general the methods involve contacting a known antibody that is coupled to a portion of a signal path with a sample that potentially contains a antigen that specifically binds with the known antibody. The formation of a binding complex is detected by generation of a response signal. Detection of a response signal is indicative of the presence of the antigen in the sample, and failure to detect a response signal indicates that the antigen is not present in the sample. It is also possible to alter the analysis by coupling a known antigen to the signal path and examining a sample for the presence of an antibody which forms a specific complex with the antigen.

2. Potential Antigens

Potential antigens which are of potential medical significance and that can be assayed for using the methods described herein broadly include, for example, peptides, oligosaccharides, steroids, nucleic acids and cells or cell components. The methods can be important in monitoring pathogens such as viruses or bacteria, metabolites and catabolites such as glucose, lipids, liver enzymes, electrolytes, electrolytes, clotting factors. One important class of molecules that can be detected include tumor markers. Such tumor markers may include markers such as CEA (chorio embryonic antigen) or PSA (prostrate specific antigen), as well as a wide variety of other markers.

Another group of potential ligands that can be detected include drugs of abuse and their metabolic byproducts such as cotinine, cocaine, benzoylecgonine, benzodizazpine, tetrahydrocannabinol, nicotine, ethanol. Similarly, the presence of therapeutic drugs including, for example, theophylline, phenytoin, acetaminophen, lithium, diazepam, nortryptyline, secobarbital, phenobarbitol, and the like can be detected.

Hormones constitute another broad category of ligands that can be detected, a non-exhaustive list including growth factors such as testosterone, estradiol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, and sex hormone binding globulin. Other possible molecules which can be assayed for include glucose, cholesterol, caffeine, corticosteroid binding globulin, DHEA binding glycoprotein, and the like.

In addition to small molecules, a variety of larger molecules, even cells and cell components can be detected. For example, the presence of infectious pathogens such as viruses, bacteria, fungi and the like, can be detected and quantified. Binding is often through a characteristic surface marker (for example, membrane receptor or lectin) that can interact with an antibody. Examples of pathogens include, *Helicobacter pylori*, hepatitis (e.g., hepatitis A, B and C), measles, mumps, and rubella. It is also possible to detect the presence of an HIV protein in a patient's blood. Similarly, cell types (e.g. cells characteristic of a particular tissue) having characteristic markers (e.g. tumor cells overexpressing IL-13 receptor (see, e.g., U.S. Pat. No. 5,614,191)) can be detected. Thus, cells indicative of particular pathologies, particular states of differentiation (or lack thereof) or particular tissue types can be detected and/or quantified. With certain methods, the invention may be easily extended into cell-based assays, since the detection may not require sample purification and amplification. In these classes of applications, cellular systems may be monitored for various changes either by detecting external expressions or by lysing the cell to release the cytosolic constituents and detect the presence of one or more analytes of interest.

When an antigen is coupled to the signal path, various antibodies can be detected. For example, antibodies specific to HIV, specific antibodies like ANA (used in rheumatological disorders) and allergic response antibodies.

3. Use of Arrays

Arrays can be used in diagnostic applications to test for the presence of several antigens or to rapidly test a plurality of samples. However, in general, the number of elements in diagnostic applications tends to be relatively few by virtue of the fact that a relatively few antigens or antibodies are being screened for in a typical analysis. Many methods involve detection of a single antigen or antibody. In such instances, a single element may be sufficient, unless a variety of different samples are each to be screened for the particular antigen or antibody, in which case the array includes multiple elements, each element containing the same antibody or antigen. Alternatively, multiple elements may be desired if several different antigens or antibodies in a single sample are to be assayed. Finally, multiple elements may be desired to include redundant elements to serve as controls. Typically, the number of elements is less than 50, and may be between 1 and 10. However, the limitation on the number of elements in diagnostic methods is a reflection of the nature of the analysis, not the ability to prepare arrays having many more elements as set forth in the drug screening section above.

The number of antibodies or antigens within any given element depends upon the same considerations and factors describe above in the drug discovery methods.

D. Non-Clinical Applications

Related methods involve the use of antibodies to detect the presence of a variety of ligands in non-clinical applications. In such instances, the methods are used to detect the presence of a particular ligand of interests. For example, the method could be used in waste water treatment analysis. In this case the ligand being detected could be a toxin, a microbial organism or a product generated by a microbial organism.

E. Epitope Determination

Epitopes for antibodies or fragments thereof can be determined according to certain methods of the present invention. One approach involves synthesizing ligands in a systematic way to obtain a diverse set of ligands with varying sequences. These ligands can be synthesized in an array format such as described above and then screened with an antibody of interest. By detecting which ligand or ligands the antibody binds to, it is possible to determine the sequence which the antibody recognizes. A second approach involves the use of profiles. In this instance, a database of profiles for known antibody/antigen complexes is prepared. This database is then analyzed to identify distinct signals associated with particular complexes. Since the epitope sequence is known for the known complexes, it is possible to correlate certain epitopes with certain signals. Thus, in the instance of a test antibody which binds to an unknown epitope, by examining the experimental spectrum for signals characteristic of known epitopes it is possible to identify the epitope that the test antibody recognizes.

The following examples are provided to illustrate certain aspects of the invention and are not to be construed so as to limit the scope of the invention.

EXAMPLE 1

(Signature Profile for Collagenase and Lysozyme)

Tests were conducted using the bio-assay device of as shown in FIG. 2A. The binding surface of the bio-assay device comprised a cover glass treated with ITO deposited via chemical vapor deposition (CVD). The ITO transmission line was carefully examined to ensure that it contained no microfractures or breaks in it. The transmission line was measured with a Tektronix 11801 signal analyzer with a TDR module, and found to have a broadband reference impedance of 32 Ω. The line length was about 2.6 nsec in length, the binding surface was found to have an impedance of 34 Ω, and a length of about 200 psec. Separation between the top and bottom plates was 0.010" (10 mils), and the chamber was one-half inch long. No side walls were used; instead, the capillary action of the top and bottom plates retained the solution in place.

The bio-assay device was then filled with a solution of d-PBS. With the bio-assay device filled, baseline transmission loss ($S_{21}$) and return loss ($S_{11}$) S-parameter measurements were made over a test frequency range from 45 MHz to 1 GHz. A network analyzer manufactured by the Hewlett Packard Company (HP 8510B analyzer with a HP 8516A S parameter test set) was used to both launch, measure and store signals.

Subsequently, a series of experiments to examine the differing responses of different proteins over the frequency range of 1–10 GHz were performed. The same device was used for each experiment (to eliminate small differences in fabrication from one device to another), but was thoroughly washed with SDS between the application of each of the proteins.

Figure 9A:
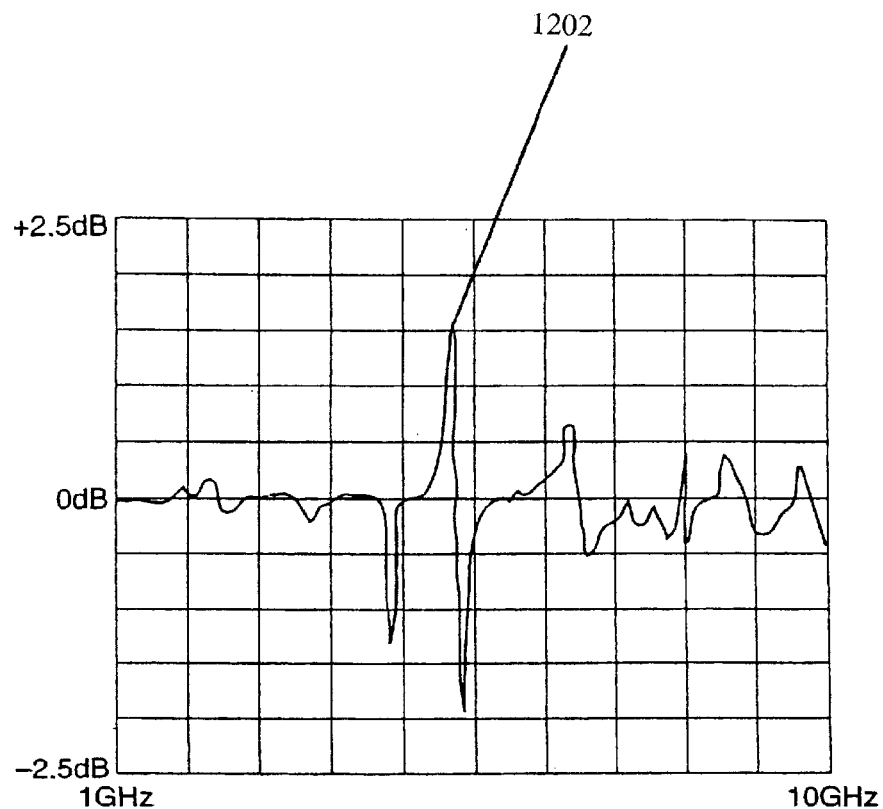
FIG. 9A illustrates the transmission loss measurement of the primary binding effects of collagenase.
Figure 9B:
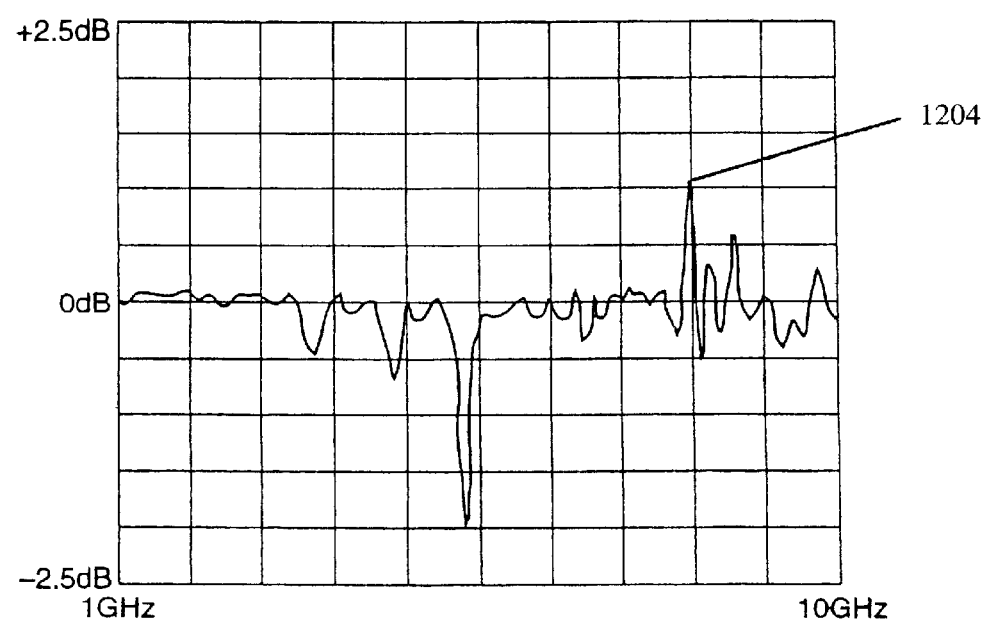
FIG. 9B illustrates the transmission loss measurement of the primary binding effects of lysozyme.

FIGS. 9A and 9B illustrate the transmission loss measurements of the primary binding effects of collagenase and lysozyme samples, respectively, over the test frequency range from 1 GHz to 10 GHz. In both instances, the signal response exhibited a pattern of peaks and valleys which can be used to detect and identify the ligand uniquely. In particular, the frequency response of the collagenase sample exhibited a strong positive peak 1202 near 5 GHz. The response of the lysozyme sample indicated a relative flat response near 5 GHz and a strong (relative to the collagenase response) positive peak 1204 near 8 GHz. For each of the other numerous proteins examined, the response was unique to each protein, and readily allowed identification of an unknown protein within the group.

This example illustrates how it is possible using particular spectral signals to distinguish between various molecular substances such as proteins. Responses for various complexes can be stored and later recalled to identify unknown samples. In addition, the less-pronounced peaks may be examined collectively to determine patterns for particular ligands.

EXAMPLE 2

(Detection of Secondary Binding: Concanavalin A to Dextran)

This example demonstrates the ability of the methods of the present invention to detect binding of a ligand to a protein. The bio-assay device was similar to the one cited in Example 1 above, and prepared and characterized in a similar manner. The transmission line was also the same as that discussed in Example 1, with a nominal 32 Ω reference impedance, and an ITO cover glass with a DC resistance of 80 Ω and a nominal TDR impedance of 34 Ω.

Concanavalin A (con-A), a glucose binding protein that can be found in jack beans, was used as the primary binding antiligand. The con-A used here was obtained from Sigma Chemical Company. Dextran, a glucose polysaccharide, was used as a ligand to bind con-A. Glucose was used as a competitor to reverse dextran binding and demonstrate specificity. (Dextran and glucose were also obtained from Sigma Chemical Company.)

Figure 9C:
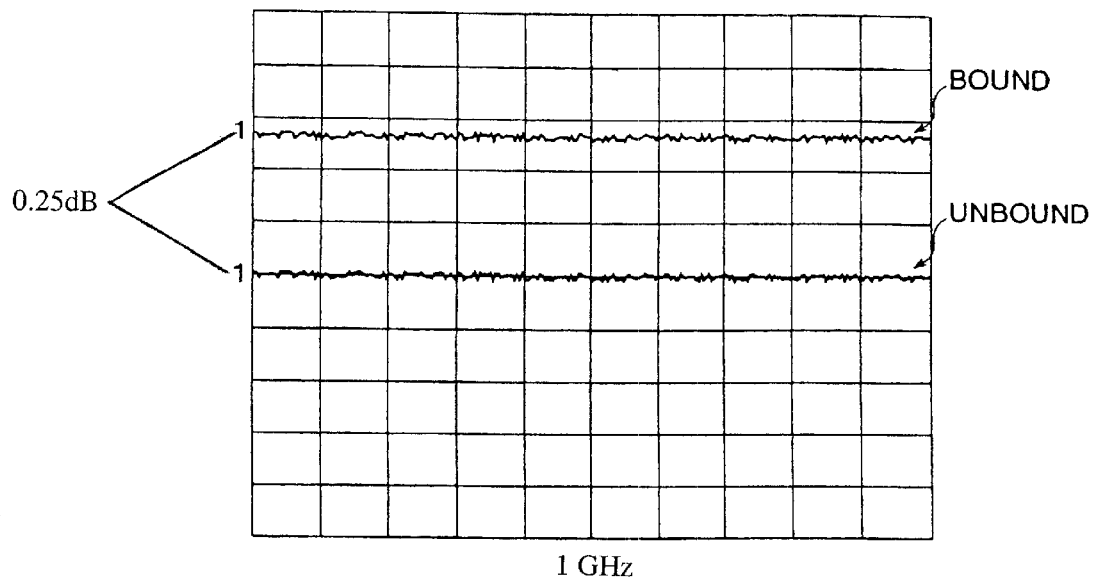
FIG. 9C illustrates the transmission loss response of bound and unbound dextran.

A concentration of approximately 15 $\mu$M solution of con-A was placed directly into the bio-assay device, and allowed to reached equilibrium. Evaporative losses did not dry out the chamber as established by visual inspection. After the system was flushed and stabilized, dextran was added to bind the con-A. After a change in the signal was detected, the chamber was flushed with 10 mg/ml d-PBS and the signal response was measured a second time. This effect is shown in FIG. 9C at 1 GHz. The unbound response being used as the baseline response. As shown, the bounded response appears to be 0.25 dB less noisy than the unbound response. Binding specificity was confirmed by competing off the bound dextran with glucose, followed by a d-PBS flush to free the glucose. The latter step returned the signal to the baseline obtained before the dextran had been added to the device, thus demonstrating specificity of the binding event.

EXAMPLE 3

(Protein Small Molecule Binding)

Using a bio-assay device similar to the one cited in Example 1 above, and prepared and characterized in a similar manner, the bio-assay test fixture and network analyzer set-up was used to demonstrate that small molecules binding to large molecules such as proteins may also be detected with the present invention. In order to probe the bio-assay device at higher frequencies, the device was reproducibly and carefully placed in a Faraday box to shield it from external influences. This allowed the device to be probed at frequencies up to 20 GHz. Initially, con-A was added into the bio-assay device and allowed to bind to the bio-electric interface. A transmission loss measurement was made, stored, and used as the baseline response 1252 as shown in FIG. 9D.

Next, a glucose concentration of 10 mg/ml was added to the bio-assay device and used to bind the con-A antiligand. A transmission loss measurement was made and plotted relative to the baseline response 1252 to determine the change in signal response due to small molecule binding.

Figure 9D:
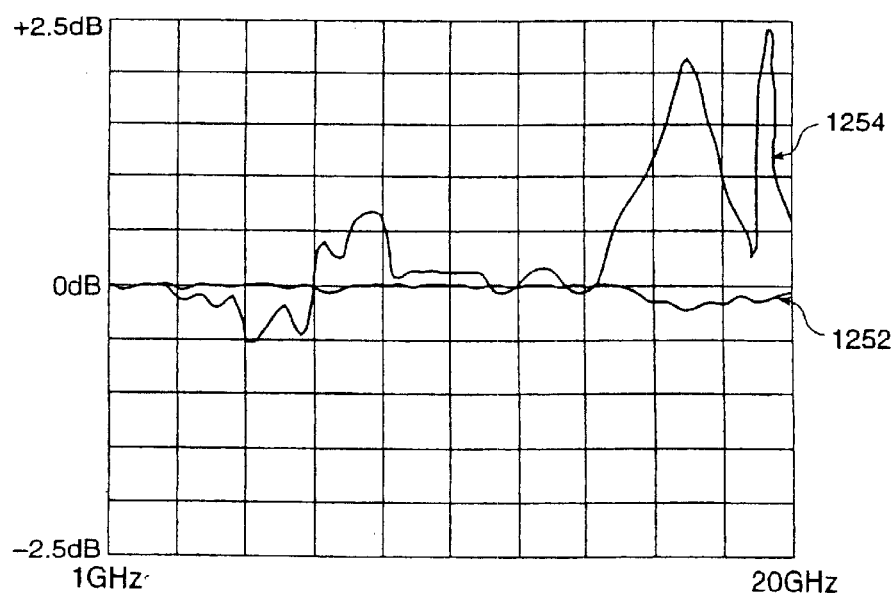
FIG. 9D illustrates the response of concanavalin-A unbound and bound to glucose.

As can be seen from FIG. 9D, the binding response 1254, which corresponds to the binding of glucose to con-A, is distinguishable from the baseline measurement 1252. In particular, the binding response 1254 exhibits 2 large peaks between 16–20 GHz which is not observed in the baseline response 1252. The difference in the measured signal responses 1252 and 1254 provides the basis for detecting when glucose has bound to the con-A antiligand. This was followed by a flush with the d-PBS buffer only, and the response was reversed as the bound glucose dissociated from the con-A. A separate experiment looking at the effect of glucose on the bare chip (i.e. no con-A as an antiligand) showed that glucose alone has little if any effect on the response to electromagnetic interrogation in the above mentioned frequency spectrum, thus showing that the result shown is due entirely to the effect of glucose binding to con-A.

EXAMPLE 4

(Quantitation Titrations)

These experiments demonstrate that the magnitude of the signal change upon a ligand binding to an antiligand is a function of the number of sites that are occupied. The test system using a bio-assay device similar to the one cited in Example 1 above, and prepared and characterized in a similar manner, was used with dextran binding to con-A, with glucose used as a competitive inhibitor. A series of dilutions was created that centered around the binding constant of con-A. Dextran as an antiligand was bound to con-A such that 100% binding occurred. A series of competing glucose concentrations was used to compete off the dextran, so that the concentration of dextran on the molecular binding surface was commensurably decreased.

Figure 9E:
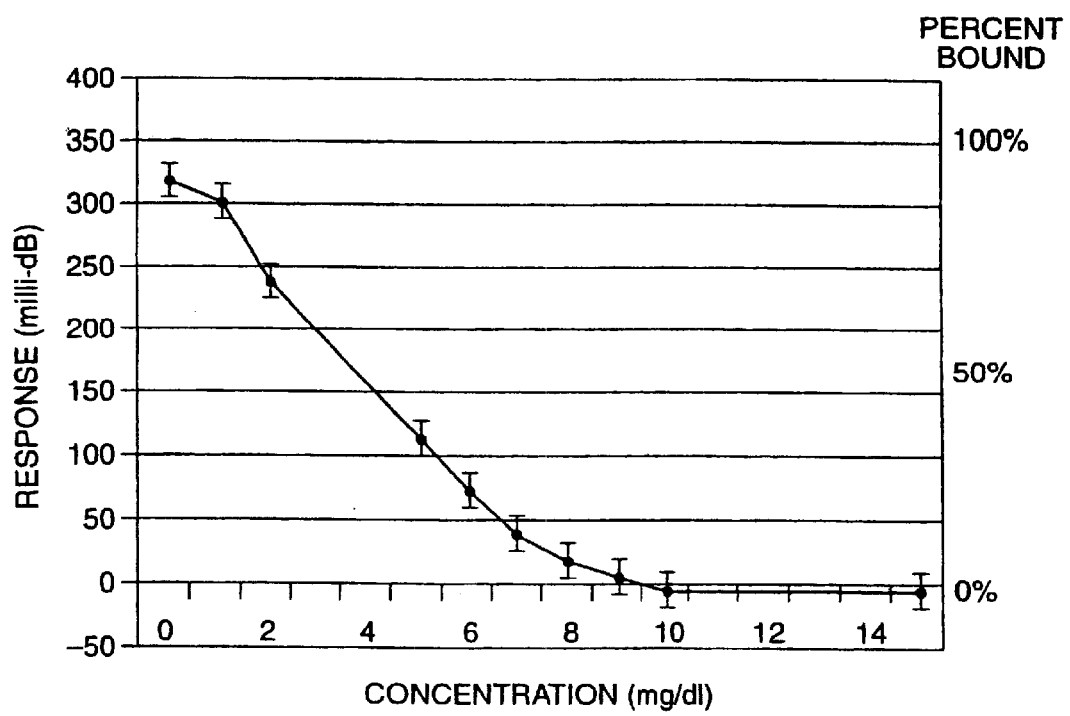
FIG. 9E illustrates the results of a competition titration between dextran and glucose.

The standard transmission line configuration as discussed above was used. Con-A was bound to the molecular binding region and the system was stabilized. The bio-assay device was then flushed with d-PBS and data obtained at 1 GHz. The results of this competition titration are shown in FIG. 9E. The results show how the signal changes as the concentration of glucose is increased from 0 to 15 mg/dl. The signal of the Con-A changes as the dextran is released and the glucose is bound (which actually measures the avidity of the dextran). Specificity was also demonstrated by reversal by glucose of the dextran binding effect.

Table 2 shows the magnitude of the change in transmission loss as a function of the glucose concentration for some selected concentrations.

TABLE 2

| | |
|---|---|
| Dextran fully bound | +320 milli-dB |
| 1 mg/ml glucose | +280 milli-dB |
| 1.33 mg/ml glucose | +275 milli-dB |
| 2 mg/ml glucose | +240 milli-dB |
| 5 mg/ml glucose | +115 milli-dB |
| 10 mg/ml glucose | −5 milli-dB |

Figure 9F:
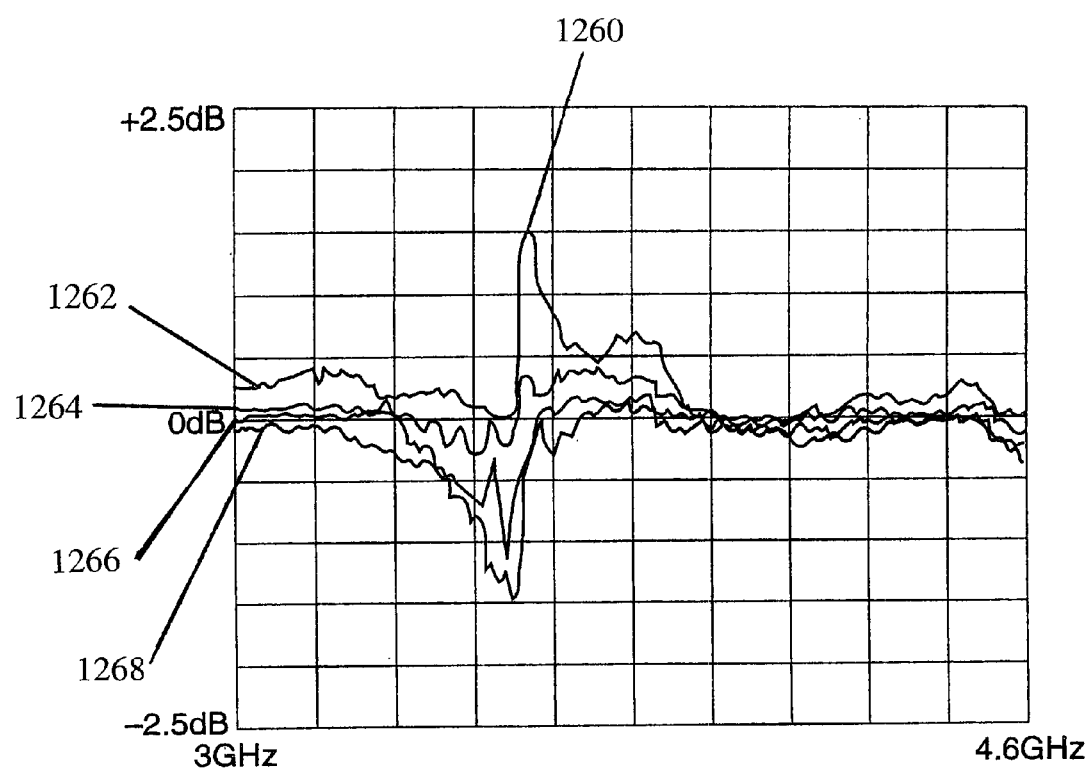
FIG. 9F illustrates the return loss of concanavilin-A as a function of glucose concentration at resonance.

A simple glucose titration was also carried out at a resonant point in the spectrum of con-A at the concentration levels indicated in Table 2, the resonant point 1260 representing the dextran fully bound condition, trace 1262 representing the 1 mg/ml glucose concentration, trace 1264 representing the 2 mg/ml glucose concentration, trace 1266 representing the 5 mg/ml glucose concentration, and trace 1268 representing the 10 mg/ml glucose concentration. FIG. 9F shows the change in the return loss as a function of glucose concentration at this resonance point, demonstrating two effects: First, glucose has a dose-response effect as a ligand which is based on the effect it has on the antiligand (which in this case is con-A). Second, there are regions in the spectra which show a much more sensitive response to the ligand/antiligand binding event than other regions.

A succession of serial dilutions of the dextran solution which took the concentration down below one picomolar ($10^{-12}$ Molar) showed that even at these low concentrations, a significant signal response indicating binding occurred. The time required for the accumulation of the signal ranged from several minutes to ten minutes, but the response was characteristic of the detection of dextran at higher concentrations.

EXAMPLE 5

(Detection in Whole Blood)

The detection of troponin-I (TN-I) was made in whole, unprocessed human blood was made to verify detection capability in a complex environment. The unprocessed human blood was treated with sodium citrate to anticoagulate. An anti-TN-I antibody corresponding to the epitope of TN-I was used for calibration purposes. The interface transmission line of the bio-assay device was coated with anti-TN-I Ab (antiligand). A sample of blood was spiked to a 10 ng/ml concentration of TN-I and a second identical sample of blood was left unspiked as a control.

The experiment consisted of attaching the anti-TN-I Ab antiligand to the device; then first running the unspiked sample across the device; flushing the sample chamber several times to see what the noise of exchange was; followed by the spiked sample, which was also replaced several times to establish a noise floor. In each case, the change in the transmission loss was measured. As a check, the anti-TN-I Ab antiligand was removed from the device. The experiment was subsequently repeated as a control to determine if any other properties of the two blood samples (assumed identical except for the TN-I spike) were responsible for the change. The following table shows the result of this experiment for a probe signal at 1 GHz.

|  | Unspiked sample | Spiked Sample |
| --- | --- | --- |
| Control | <20 milli-dB | <20 milli-dB |
| Anti-TN-I | <20 milli-dB | +275 milli-dB |

Figure 9G:
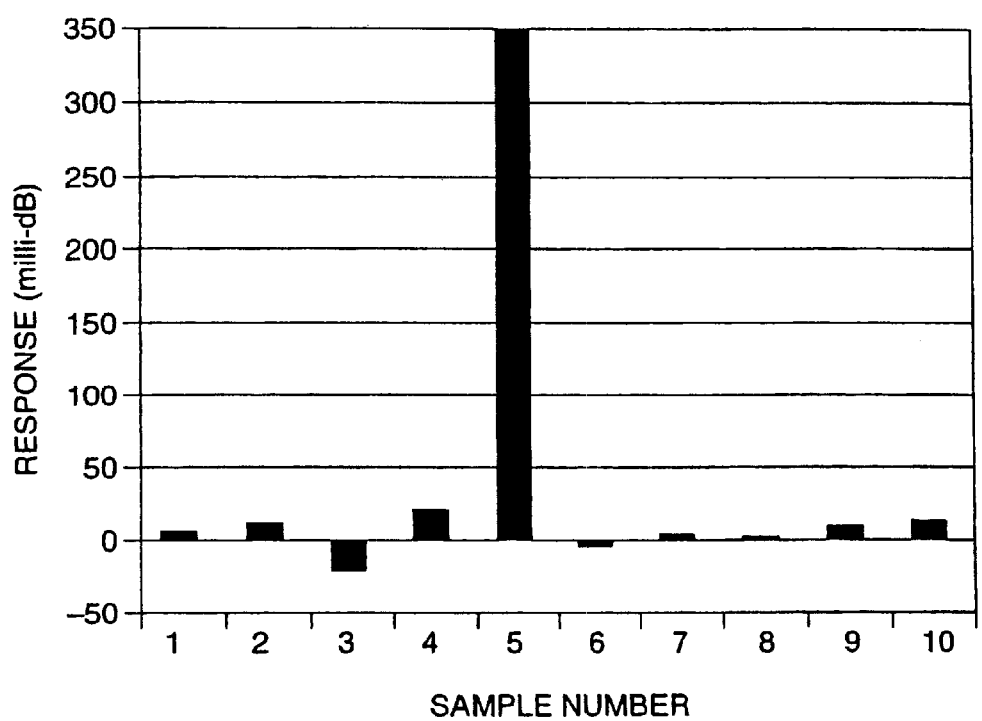
FIG. 9G illustrates the transmission loss response for 10 samples of whole blood probed at 1 GHz indicating detection capability in a complex environment.

In a second series of experiments, ten different samples of blood were obtained from a clinical laboratory, untreated except for being anticoagulated with heparin. One of the samples was divided into two parts, and one of the parts was spiked with the TN-I antigen as described in the previous paragraph. The bio-assay device was then prepared with the anti-TN-I antibody on the surface. Each sample was then serially passed through the bio-assay device, saving the spiked sample for last. The responses for each of these samples, probed at 1 GHz as in the previous experiment, and shown in FIG. 9G. The spiked sample was clearly distinguishable form the rest of the (unspiked) samples.

EXAMPLE 6

(Agonist and Antagonist Binding to Estrogen Receptor)

To detect the effects of a small molecule which induce structural changes in a larger molecule, the estrogen receptor (ER) and various estrogen analogues were used as a model system. The bio-assay device was as described in FIG. 2C, and signal transmission and detection as described in Example 1. The alpha estrogen receptor ($\alpha$-ER) (PanVera, Madison, Wis.) (329 pmol/mg) in a 50 mM Tris-HCl (pH 8.0) buffer was bound to the gold on the transmission line by heating for 30 min. at 37° C.

The steroid estrogen analogues used included $\beta$-estradiol and hydroxytamoxifen (HDT) (both steroid estrogen analogues with differing physiologic function), and a non-steroidal estrogen analogue, diethyl stilbestrol (DES). These analogues are known to cause structural changes in $\alpha$-ER (see, for example, Bourguet, et al., Nature 375:377–382 (1995)). In order to limit variations to those induced by each of the different analogues, the experiment was carried out sequentially on a single device. This allowed for monitoring of differing effects that each analogue has on the dielectric properties of $\alpha$-ER without the variations induced by small differences in the gold transmission line and the assembly. Both DES and $\beta$-estradiol are known agonists with identical structural and biologic function; HDT is a known antagonist which induces many similar, but not identical, structural changes in $\alpha$-ER as $\beta$-estradiol and DES (see, for example, Shiau, et al., Cell 95:927–937 (1998)). DES and $\beta$-estradiol were chosen for this experiment since, as analogues with similar function, they provide a measure of the reproducibility of the experiment. They also made it possible to correlate S-parameters with known structural changes. HDT was used to determine the effect of a different structure for the bound complex on the S-parameters.

The concentrations (10 pM for each compound) and sequence were selected so that a subsequently introduced analogue would compete off the previously bound analogue (i.e., the analogues were applied in order of increasing affinity). Further, each analogue was followed by a flush of the buffer (Tris/HCl) to clear the reaction vessel and start the process of dissociation. The entire experiment was run at 37° C.

Figure 10A:
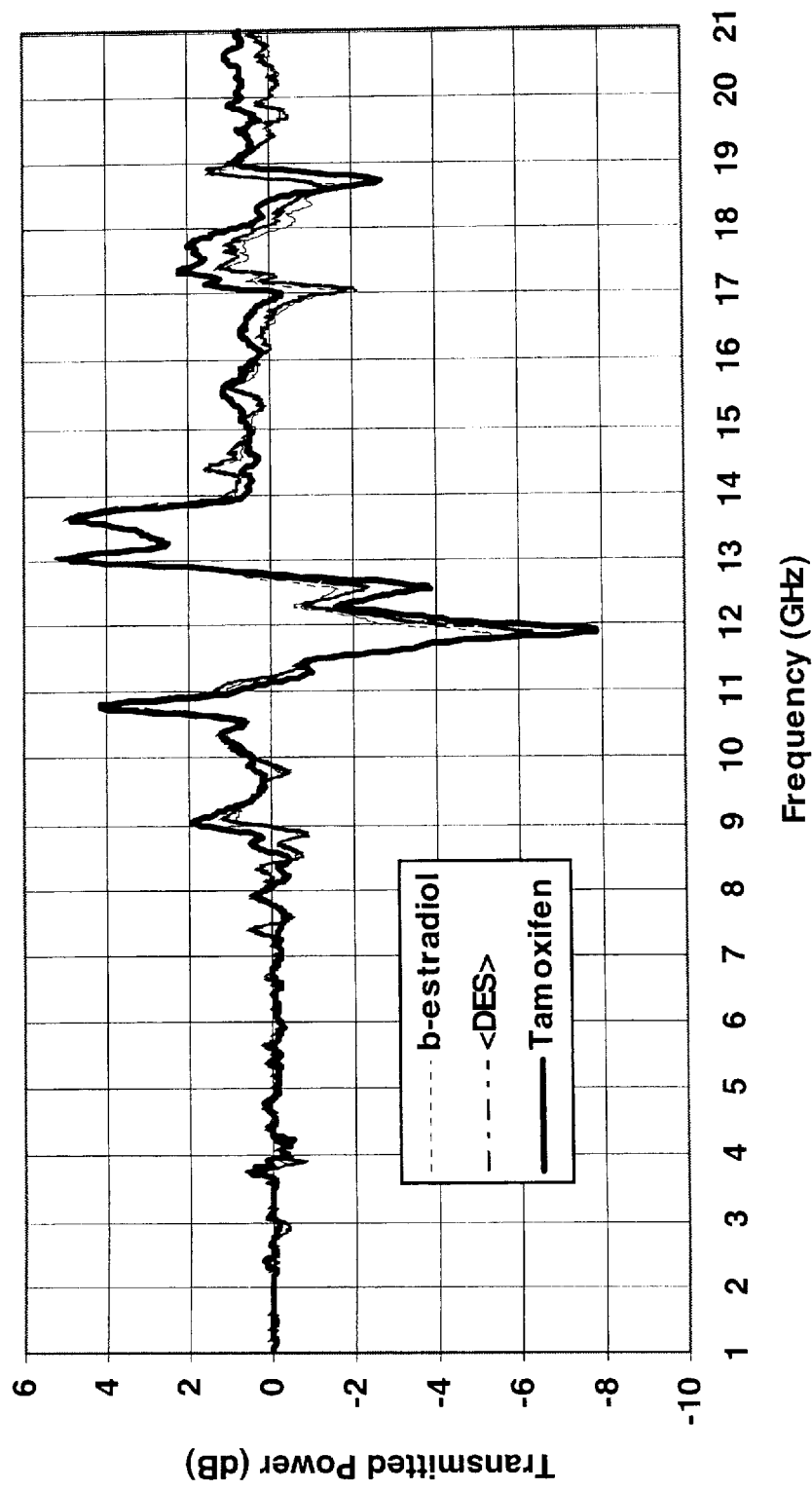
FIG. 10A is a 1–21 GHz scan showing the signals for complexes formed between diethyl stilbestrol (DES), β-estradiol and hydroxytamoxifen (HDT) (dashed line) with the α-estrogen receptor.
Figure 10B:
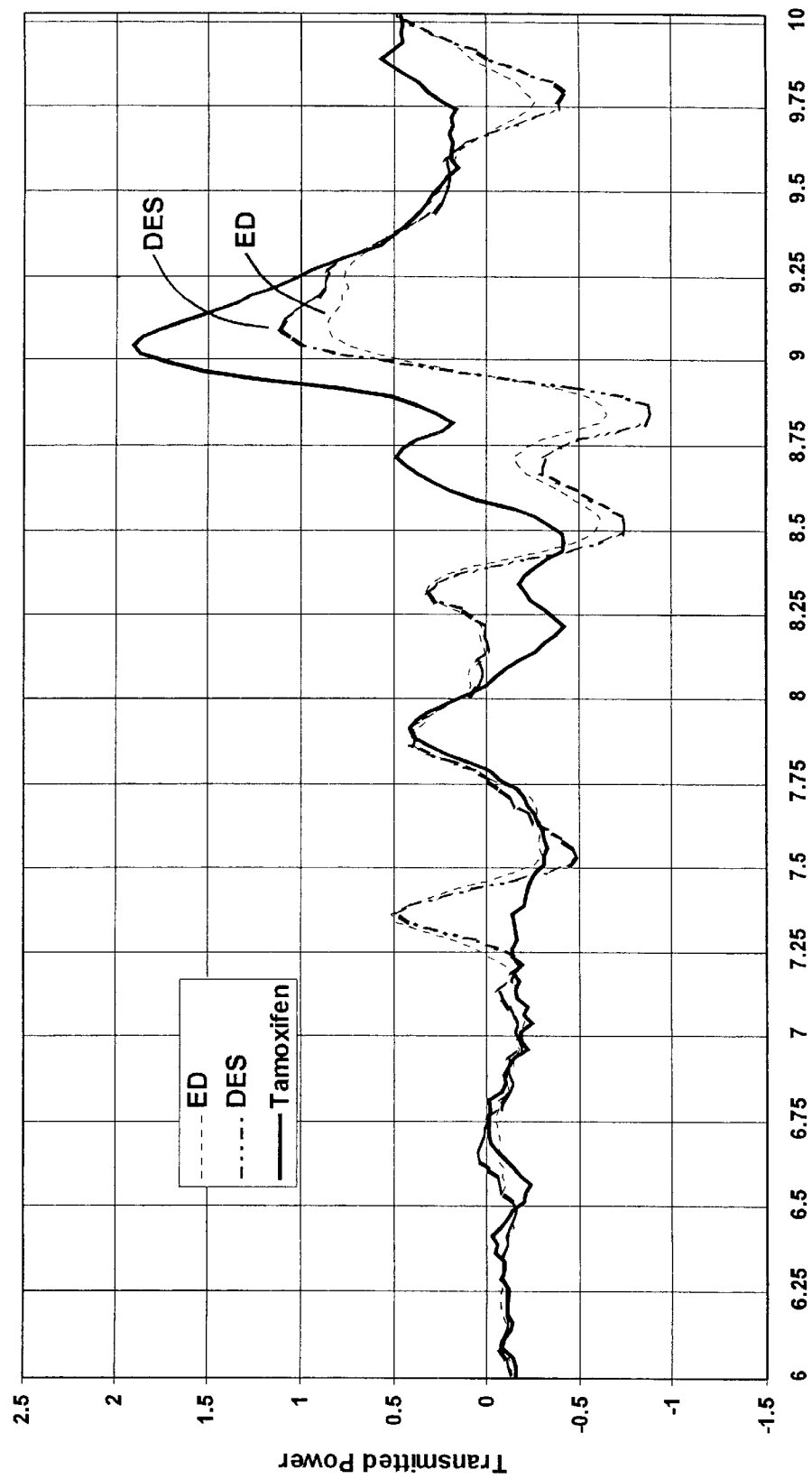
FIG. 10B is an expanded scan (6–10 GHz) of the scan shown in FIG. 10A.

FIG. 10A, is a full scan from 1–21 GHz for each of the compounds. FIG. 10B is an expanded scan from 6 to 10 GHz showing the signals for all three compounds. The response for the two agonists (DES and $\beta$-estradiol) is very similar throughout the spectral window probed. As shown most clearly in the expanded scan (FIG. 10B), however, the antagonist, HDT, yields a quite different spectrum (at 9–9.25 GHz, the solid line with greater amplitude is DES; the solid line with smaller amplitude is for estradiol). In a control experiment, biotin, which is known not to bind to $\alpha$-ER was contacted with $\alpha$-ER under similar conditions and found to give a signal similar to background (results not shown).

This experiment then demonstrates the ability of the methods of the present invention to distinguish between agonist and antagonist binding.

EXAMPLE 7

(Estrogen Receptor Dose Response Experiment Involving Titration with $\beta$-Estradiol)

In order to determine the effects of increasing concentrations of a small molecule known to induce structural changes in a larger molecule, titrations were performed using the $\alpha$-estrogen receptor and $\beta$-estradiol model as a test system. The test device was as described in Example 6, with signal transmission and detection as described in Example 1. $\alpha$-ER (PanVera, Madison, Wis.) (329 pmol/mg) in a 50 mM Tris-HCl (pH 8.0) buffer was bound to the gold on the transmission line for 60 min. at 37° C. Different solutions containing different concentrations of $\beta$-estradiol (1 picoMolar; 250 picoMolar; 500 picoMolar; 750 picoMolar; 1000 picoMolar; 100 nanoMolar; and 500 nanoMolar in Tris-HCl buffer) were tested sequentially on a single device. After testing each $\beta$-estradiol concentration, the system was washed with Tris-HCl buffer; S-parameters were then measured at specific time intervals of 10 min.

Figure 11:
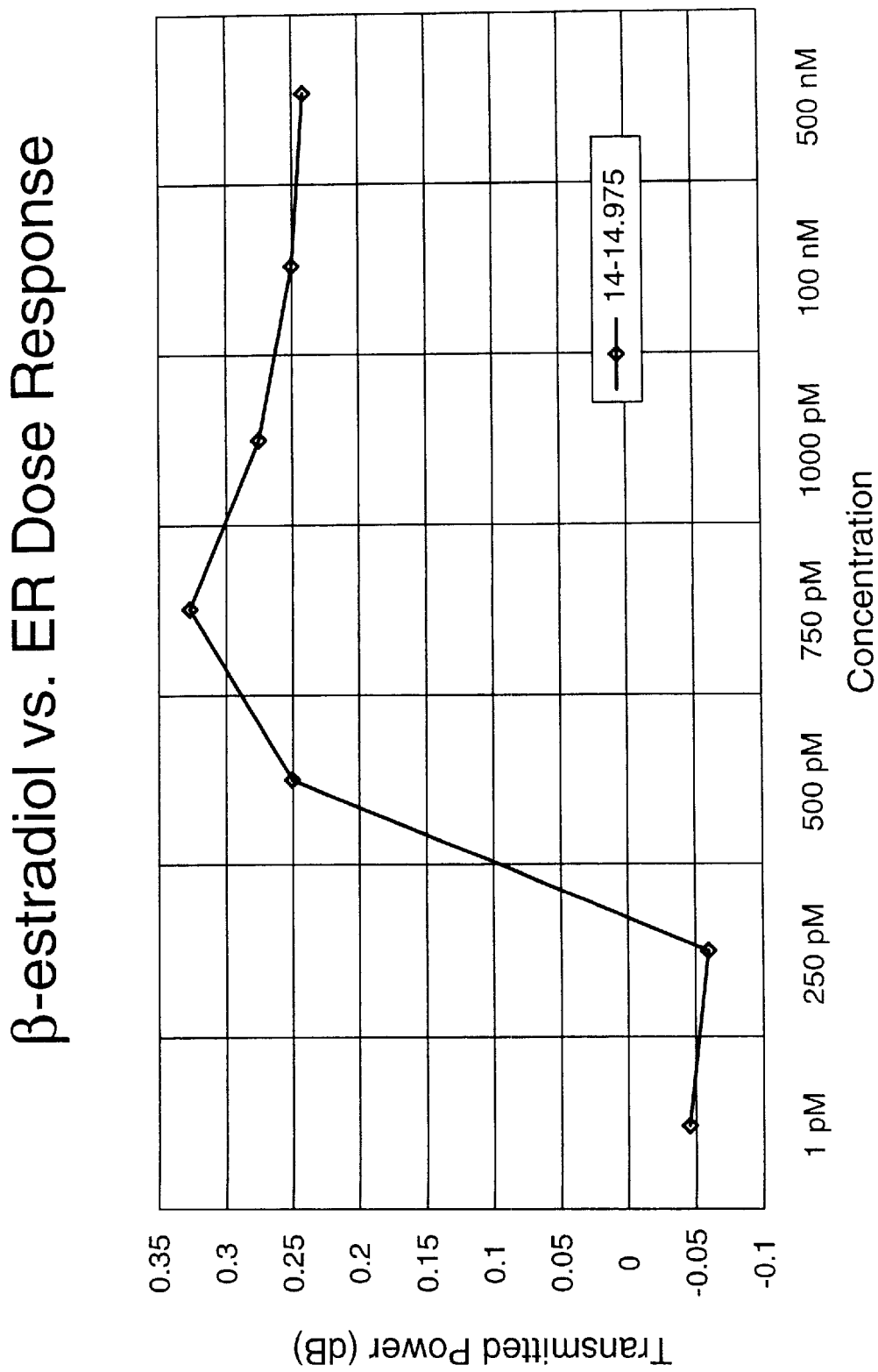
FIG. 11 is a plot of the dose response for titrations of the α-estrogen receptor with β-estradiol.

The most effective dose-response effect occurred from 14 to 15 GHz (i.e., this spectral region showed the greatest variation during the titration). As shown in FIG. 11, when signal measurements (transmitted power) were plotted against $\beta$-estradiol concentration, little to no effect was seen at concentrations of 1 and 250 picoMolar. The greatest response was seen from 250 to 750 picoMolar. The response of β-estradiol on α-ER leveled from 750 picoMolar to 500 nanoMolar. The overall shape of the curve is sigmoidal as expected for the binding of a receptor with a ligand specific thereto.

EXAMPLE 8

(Binding of Anti-Urease Antibody to Urease)

Urease (Sigma Chemical Co., St. Louis, Mo.) was used as an inexpensive model protein to demonstrate the ability of the system to detect the binding of an antibody to an antigen. The bio-assay device was as described in Example 6. Urease was attached to the gold transmission line via an alkane thiol. Attachment involved first washing the gold surface coated glass chip with hot piranha solution (a 1:3 mixture of 3.0% $H_2O_2$/conc. $H_2SO_4$), and then rinsing with distilled water and then allowing the chip to dry. The chip was then immersed into a 5 mM solution of 16-mercaptohexadecanoic acid (Gateway Chemical Technology, St. Louis, Mo.) in chloroform for at least 12 hrs, washed briefly in chloroform and then air dried. Sulfo-NHS (Pierce, Rockford, Ill.) at 1.1 mg/mL in PBS was introduced into the test fixture and allowed to bind to the gold surface for 60 min. The chip was then washed with PBS and urease (0.1 mg/mL) in 1×PBS pH 7.4, introduced into the test fixture, and allowed to bind to the gold surface for 10 min.

Figure 12:
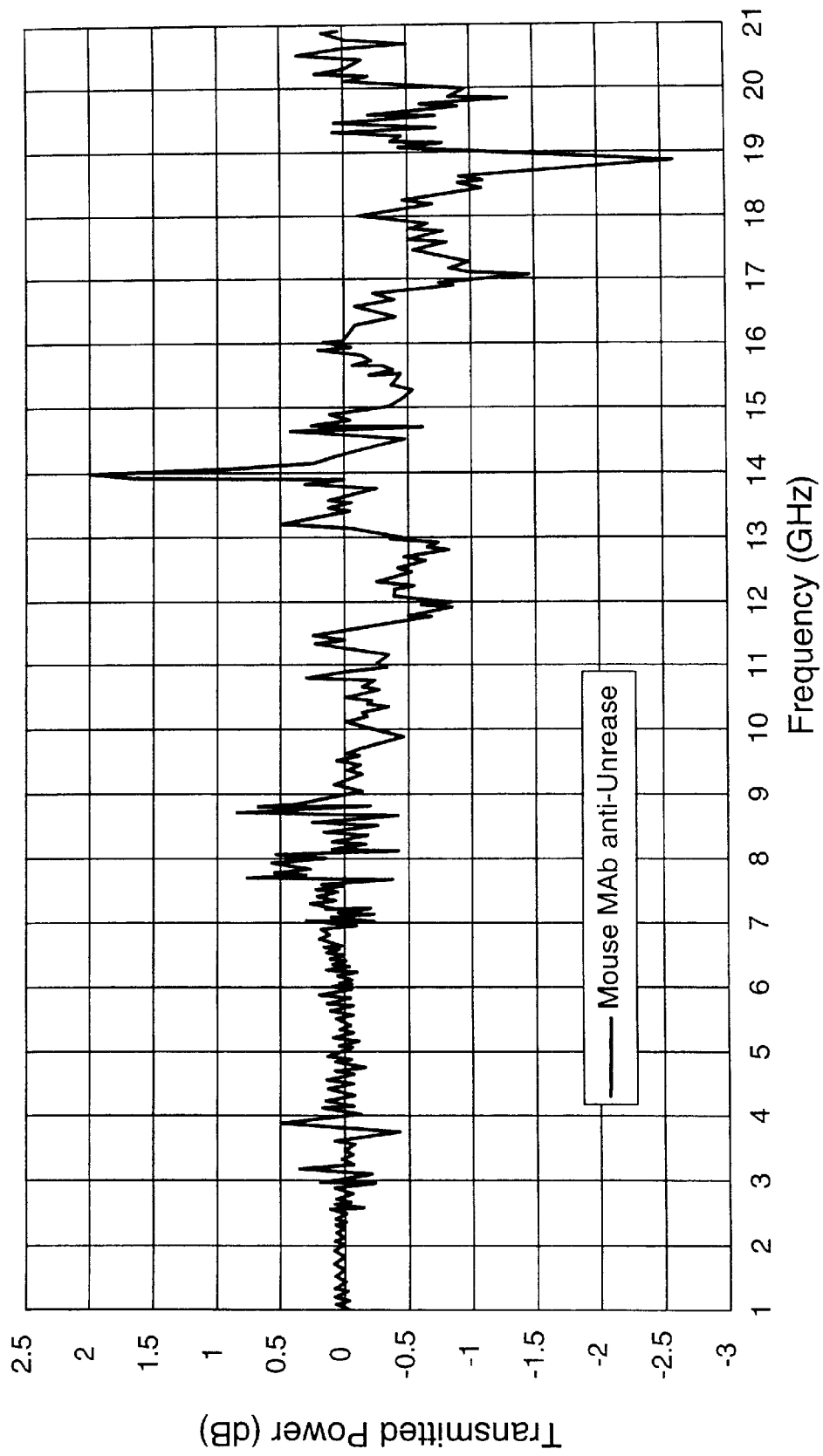
FIG. 12 is a difference spectrum showing the signals for the binding complex formed between anti-urease and urease.

Mouse Monoclonal Anti-Urease Clone UR-25 (IgG1) (Sigma) was diluted to a working dilution of 1:10,000 in PBS and applied to the urease coated chip above. S-parameters were measured over the range of 1–21 GHz and stored after an incubation time of 60 min. The difference spectrum is shown in FIG. 12, and clearly shows the ability to detect the binding of an antibody to an antigen.

While the above is a complete description of possible embodiments of the invention, various alternatives, modifications, and equivalents may be used. For instance a person skilled in the art will appreciate that the signal path of foregoing bio-assay device is not limited to a transmission line. Other transmission mediums, such as conductive or dielectric waveguides may alternatively be used. Further, while some methods have been described such that the protein is initially coupled to the signal path such as a transmission line, it is also possible with many of the methods for the ligand to be the member which is initially coupled to the transmission line.

Further, all publications and patent documents recited in this application are incorporated by reference in their entirety for all purposes to the same extent as if each individual publication and patent document was so individually denoted. The above description should be view as only exemplary embodiments of the invention, the boundaries of which are appropriately defined by the metes and bounds of the following claims.

What is claimed is:

1. A method of screening ligands for the ability to bind to a protein of interest, comprising:
   (a) contacting said protein of interest with a ligand, wherein said protein of interest or said ligand is contained within a molecular binding region which is electromagnetically coupled to a portion of a signal path, said signal path operable to support a signal propagated at one or more frequencies in the range from 10 MHz to 1000 GHz and comprising a transmission line, ground element, and a dielectric layer interposed between said transmission line and said ground element; and
   (b) detecting a response signal at one or more frequencies in said range from 10 MHz to 1000 GHz indicating a binding complex formed between said protein of interest and said ligand, wherein said response signal results from coupling of said propagated signal to said protein, said ligand, or said complex.

2. The method of claim 1, wherein said ligand is selected from the group consisting of a peptide, an oligosaccharide, a nucleic acid, a lipid, an antibody or fragment thereof, a steroid and a cell.

3. The method of claim 1, wherein said ligand is from a library of compounds.

4. The method of claim 3, wherein said library is selected from the group consisting of a random peptide library, a natural products library, a legacy library, a combinatorial library, an oligosaccharide library and a phage display library.

5. The method of claim 1, wherein said protein of interest is selected from the group consisting of a receptor, an antibody or fragment thereof, an enzyme, and a nucleic acid binding protein.

6. The method of claim 1, wherein said detecting step comprises:
   (a) propagating a reference signal along said transmission line before said contacting step to obtain a baseline signal;
   (b) transmitting a test signal along said transmission line after said contacting step to obtain said response signal; and
   (c) comparing said response signal with said baseline signal.

7. The method of claim 1, wherein said protein of interest or said ligand is directly attached to said portion of said transmission line.

8. The method of claim 6, wherein said reference signal and said test signal are microwave signals.

9. The method of claim 1, wherein said protein of interest and said ligand are unlabeled.

10. A method of screening ligands for the ability to combine with a protein of interest, comprising:
    (a) contacting said protein of interest with a ligand, wherein said protein of interest or said ligand is contained within a molecular binding region which is electromagnetically coupled to a portion of a signal path;
    (b) propagating a test signal along said signal path, said signal path operable to support a signal propagated at one or more frequencies in the range from 10 MHz to 1000 GHz and comprising a transmission line, ground element, and a dielectric layer interposed between said transmission line and said ground element, wherein said signal path is non-orthogonal to said molecular binding region; and
    (c) detecting a response signal at one or more frequencies in said range from 10 MHz to 1000 GHz indicating formation of a protein/ligand complex, wherein said response signal results from coupling of said propagated signal to said protein, said ligand, or said complex.

11. A method for analyzing protein binding, comprising acquiring a spectrum for a protein/ligand complex formed between a protein and a test ligand by propagating a test signal along a signal path, said signal path operable to support a signal propagated at one or more frequencies in the range from 10 MHz to 1000 GHz and comprising a transmission line, ground element, and a dielectric layer interposed between said transmission line and said ground element, and detecting a response signal at one or more frequencies in said range from 10 MHz and 1000 GHz indicating formation of said protein/ligand complex, wherein said protein or said ligand is contained within a molecular binding region which is electromagnetically coupled to a portion of said signal path and said response signal results from coupling of said propagated signal to said protein, said ligand, or said complex.

12. The method of claim 11, wherein said protein is a known protein.

13. The method of claim 12, further comprising, examining said spectrum for the presence of a known signal which is characteristic for a known protein/ligand complex formed between said known protein and a particular ligand, the presence of said known signal in said spectrum indicating that said test ligand is said particular ligand.

14. The method of claim 12, further comprising, examining said spectrum for the presence of a known signal which is characteristic of the binding of a known ligand at a particular site on said known protein, the presence of said known signal in said spectrum indicating binding of said test ligand at said particular site.

15. The method of claim 14, wherein said known protein is an enzyme and said particular site is selected from the group of an active site and an allosteric site.

16. The method of claim 14, wherein said protein is a receptor, said known ligand is a natural ligand for said receptor and said particular site is the binding site for said natural ligand.

17. The method of claim 14, wherein said protein is an antibody or fragment thereof, said known ligand is a natural antigen and said particular site is an antigen-binding site for said natural antigen.

18. The method of claim 12, further comprising examining said spectrum for the presence of a known signal which is characteristic for the binding of a particular class of ligand to said known protein, the presence of said known signal in said spectrum indicating that said test ligand is a member of said particular class.

19. The method of claim 18, wherein said known protein is a receptor and said particular class of ligand is an agonist or an antagonist.

20. The method of claim 18, wherein said known protein is an enzyme and said particular class of ligand is a competitive inhibitor or an allosteric effector.

21. The method of claim 11, wherein said test signal is a microwave signal.

22. The method of claim 11, wherein said protein and said test ligand are unlabeled.

23. The method of claim 11, wherein said signal path is a transmission line and said protein or said test ligand is directly attached to said transmission line.

24. The method of claim 11, wherein signal path is non-orthogonal to said molecular binding region.

25. An analytical method, comprising:
(a) contacting a known protein with a sample potentially containing a particular ligand that specifically binds with said known protein, said known protein contained within a molecular binding region which is electromagnetically coupled to a portion of a signal path, said signal path operable to support a signal propagated at one or more frequencies in the range from 10 MHz to 1000 GHz and comprising a transmission line, ground element, and a dielectric layer interposed between said transmission line and said ground element;
(b) allowing sufficient time for said known protein and said particular ligand, if present in said sample, to form a binding complex; and
(c) detecting a response signal at one or more frequencies in said range from 10 MHz to 1000 GHz indicating formation of said binding complex, said response signal indicating the presence of said particular ligand in said sample, wherein said response signal results from coupling of said propagated signal to said protein, said ligand, or said complex.

26. The method of claim 25, wherein said known protein is selected from the group consisting of an antibody or fragment thereof, a receptor, an enzyme, and a nucleic acid binding protein.

27. The method of claim 25, wherein said sample is selected from the group consisting of blood, urine, semen, sputum, and a tissue homogenate.

28. The method of claim 25, wherein said particular ligand is selected from the group consisting of a tumor marker, a drug or drug metabolite, a hormone, an oligosaccharide and a lipid.

29. The method of claim 28, wherein said known protein is directly attached to said continuous transmission line.

30. An analytical method, comprising:
(a) contacting a known ligand with a sample potentially containing a particular protein that specifically binds with said known ligand, said known ligand contained within a molecular binding region which is electromagnetically coupled to a portion of a signal path, said signal path operable to support a signal propagated at one or more frequencies in the range from 10 MHz to 1000 GHz and comprising a transmission line, ground element, and a dielectric layer interposed between said transmission line and said ground element;
(b) allowing sufficient time for said known ligand and said particular protein, if present in said sample, to form a binding complex; and
(c) detecting a response signal at one or more frequencies in said range from 10 MHz to 1000 GHz indicating formation of said binding complex, said response signal indicating the presence of said particular protein in said sample, wherein said response signal results from coupling of said propagated signal to said protein, said ligand, or said complex.

31. An analytical method, comprising:
(a) contacting a known protein with a sample potentially containing a particular ligand that forms a binding complex with said known protein, said known protein contained within a molecular binding region which is electromagnetically coupled to a portion of a signal path, said signal path operable to support the propagation of signals at one or more frequencies in the range from 10 MHz to 1000 GHz and comprising a transmission line, ground element, and a dielectric layer interposed between said transmission line and said ground element;
(b) acquiring a rest spectrum by propagating a test signal at one or more frequencies in said range from 10 MHz to 1000 GHz along said signal path and detecting a response signal at said one or more frequencies in said range from 10 MHz to 1000 GHz indicating the formation of said binding complex; and
(c) examining said test spectrum for the presence of a known signal which is characteristic of said binding complex, the presence of said known signal indicating the presence of said particular ligand in said sample.

32. The method of claim 31, wherein said known protein is selected from the group consisting of an antibody or fragment thereof, a receptor, an enzyme and a nucleic acid binding protein.

33. The method of claim 31, wherein said sample is selected from the group consisting of blood, urine, semen, sputum, and a tissue homogenate.

34. The method of claim 31, wherein said particular ligand is selected from the group consisting of a tumor marker, a drug or drug metabolite, a hormone, an oligosaccharide and a lipid.

35. The method of claim 31, wherein said known protein is directly attached to said continuous transmission line.

36. The method of claim 31, wherein said signal path is non-orthogonal to said molecular binding region.

37. A method of screening ligands for those with the ability to bind a protein of interest, comprising:
- (a) contacting an array comprising a plurality of sites with a sample containing a ligand, each site comprising a known protein contained within a molecular binding region which is electromagnetically coupled to a portion of a signal path located therein, said signal path operable to support a signal propagated at one or more frequencies in the range from 10 MHz to 1000 GHz and comprising a transmission line, ground element, and a dielectric layer interposed between said transmission line and said ground element; and
- (b) detecting a response signal at one or more frequencies in said range from 10 MHz to 1000 GHz indicating the formation of a protein/ligand complex for those sites wherein a protein/ligand complex is formed, wherein said response signal results from coupling of said propagated signal to said protein, said ligand, or said complex.

38. The method of claim 37, wherein said plurality of sites contain the same protein.

39. The method of claim 37, wherein each of said plurality of sites contains a different protein.

40. The method of claim 37, wherein said sample is a plurality of samples, and wherein said contacting step comprises contacting each site with a different one of said plurality of samples.

41. The method of claim 37, wherein said sample comprises a library of ligands.

42. The method of claim 37, wherein said ligand and said plurality of proteins are unlabeled.

43. The method of claim 37, wherein said plurality of proteins are directly attached to said continuous transmission line located with each of said sites.

44. A method of screening ligands for those with the ability to bind a protein of interest, comprising:
- (a) contacting an array comprising a plurality of sites with a sample containing a known protein, each site comprising a signal path and a ligand electromagnetically coupled to a portion of said signal path located therein, said signal path operable to support a signal propagated at one or more frequencies in the range from 10 MHz to 1000 GHz and comprising a transmission line, a ground element, and a dielectric layer interposed between said transmission line and said ground element; and
- (b) detecting a response signal at one or more frequencies said the range from 10 MHz to 1000 GHz indicating the formation of a protein/ligand complex for those sites wherein a protein/ligand complex is formed, wherein said response signal results from coupling of said propagated signal to said protein, said ligand, or said complex.

45. A method of screening ligands for those with the ability to bind a protein of interest, comprising:
- (a) contacting an array comprising a plurality of sites with a sample containing a ligand, each site comprising a signal path and a protein electromagnetically coupled to a portion of the signal path located therein, said signal patb operable to support a signal propagated at one or more frequencies in the range from 10 MHz to 1000 GHz and comprising a transmission line, a ground element, and a dielectric layer interposed between said transmission line and said ground element;
- (b) propagating a test signal at one or more frequencies in said range from 10 MHz to 1000 GHz along the signal path to each of said plurality of elements, wherein said signal path is non-orthogonal to said molecular binding region; and
- (c) detecting a response signal at said one or more frequencies in said range from 10 MHz to 1000 GHz indicating the formation of a protein/ligand complex for those sites wherein a protein/ligand complex is formed, wherein said response signal results from coupling of said propagated signal to said protein, said ligand, or said complex.

* * * * *